(12) United States Patent
Bakker et al.

(10) Patent No.: US 8,492,613 B2
(45) Date of Patent: Jul. 23, 2013

(54) GNTIII EXPRESSION IN PLANTS

(75) Inventors: Hendrikus Antonius Cornelis Bakker, Hannover (DE); Dionisius Elisabeth Antonius Florack, Wageningen (NL); Hendrik Jan Bosch, Wageningen (NL)

(73) Assignee: Stichting Dienst Landbouwkundig Onderzoek, Wageningen (NL)

( * ) Notice: Subject to any disclaimer, the term of this patent is extended or adjusted under 35 U.S.C. 154(b) by 0 days.

(21) Appl. No.: 12/980,651

(22) Filed: Dec. 29, 2010

(65) Prior Publication Data

US 2012/0010155 A1 Jan. 12, 2012

Related U.S. Application Data

(62) Division of application No. 10/508,166, filed as application No. PCT/IB03/01562 on Mar. 18, 2003, now Pat. No. 7,897,842.

(60) Provisional application No. 60/365,769, filed on Mar. 19, 2002, provisional application No. 60/368,047, filed on Mar. 26, 2002.

(51) Int. Cl.
*C12N 15/82* (2006.01)
*C07K 14/435* (2006.01)
*C07K 14/47* (2006.01)
*C07K 14/575* (2006.01)
*C07K 16/00* (2006.01)

(52) U.S. Cl.
USPC ........... 800/288; 800/278; 530/395; 530/397; 530/399; 530/380; 530/381; 530/386; 530/387.1; 435/468

(58) Field of Classification Search
None
See application file for complete search history.

(56) References Cited

U.S. PATENT DOCUMENTS

| | | | |
|---|---|---|---|
| 4,956,282 A | 9/1990 | Goodman et al. | |
| 5,202,422 A | 4/1993 | Hiatt et al. | |
| 5,639,947 A | 6/1997 | Hiatt et al. | |
| 5,874,271 A | 2/1999 | Nishikawa et al. | |
| 5,879,912 A | 3/1999 | Roth | |
| 5,939,288 A | 8/1999 | Thornburg | |
| 5,955,282 A | 9/1999 | Hillman et al. | |
| 5,959,177 A | 9/1999 | Hein et al. | |
| 6,046,040 A | 4/2000 | Nishiguchi et al. | |
| 6,054,304 A | 4/2000 | Taniguchi et al. | |
| 6,331,418 B1 | 12/2001 | Roth | |
| 6,344,600 B1 | 2/2002 | Merot et al. | |
| 6,388,068 B1 | 5/2002 | Satoh et al. | |
| 6,602,684 B1 * | 8/2003 | Umana et al. | 435/69.1 |
| 6,653,459 B1 | 11/2003 | Von Schaewen et al. | |
| 6,998,267 B1 | 2/2006 | Seki et al. | |
| 7,388,081 B2 | 6/2008 | Seki et al. | |
| 7,601,891 B2 | 10/2009 | Bakker et al. | |
| 7,781,647 B2 | 8/2010 | Bakker et al. | |
| 7,897,842 B2 * | 3/2011 | Bakker et al. | 800/298 |
| 8,058,508 B2 | 11/2011 | Bakker et al. | |
| 8,106,169 B2 | 1/2012 | Briggs et al. | |
| 8,193,415 B2 | 6/2012 | Bakker et al. | |
| 8,241,909 B2 | 8/2012 | Seki et al. | |
| 2001/0055584 A1 | 12/2001 | McKenzie et al. | |
| 2002/0019342 A1 * | 2/2002 | Bayer | 514/8 |
| 2002/0174453 A1 | 11/2002 | Danielle et al. | |
| 2004/0072290 A1 | 4/2004 | Umana et al. | |
| 2004/0181827 A1 | 9/2004 | Schaewen et al. | |
| 2004/0214273 A1 | 10/2004 | Fujiyama et al. | |
| 2005/0143564 A1 | 6/2005 | Seki et al. | |
| 2005/0144670 A1 | 6/2005 | Fujiyama et al. | |
| 2005/0223430 A1 | 10/2005 | Bakker et al. | |
| 2006/0253928 A1 | 11/2006 | Bakker et al. | |
| 2007/0089201 A1 | 4/2007 | Briggs et al. | |
| 2007/0214519 A1 | 9/2007 | Fujiyama et al. | |
| 2008/0003680 A1 | 1/2008 | Bakker et al. | |
| 2008/0034456 A1 | 2/2008 | Fujiyama et al. | |
| 2008/0124798 A1 | 5/2008 | Seki et al. | |
| 2010/0122365 A1 | 5/2010 | Bakker et al. | |
| 2011/0030108 A1 | 2/2011 | Bakker et al. | |
| 2011/0067146 A1 | 3/2011 | Rouwendal et al. | |
| 2011/0070649 A1 | 3/2011 | Seki et al. | |
| 2012/0010155 A1 | 1/2012 | Bakker et al. | |
| 2012/0011600 A1 | 1/2012 | Bakker et al. | |
| 2012/0036596 A9 | 2/2012 | Rouwendal et al. | |
| 2012/0060239 A1 | 3/2012 | Fujiyama et al. | |

FOREIGN PATENT DOCUMENTS

| | | |
|---|---|---|
| AU | 1681300 | 6/2000 |
| DE | 19754622 | 6/1999 |
| EP | 0 351 313 A2 | 1/1990 |
| EP | 0 550 756 A1 | 7/1993 |
| EP | 0 737 745 A1 | 10/1996 |
| EP | 0 816 503 A1 | 7/1998 |
| EP | 1 243 647 | 9/2002 |
| JP | S54-055790 | 5/1979 |
| JP | S56-016496 | 2/1981 |
| JP | S56-053696 | 5/1981 |

(Continued)

OTHER PUBLICATIONS

Fitchette-Laine et al. Analysis of N- and O-glycosylation of plant proteins. (1998) Chapter 19 in Methods in Biotechnology; vol. 3: Recombinant Proteins from Plants; editors: Cunningham and Porter, Humana Press Inc.; pp. 271-290.*

(Continued)

*Primary Examiner* — Cathy Kingdon Worley
(74) *Attorney, Agent, or Firm* — Wolf, Greenfield & Sacks, P.C.

(57) ABSTRACT

The invention relates to the field of glycoprotein processing in transgenic plants used as cost efficient and contamination safe factories for the production of recombinant biopharmaceutical proteins or pharmaceutical compositions comprising these glycoproteins. The invention provides a plant comprising a functional mammalian enzyme providing mammalian GnTIII that is normally not present in plants, said plant additionally comprising at least a second mammalian protein or functional fragment thereof that is normally not present in plants.

27 Claims, 41 Drawing Sheets

FOREIGN PATENT DOCUMENTS

| | | |
|---|---|---|
| JP | S56-108798 | 8/1981 |
| JP | S57-149228 | 9/1982 |
| JP | S57-169424 | 10/1982 |
| JP | H10-313867 | 12/1998 |
| JP | 2000-245470 | 9/2000 |
| JP | 2000-287692 | 10/2000 |
| WO | WO 87/00865 | 2/1987 |
| WO | WO 92/18537 | 10/1992 |
| WO | WO 94/12646 | 6/1994 |
| WO | WO 95/02683 | 1/1995 |
| WO | WO 95/21248 | 8/1995 |
| WO | WO 97/04122 | 2/1997 |
| WO | WO 98/31826 | 7/1998 |
| WO | WO 98/31828 | 7/1998 |
| WO | WO 99/09187 | 2/1999 |
| WO | WO 99/24584 | 5/1999 |
| WO | WO 99/29879 | 6/1999 |
| WO | WO 99/38987 | 8/1999 |
| WO | WO 99/38990 | 8/1999 |
| WO | WO 99/51185 | 10/1999 |
| WO | WO 00/28792 | 5/2000 |
| WO | WO 00/29603 | 5/2000 |
| WO | WO 00/34490 | 6/2000 |
| WO | WO 00/49153 | 8/2000 |
| WO | WO 00/52136 | 9/2000 |
| WO | WO 01/29241 | 4/2001 |
| WO | WO 01/29242 | 4/2001 |
| WO | WO 01/31044 | 5/2001 |
| WO | WO 01/31045 | 5/2001 |
| WO | WO 01/49821 | 7/2001 |
| WO | WO 01/49831 | 7/2001 |
| WO | WO 01/62912 | 8/2001 |
| WO | WO 01/64901 | 9/2001 |
| WO | WO 01/81591 | 11/2001 |
| WO | WO 01/82912 | 11/2001 |
| WO | WO 02/00879 | 1/2002 |
| WO | WO 02/057468 | 7/2002 |
| WO | WO 02/007067 | 9/2002 |
| WO | WO 03/001187 | 2/2003 |
| WO | WO 03/007661 | 9/2003 |
| WO | WO 03/007861 | 9/2003 |
| WO | WO 03/007863 | 9/2003 |
| WO | WO 2004/005083 | 6/2004 |

OTHER PUBLICATIONS

Udagama-Randeniya et al. Electrophoretic analysis of coniferyl alcohol oxidase and related laccases. (1994) Electrophoresis; vol. 15; pp. 1072-1077.*
Giddings, G. Transgenic plants as protein factories. (2001) Current Opinion in Biotechnology; vol. 12; pp. 450-454.*
Rishi et al. Molecular Farming in plants: A current perspective. (2001) J. Plant Biochemistry & Biotechnology; vol. 10; pp. 1-12.*
Ikeda et al. Kindetic basis for the donor nucleotide-sugar specificity of B1,4-N-acetylglucosaminyltransferase III. (2000) J. Biochem.; vol. 128; pp. 609-619.*
GENBANK Submission; NIH/NCBI, Accession No. AJ277603. Bakker et al. Apr. 28, 2000.
GENBANK Submission; Accession No. Q92074. Shaper J.H. Nov. 1, 1996.
GENBANK Submission; Accession No. U19890. Shaper J. H. Aug. 3, 1996.
GENBANK Submission; Accession No. BC124813. Aug. 5, 2006.
GENBANK Submission; Accession No. Q08B99. Strausberg et al. Oct. 31, 2006.
GENBANK Submission; Accession No. ADL27179. Hillman J. L. et al. May 20, 2004.
Aoki et al. Golgi retention of a trans-Golgi membrane protein, galactosyl-transferase, requires cysteine and histidine residues within the membrane-anchoring domain. (1992) Cell Biology 89, 4319-4323.
Asano et al., Growth retardation and early death of beta-1,4-galactosyltransferase knockout mice with augmented proliferation and abnormal differentiation of epithelial cells. EMBO J. Apr. 15, 1997;16(8):1850-7.

Bailey et al. Metabolic engineering of N-linked glycoform synthesis systems in Chinese hamster ovary (CHO) cells (1997) Animal Cell Technology, pp. 489-494.
Bakker et al., Galactose-extended glycans of antibodies produced by transgenic plants. Proc Natl Acad Sci U S A. Feb. 27, 2001;98(5):2899-904.
Bakker et al., An *Arabidopsis thaliana* Cdna complements the N-acetylglucosaminyltransferase I deficiency of CHO Lec1 cells. Biochem Biophys Res Commun. Aug. 11, 1999;261(3):829-32.
Borisjuk et al., Production of Recombinant Proteins in Plant Root Exudates. Nat. Biotechnology 17(5): 466-469 (1999).
Boyd et al. The effect of the removal of sialic acid, galactose and total carbohydrate on the functional activity of Campath-1H (1995) Mol Imm. 32, 1311-8.
Cabanes-Macheteau et al., N-Glycosylation of a mouse IgG expressed in transgenic tobacco plants. Glycobiology. Apr. 1999;9(4):365-72.
Chrispeels, M., Glycobiology of Plant Cells, Essentials of Glycobiology, Ch. 20; Varki et al., 1st ed. (1999) Cold Spring Harbor Laboratory Press, NY.
Choi et al., Use of combinatorial genetic libraries to humanize N-linked glycosylation in the yeast *Pichia pastoris*. Proc Natl Acad Sci U S A. Apr. 29, 2003;100(9):5022-7. Epub Apr. 17, 2003.
Chrispeels and Faye, The production of recombinant glycoproteins with defined non-immunogenic glycans. In: Transgenic plants: a production system for industrial and pharmaceutical proteins. John Wiley Pub, UK. 1996:99-113.
Colley "Golgi localization of glycosyltransferases: more questions than answers" (1997) Glycobiology 7(1):1-13.
Cousin et al. "Human variant sex hormone-binding globulin (SHBG) with an additional carbohydrate chain has a reduced clearance rate in rabbit." (1998) J of Clin. Endocrin. and Metab. 83: 245-240.
De Vries et al. Isolation of total and polysomal RNA from plant tissues. (1991) Plant Mol. Biology B6/1-13.
Dieryck et al. Human Haemoglobin from transgenic tobacco (1997) Nature 386, 29-30.
Dinter and Berger, The regulation of cell- and tissue-specific expression of glycans by glycosyltransferases. Adv Exp Med Biol. 1995;376:53-82.
Elbers et al., Influence of growth conditions and developmental stage on N-glycan heterogeneity of transgenic immunoglobulin G and endogenous proteins in tobacco leaves. Plant Physiol. Jul. 2001;126(3):1314-22.
Essl et al., The N-terminal 77 amino acids from tobacco N-acetylglucosaminyltransferase I are sufficient to retain a reporter protein in the Golgi apparatus of *Nicotiana benthamiana* cells. FEBS Lett. Jun. 18, 1999;453(1-2):169-73.
Faye et al Affinity purification of antibodies specific for Asn-linked glycans containing alpha 1—> 3 fucose or beta—> 2 xylose. (1993) Anal Biochem 209, 104-8.
Fischer and Evans, Molecular farming of pharmaceutical proteins. Transgenic Research. 2000;9:279-299.
Fischer et al. Molecular farming of recombinant antibodies in plants. (1999) Biol. Chem. 380: 825-839.
Fitchette Lane et al. N-glycans harboring the Lewis a epitope are expressed at the surface of plant cells. (1997) Plan J 12, 1411-7.
Florack et al. Expression of giant silkmoth cecropin B genes in tobacco. (1995) Transgenic Research 4, 132-141.
Fuchs et al., Purification and characterization of microbially expressed neomycin phosphotransferase II (NPTII) protein and its equivalence to the plant expressed protein. Biotechnology (N Y). Dec. 1993;11(13):1537-42.
Fujiyama et al., In vivo conversion of a glycan to human compatible type by transformed tobacco cells. Biochem Biophys Res Commun. Nov. 30, 2001;289(2):553-7.
Gasser and Fraley, Genetically Engineering Plants for Crop Improvement. Science. Jun. 16, 1989;244(4910): 1293-1299.
Gleeson "Targeting of proteins to the Golgi apparatus" (1998) Histochem Cell Biol. 109: 517-532.
Gomez and Chrispeels, Complementation of an *Arabidopsis thaliana* mutant that lacks complex asparagine-linked glycans with the human cDNA encoding N-acetylglucosaminyltransferase I. Proc Natl Acad Sci U S A. Mar. 1, 1994;91(5):1829-33.

Grabenhorst and Conradt, The cytoplasmic, transmembrane, and stem regions of glycosyltransferases specify their in vivo functional sublocalization and stability in the Golgi. J Biol Chem. Dec. 17, 1999;274(51):36107-16.

Hamilton et al., Production of complex human glycoproteins in yeast. Science. Aug. 29, 2003;301(5637):1244-6.

Handa et al., The alpha 1→3 fucosylation at the penultimate GlcNAc catalyzed by fucosyltransferase VII is blocked by internally fucosylated residue in sialosyl long-chain poly-LacNAc: enzymatic basis for expression of physiological E-selectin epitope. Biochem Biophys Res Commun. Feb. 4, 1998;243(1):199-204.

Herman and Horvitz, Three proteins involved in *Caenorhabditis elegans* vulval invagination are similar to components of a glycosylation pathway. Proc Natl Acad Sci U S A. Feb. 2, 1999;96(3):974-9.

Hen et al., Evaluation of immunoglobulins from plant cells. Biotechnol Prog. Sep.-Oct. 1991;7(5):455-61.

Hess et al., Transformation experiments by pipetting Agrobacterium into the spikelets of wheat (*Triticum aestivum* L.). Plant Science 1990;72:233-44.

Hiei et al., Efficient transformation of rice (*Oryza sativa* L.) mediated by Agrobacterium and sequence analysis of the boundaries of the T-DNA. Plant J. Aug. 1994;6(2):271-82.

Hiei et al., Transformation of rice mediated by Agrobacterium tumefaciens. Plant Mol Biol. Sep. 1997;35(1-2):205-18.

Hollister et al. Stable expression of mammalian β1,4-galactosyltransferase extends the N-glycosylation pathway in insect cells. (1998) Glycobiology 8(5): 473-480.

Hollister et al., Engineering the protein N-glycosylation pathway in insect cells for production of biantennary, complex N-glycans. Biochemistry. Dec. 17, 2002;41(50):15093-104.

Horsch et al. A simple and general method for transferring genes into plants. (1985) Science 227, 1229-1231.

Ihara et al., cDNA cloning, expression, and chromosomal localization of human N-acetylglucosaminyltransferase III (GnT-III). J Biochem (Tokyo). Jun. 1993;113(6):692-8.

Ihara et al "Ectopic Expression of N-acetylglucosaminyltransferase III in transgenic hepatocytes disrupts apolipoprotein B secretion and induces aberrant cellular morphology with lipid storage." Proc Natl Acad Sci USA 1998 95:2526-2530.

Ioffe and Stanley, Mice lacking N-acetylglucosaminyltransferase I activity die at mid-gestation, revealing an essential role for complex or hybrid N-linked carbohydrates. Proc Natl Acad Sci U S A. Jan. 18, 1994;91(2):728-32.

Ishida et al., High efficiency transformation of maize (*Zea mays* L.) mediated by Agrobacterium tumefaciens. Nat Biotechnol. Jun. 1996;14(6):745-50.

Jähne et al., Genetic engineering of ceral crop plants: a review. Euphyica. Kluwer Academic Publishers. 1995:85:35-44.

James et al., Production and characterization of biologically active human GM-CSF secreted by genetically modified plant cells. Protein Expr Purif Jun. 2000;19(1):131-8.

Jarvis and Finn Modifying the insect cell N-glycosylation pathway with immediate early baculovirus expression vectors. (1996) Nat Biotechnol 14, 1288-92.

Jenkins et al., Getting the glycosylation right: implications for the biotechnology industry. Nat Biotechnol. Aug. 1996;14(8):975-81.

Johnson and Chrispeels Substrate specificities of N-acetylglucosaminyl-, fucosyl-, and xylosyltransferases that modify glycoproteins in the Golgi apparatus of bean cotyledons. (1987) Plant Physiology 84, 1301-1308.

Kang et al. "Salt tolerance of *Arabidopsis thaliana* requires maturation of N-glycosylated proteins in the Golgi apparatus." PNAS 2008 105(15):5933-5938.

Kawar et al., Insect cells encode a class II alpha-mannosidase with unique properties. J Biol Chem. May 11, 2001;276(19):16335-40. Epub Feb. 9, 2001.

Kieliszewski et al., Tandem mass spectrometry and structural elucidation of glycopeptides from a hydroxyproline-rich plant cell wall glycoprotein indicate that contiguous hydroxyproline residues are the major sites of hydroxyproline O-arabinosylation. J Biol Chem. Feb. 10, 1995;270(6):2541-9.

Kitagawa et al. Molecular cloning and expression of glucuronyltransferase I involved in the biosynthesis of the glycosaminoglycan-protein linkage region of proteoglycans. (1998) JBC 273:6615-6618.

Kleene et al., Expression of soluble active human beta 1,4 galactosyltransferase in *Saccharomyces cerevisiae*. Biochem Biophys Res Commun. May 30, 1994;201(1):160-7.

Krezdorn et al "Human beta 1,4 galactosyltransferase and alpha 2,6 sialyltransferase expressed in *Saccharomyces cerevisiae* are retained as active enzymes in the endoplasmic reticulum" Eur J Biochem. Mar. 15, 1994;220(3):809-17.

Ku et al., High-level expression of maize phosphoenolpyruvate carboxylase in transgenic rice plants. Nat Biotechnol. Jan. 1999;17(1):76-80.

Leiter et al., Purification, cDNA cloning, and expression of GDP-L-Fuc:Asn-linked GlcNAc alphal,3-fucosyltransferase from mung beans. J Biol Chem. Jul. 30, 1999;274(31):21830-9.

Lerouge et al., Control of the N-Glycosylation of therapeutic glycoproteins produced in transgenic plants: a new challenge for glycobiologists. Molecular Farming of Plants and Animals for Human and Veterinary Medicine. Chapter 4, 2002;73-109.

Lerouge et al., N-glycoprotein biosynthesis in plants: recent developments and future trends. Plant Mol Biol. Sep. 1998;38(1-2):31-48.

Lerouge et al., N-glycosylation of recombinant pharmaceutical glycoproteins produced in transgenic plants: towards an humanisation of plant N-glycans. Curr Pharm Biotechnol. Dec. 2000;1(4):347-54.

Li et al., Cloning, expression and characterization of a cDNA (6A8) encoding a novel human alpha-mannosidase. Eur J Biochem. Dec. 2000;267(24):7176-83. Erratum in: Eur J Biochem Nov. 2001;268(21):5653.

Ma et al. Generation and assembly of secretory antibodies in plants (1995) Science 268, 716-9.

Madson et al., Altered xyloglucans of arabidopsis thalianamutants bind normally to cellulose in vivo and in vitro. Poster from Plant Biology(Rockville) Jul. 27, 2001 Abstract #527.

Magnuson et al., Secretion of biologically active human interleukin-2 and interleukin-4 from genetically modified tobacco cells in suspension culture. Protein Expr Purif. Jun. 1998;13(1):45-52.

Magnuson et al., Enhanced recovery of a secreted mammalian protein from suspension culture of genetically modified tobacco cells. Protein Expr Purif. Mar. 1996;7(2):220-8.

Maras et al., In vitro conversion of the carbohydrate moiety of fungal glycoproteins to mammalian-type oligosaccharides—evidence for N-acetylglucosaminyltransferase-I-accepting glycans from *Trichoderma reesei*. Eur J Biochem. Nov. 1, 1997;249(3):701-7.

Masri et al., Identification of the full-length coding sequence for human galactosyltransferase (beta-N-acetylglucosaminide: beta 1,4-galactosyltransferase). Biochem Biophys Res Commun. Dec. 15, 1988;157(2):657-63.

Milland et al. "The cytoplasmic tail of α1,2-fucosyltransferase contains a sequence for golgi localization" (2001) J. Biol. Chem. 276(15):12012-12018.

Miyake et al., Purification of human erythropoietin. J Biol Chem. Aug. 10, 1977;252(15):5558-64.

Miyoshi et al., The alphal-6-fucosyltransferase gene and its biological significance. Biochim Biophys Acta. Dec. 6, 1999;1473(1):9-20.

Mokrzycki-Issartel et al., A transient tobacco expression system coupled to MALDI-TOF-MS allows validation of the impact of differential targeting on structure and activity of a recombinant therapeutic glycoprotein produced in plants. FEBS Lett. Sep. 25, 2003;552(2-3):170-6.

Munro "Localization of proteins to the Golgi apparatus" (1998) Trends Cell Biol. 8(1): 11-15.

Naigai et al., "N-Glycosylation is Requisite for the Enzyme Activity and Golgi Retention of N-Acetylglucosaminyltransferase III." Glycobiology 7(6):769-776 (1997).

Palacpac et al., Stable expression of human betal,4-galactosyltransferase in plant cells modifies N-linked glycosylation patterns. Proc Natl Acad Sci U S A. Apr. 13, 1999;96(8):4692-7.

Palacpac et al., Structures of N-linked oligosaccharides of glycoproteins from tobacco BY2 suspension cultured cells. Biosci Biotechnol Biochem. Jan. 1999;63(1):35-9.

Philipp et al., "Characterization of nuclear membranes and endoplasmic reticulum isolated from plant tissue" JCB 1976 68:11-29.

Rayon et al. Characterization of N-Glycans from Arabidopsis. Application to a Fucose-Deficient Mutant (1999) Plant Physiology 119, 725-733.

Rayon et al., N-Glycosylation of phytohemagglutinin expressed in bean cotyledons or in transgenic tobacco plants. Plant Physiol Biochem. 1996;34:273-81.

Rishi et al. "Molecular Farming in Plants: A Current Perspective." (2001) J. Plant Biochem. & Biotech 10: 1-12.

Rothman, Protein sorting by selective retention in the endoplasmic reticulum and Golgi stack. Cell. Aug. 14, 1987;50(4):521-2.

Saint-Jore-Dupas et al. "Plant N-Glycan Processing Enzymes Employ Different Targeting Mechanisms for Their Spatial Arrangement along the Secretory Pathway." The Plant Cell 2006 18:3182-3200.

Saito et al. Integration and expression of a rabbit liver cytochrome P-450 gene in transgenic Nicotiana tabacum (1991) Proc. Natl. Acad. Sci. 88, 7041-7045.

Sakai et al., Fatty Acid acylation of apoE by human monocyte/marophages and helptocytes. Apr. 1998; 417. Abstract.

Sakai et al., Human glycosyltransferase expression and intracellular/intercellular glycoprotein sugar chain structure in cultured tobacco BY2 cells. Corrected title: Expression of human β 1,4-galactosyltransferase in tobacco BY2 cells modifies glycosylation patterns of intracellular and extracellular glycoproteins. IC Biotech. Osaska, Nara Institute. Mar. 1998. Abstract.

Sakai et al., "Expression of Human β1,4-Galactosyltransferase in Tobacco BY2 Cells Modifies Glycosylation Patterns of Intracellular and Extracellular Glycoproteins," Translation of Abstract from the Ann. Meeting of Japan Society for Bioscience, Biotechnology, and Agrochemistry, Published Mar. 1998. (Additional translation of Sakai et al previously submitted).

Schachter, The 'yellow brick road' to branched complex N-glycans. Glycobiology. Nov. 1991;1(5):453-61.

Scherer et al., "Action and Inhibition of Endogenous Phospholipases during Isolation of Plant Membranes" Plant Physiol 1978 62:933-37.

Schindler et al. Arabinogalactan proteins in maize coleoptiles: developmental relationship to cell death during xylem differentiation but not to extention growth. (1995) Plant JU 7, 25-36.

Seveno et al., Glycoprotein Sialylation in plants? Nat Biotechnol. Nov. 2004;22(11):1351-2.

Shah et al., Sialylated endogenous glycoconjugates in plant cells. Nat Biotechnol. Dec. 2003;21(12):1470-1. Epub Nov. 9, 2003.

Shaper et al. Bovine galactosyltransferase: identification of a clone by direct immunological screening of a cDNA expression library. (1986) Proc Natl Acad Sci USA 83, 1573-7.

Smant et al. Potato root diffusate—induced secretion of soluble, basic proteins originating from the subventral esophageal glands of potato cyst nematodes (1997) Phytopathology 87, 839-845.

Stanley and Ioffe Glycosyltransferase mutants: key to new insights in glycobiology (1995) Faseb j 9, 1436-44.

Stanley et al. CHO cells provide access to novel N-glycans and developmentally regulated glycosyltransferases. (1996) Glycobiology 6, 695-9.

Staudacher E, "Functional purification and characterization of a GDP-fucose: beta-N-acetylglucosamine (Fuc to Asn linked GlcNAc) alpha 1,3-fucosyltransferase from mung beans." Glycoconj J. Dec. 1995;12(6):780-6.

Staudacher E, "Strict order of (Fuc to Asn-linked GlcNAc) fucosyltransferases forming coredifucosylated structures." Glycoconj J. Apr. 1998;15(4):355-60.

Strasser et al., Molecular cloning of cDNA encoding N-acetylglucosaminyltransferase II from Arabidopsis thaliana. Glycoconj J. Dec. 1999;16(12):787-91.

Strasser et al., "Molecular cloning and functional expression of beta 1,2-sylosyltransferase cDNA from Arabidopsis thaliana[1]" Febs Letters, Elsevier, Amsterdam, NL, Apr. 2000 472(1): 105-108.

Strasser et al. "Molecular basis of N-acetylglucosaminyltransferase I deficiency in Arabidopsis thaliana plants lacking complex N-glycans." Biochem J. 2005 387:385-391.

Sturm et al. "Subcellular localization of glycosidases and glycosyltransferases involved in the processing of N-linked oligosaccharides" (1987) Plant Physiol. 85(3):741-745.

Takahashi et al., Xylose-containing common structural unit in N-linked oligosaccharides of laccase from sycamore cells. Biochemistry. 1986;25(2):388-95.

Tang et al., The transmembrane domain of N-glucosaminyltransferase I contains a Golgi retention signal. J Biol Chem. May 15, 1992;267(14):10122-6.

Taniguchi et al., A glycomic approach to the identification and characterization of glycoprotein function in cells transfected with glycosyltransferase genes. Proteomics. Feb. 2001;1(2):239-47.

Terayama et al., Cloning and functional expression of a novel glucuronyltransferase involved in the biosynthesis of the carbohydrate epitope HNK-1. Proc Natl Acad Sci U S A. Jun. 10, 1997;94(12):6093-8.

Terayama et al., "Purification and Characterization of a Glucuronyltransferase Involved in the Biosynthesis of the HNK-1 Epitope on Glycoproteins from Rat Brain." The Journal of Biological Chemistry 273(46):30295-30300 (1998).

Thanavala et al. Immunogenicity of transgenetic plant derived hepatitis B surface antigen. (1995) Proc Natl Acad Sci USA 92, 3358-3361.

Umana et al. Engineered glycoforms of an antineuroblastoma IgG1 with optimize antibody-dependent cellular cytotoxic activity. (1999) Nature Biotech. 17: 176-180.

Van Engelen et al., Coordinate expression of antibody subunit genes yields high levels of functional antibodies in roots of transgenic tobacco. Plant Mol Biol. Dec. 1994;26(6):1701-10.

Van Engelen et al. pBINPLUS: an improved plant transformation vector based on pBIN19. (1995) Transgenetic Res 4, 288-90.

Van Ree et al., Beta(1,2)-xylose and alpha(1,3)-fucose residues have a strong contribution in IgE binding to plant glycoallergens. J Biol Chem. Apr. 14, 2000;275(15):11451-8.

Vitale and Chrispeels, Transient N-acetylglucosamine in the biosynthesis of phytohemagglutinin: attachment in the Golgi apparatus and removal in protein bodies. J Cell Biol. Jul. 1984;99(1 Pt 1):133-40.

Voelker et al., In vitro mutated phytohemagglutinin genes expressed in tobacco seeds: role of glycans in protein targeting and stability. Plant Cell. Jan. 1989;1(1):95-104.

Von Schaewen et al. Isolation of a mutant arabidopsis plant that lacks N-acetyl glucosaminyl transferase I and is unable to synthesize Golgi-modified complex N-linked glycans. (1993) Plant Physiol 102, 1109-18.

Warner, T.G., Metabolic engineering glycosylation: biotechnology's challenge to the glycobiologist in the next millenium; Carbohydrates in chemistry and biology, part II vol. 4. editors Earnst et al. (2000) Wiley-VCH. 1042-64.

Wee et al., Targeting of active sialyltransferase to the plant Golgi apparatus. Plant Cell. Oct. 1998;10(10):1759-68.

Whitelam GC., The production of recombinant proteins in plants. (1995) J. Sci. Food Agric., 68:1-9.

Wiebauer et al., Nuclear pre-mRNA processing in plants: distinct modes of 3'splice-site selection in plants and animals (1988) MCB: vol. 8 pp. 2042-2051.

Wilson et al., Core alpha1,3-fucose is a key part of the epitope recognized by antibodies reacting against plant N-linked oligosaccharides and is present in a wide variety of plant extracts. Glycobiology. Jul. 1998;8(7):651-61.

Wilson et al., Cloning and expression of cDNAs encoding alpha1,3-fucosyltransferase homologues from Arabidopsis thaliana. Biochim Biophys Acta. Jul. 2, 2001;1527(1-2):88-96.

Wright and Morrison, Effect of glycosylation on antibody function: implications for genetic engineering. Trends Biotechnol. Jan. 1997;15(1):26-32.

Yamaguchi et al., Genomic structure and promoter analysis of the human alpha1, 6-fucosyltransferase gene (FUT8). Glycobiology. Jun. 2000;10(6):637-43.

Yamaguchi and Fukuda Golgi retention mechanism of β-1,4-Galactosyltransferase (1995) J of Biol Chemistry 270(20): 12170-12176.

Yin et al., [Obtaining transgenic rice plants and their progenies using *Agrobacterium tumefaciens*] Yi Chuan Xue Bao. Dec. 1998;25(6):517-24. Chinese.

Yoshida et al., Molecular biology and application of plant peroxidase genes. Appl Microbiol Biotechnol. Feb. 2003;60(6):665-70. Epub Dec. 18, 2002.

Yoshida et al., Expression of β1 4 galactosyltransferase in tobacco culture cell. Program for Congress of the Society for Bioscience and Bioengineering of Japan. Sep. 15, 1995;1-5.

Yosida et al., "Challenge for production of human-compatible glycoprotein therapeutics in yeast", Bioscience and Industry, vol. 54, pp. 420-422 (1996).

Zhang et al., Transformation of tobacco using human β-1, 4 galactosyltransferase gene and regeneration of transgenic plants. Annual reports of IC Biotech. 1995;18:241-7.

Zhang et al., Agrobacterium-mediated transformation of elite indica and japonica rice cultivars. Mol Biotechnol. Dec. 1997;8(3):223-31.

Zhang and Wang, Quantitative analysis and process monitoring of site-specific glycosylation microheterogeneity in recombinant human interferon-gamma from Chinese hamster ovary cell culture by hydrophilic interaction chromatography. J Chromatogr B Biomed Sci Appl. Aug. 7, 1998;712(1-2):73-82.

Zhu et al., Beta 1,4 N-acetylgalactosaminyltransferase (GM2/GD2/GA2 synthase) forms homodimers in the endoplasmic reticulum: a strategy to test for dimerization of Golgi membrane proteins. Glycobiology. Oct. 1997;7(7):987-96.

Terashima et al., "Effect of Osmotic Pressure on Human α1-Antitrypsin Production by Plant Cell Culture," *Biochemical Engineering Journal* 4 (1999) 31-36.

Davies et al., Expression of GnTIII in a recombinant anti-CD20 CHO production cell line: Expression of antibodies with altered glycoforms leads to an increase in ADCC through higher affinity for FC gamma RIII. Biotechnol Bioeng. Aug. 20, 2001;74(4):288-94.

Fast et al., The role of the carbohydrate chains of Gal beta-1,4-GlcNAc alpha 2,6-sialyltransferase for enzyme activity. Biochim Biophys Acta. Oct. 6, 1993;1202(2):325-30.

Huether et al., Glyco-engineering of moss lacking plant-specific sugar residues. Plant Biol (Stuttg). May 2005;7(3):292-9.

Rayon et al., The protein N-glycosylation in plants. Journal Exper Botany. Sep. 1998. 49(326):1463-72.

Sakai et al., Human glycosyltransferase expression and intracellular/intercellular glycoprotein sugar chain structure in cultured tobacco BY2 cells. IC Biotech. Osaska, Nara Institute. Mar. 1998. Abstract. Original with English Abstract.

* cited by examiner

3A
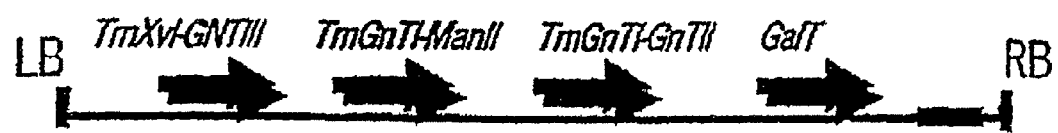
X
3B
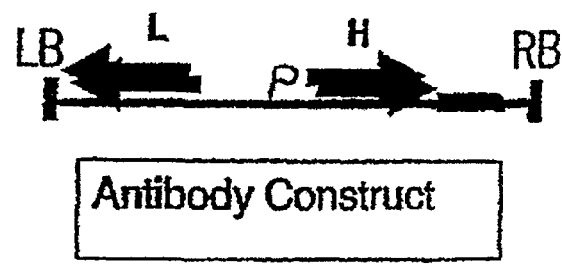
FIG. 3

Nucleotide sequence (incl. myc-tag)

CCATGGTGATGAGACGCTACAAGCTCTTTCTCATGTTCTGTATGGCCGGCCTG
TGCCTCATCTCCTTCCTGCACTTCTTCAAGACCCTGTCCTATGTCACCTTCCCC
CGAGAACTGGCCTCCCTCAGCCCTAACCTGGTGTCCAGCTTTTTCTGGAACAA
TGCCCCGGTCACGCCCCAGGCCAGCCCCGAGCCAGGAGGCCCTGACCTGCTG
CGTACCCCACTCTACTCCCACTCGCCCCTGCTGCAGCCGCTGCCGCCCAGCAA
GGCGGCCGAGGAGCTCCACCGGGTGGACTTGGTGCTGCCCGAGGACACCACC
GAGTATTTCGTGCGCACCAAGGCCGGCGGCGTCTGCTTCAAACCCGGCACCA
AGATGCTGGAGAGGCCGCCCCGGGACGGCCGGAGGAGAAGCCTGAGGGGG
CCAACGGCTCCTCGGCCCGGCGGCCACCCCGGTACCTCCTGAGCGCCCGGGA
GCGCACGGGGGCCGAGGCGCCCGGCGCAAGTGGGTGGAGTGCGTGTGCCT
GCCCGGCTGGCACGGACCCAGCTGCGGCGTGCCCACTGTGGTGCAGTACTCC
AACCTGCCCACCAAGGAGCGGCTGGTGCCCAGGGAGGTGCCGCGCCGCGTCA
TCAACGCCATCAACGTCAACCACGAGTTCGACCTGCTGGACGTGCGCTTCCA
CGAGCTGGGCGACGTGGTGGACGCCTTTGTGGTGTGCGAGTCCAACTTCACG
GCTTATGGGGAGCCGCGGCCGCTCAAGTTCCGGGAGATGCTGACCAATGGCA
CCTTCGAGTACATCCGCCACAAGGTGCTCTATGTCTTCCTGGACCACTTCCCG
CCCGGCGGCCGGCAGGACGGCTGGATCGCCGACGACTACCTGCGCACCTTCC
TCACCCAGGACGGCGTCTCGCGGCTGCGCAACCTGCGGCCCGACGACGTCTT
CATCATTGACGATGCGGACGAGATCCCGGCCCGTGACGGCGTCCTTTTCCTCA
AGCTCTACGATGGCTGGACCGAGCCCTTCGCCTTCCACATGCGCAAGTCGCTC
TACGGCTTCTTCTGGAAGCAGCCGGGCACCCTGGAGGTGGTGTCAGGCTGCA
CGGTGGACATGCTGCAGGCAGTGTATGGGCTGGACGGCATCCGCCTGCGCCG
CCGCCAGTACTACACCATGCCCAACTTCAGACAGTATGAGAACCGCACCGGC
CACATCCTGGTGCAGTGGTCGCTGGGCAGCCCCTGCACTTCGCCGGCTGGC
ACTGCTCCTGGTGCTTCACGCCCGAGGGCATCTACTTCAAGCTCGTGTCCGCC
CAGAATGGCGACTTCCACGCTGGGGTGACTACGAGGACAAGCGGGACCTGA
ACTACATCCGCGGCCTGATCCGCACCGGGGCTGGTTCGACGGCACGCAGCA
GGAGTACCCGCCTGCAGACCCAGCGAGCACATGTATGCGCCCAAGTACCTG
CTGAAGAACTACGACCGGTTCCACTACCTGCTGGACAACCCCTACCAGGAGC
CCAGGAGCACGGCGGCGGGCGGGTGGCGCCACAGGGGTCCCGAGGGAAGGC
CGCCCGCCCGGGGCAAACTGGACGAGGCGGAAGTCGAACAAAAACTCATCT
CAGAAGAGGATCTGAATTAGGATCC

FIG. 4A

PROTEIN SEQUENCE

MVMRRYKLFL MFCMAGLCLI SFLHFFKTLS YVTFPRELAS LSPNLVSSFF
WNNAPVTPQA SPEPGGPDLL RTPLYSHSPL LQPLPPSKAA EELHRVDLVL
PEDTTEYFVR TKAGGVCFKP GTKMLERPPP GRPEEKPEGA NGSSARRPPR
YLLSARERTG GRGARRKWVE CVCLPGWHGP SCGVPTVVQY SNLPTKERLV
PREVPRRVIN AINVNHEFDL LDVRFHELGD VVDAFVVCES NFTAYGEPRP
LKFREMLTNG TFEYIRHKVL YVFLDHFPPG GRQDGWIADD YLRTFLTQDG
VSRLRNLRPD DVFIIDDADE IPARDGVLFL KLYDGWTEPF AFHMRKSLYG
FFWKQPGTLE VVSGCTVDML QAVYGLDGIR LRRRQYYTMP NFRQYENRTG
HILVQWSLGS PLHFAGWHCS WCFTPEGIYF KLVSAQNGDF PRWGDYEDKR
DLNYIRGLIR TGGWFDGTQQ EYPPADPSEH MYAPKYLLKN YDRFHYLLDN
PYQEPRSTAA GGWRHRGPEG RPPARGKLDE AEVEQKLISE EDLN

FIG. 4B

Plasmid pDAB4005 (7027 bp)
Description: ZmUbilpromoter + intron/GUS/Per5 3'UTR

| Nucleotide start | Nucleotide end | Sequence Feature |
|---|---|---|
| 1 | 115 | Linker sequence with multiple cloning site: CATGATTACGCCAAGCTAGCGGCCGCATTCCCGGGAAGCTA GGCCACCGTGGCCCGCCTGCAGGGGAAGCTTGCATGCCTGC AGATCCCCGGGGATCCTCTAGAGTCGACCTGCA |
| 116 | 2105 | Maize ubiquitin promoter + intron |
| 1093 | 2105 | Maize ubiquitin intron |
| 2106 | 2125 | Linker sequence: GGGTACCCCCGGGGTCGAC |
| 2126 | 3967 | GUS coding region |
| 3968 | 3985 | Linker sequence: TAATGAGCTCGTTTAAA |
| 3986 | 4350 | Maize peroxidase-5 3' UTR |
| 4351 | 4405 | Linker sequence: CGGCCGGCCTAGCTAGCCACGGTGGCCAGATCCACTAGTTC TAGAGCGGCCGCTT |
| 4406 | 7027 | Puc19 |
| 5006 | 5866 | Ampicillin resistance gene |

Sequence
```
  1 CATGATTACG CCAAGCTAGC GGCCGCATTC CCGGGAAGCT AGGCCACCGT
 51 GGCCCGCCTG CAGGGGAAGC TTGCATGCCT GCAGATCCCC GGGGATCCTC
101 TAGAGTCGAC CTGCAGTGCA CTGCAGTCGA GCGTGACCCG GTCGTGCCCC TCTCTAGAGA
```

FIG 5B

```
151  TAATGAGCAT TGCATGTCTA AGTTATAAAA AATTACCACA TATTTTTTTT
201  GTCACACTTG TTTGAAGTGC AGTTTATCTA TCTTTATACA TATATTTAAA
251  CTTTAATCTA CGAATAATAT AATCTATAGT ACTACAATAA TATCAGTGTT
301  TTAGAGAATC ATATAAATGA ACAGTTAGAC ATGGTCTAAA GGACAATTGA
351  GTATTTTGAC AACAGGACTC TACAGTTTTA TCTTTTTAGT GTGCATGTGT
401  TCTCCTTTTT TTTTGCAAAT AGCTTCACCT ATATAATACT TCATCCATTT
451  TATTAGTACA TCCATTAGG GTTTAGGGTT AATGGTTTTT ATAGACTAAT
501  TTTTTAGTA CATCTATTTT ATTCTATTTT AGCCCTCTAAA TTAAGAAAAC
551  TAAAACTCTA TTTTAGTTTT TTTATTTAAT AATTTAGATA TAAAATAGAA
601  TAAAATAAAG TGACTAAAAA TTAAACAAAT ACCCTTAAG AAATTAAAAA
651  AACTAAGGAA ACATTTTCT TGTTTCGAGT AGATAATGCC AGCCTGTTAA
701  ACGCCGTCGA CGAGTCTAAC GGACACCAAC CAGCGAACCA GCAGCGTCGC
751  GTCGGGCAA GCGAAGCAGA CGGCACGGCA TCTCGTCGC TGCCTCTGGA
801  CCCCTCTCGA GAGTTCCGCT CCACCGTTGG ACTTGCTCCG CTGTCGGCAT
851  CCAGAAATTG CGTGGCGGAG CGGCAGACGT GAGCCGGCAC GGCAGGCGGC
901  CTCCTCCTCC TCTCACGGCA CGGCAGCTAC GGGGGATTCC TTTCCCACCG
951  CTCCTTGCT TTCCCTTCCT CGCCCGCCGT AATAAATAGA CACCCCCTCC
1001 ACACCCTCTT TCCCAACCT CGTGTGTTC GGAGCGCACA CACACACAAC
1051 CAGATCTCCC CCAAATCCAC CCGTCGGCAC CTCCGCTTCA AGGTACGCCG
1101 CTCGTCCTCC CCCCCCCCC CTCTCTACCT TCTCTAGATC GGCGTTCCGG
1151 TCCATGCATG GTTAGGGCCC GGTAGTTCTA CTTCTGTTCA TGTTTGTGTT
1201 AGATCCGTGT TTGTGTTAGA TCCGTGCTGC TAGCGTTCGT ACACGGATGC
1251 GACCTGTACG TCAGACACGT TCTGATTGCT AACTTGCCAG TGTTTCTCTT
1301 TGGGGAATCC TGGGATGGCT CTAGCCGTTC CGCAGACGGG ATCGATTTCA
1351 TGATTTTTTT TGTTTCGTTG GGTTTGCCCT GGTTTGCCCT TTTCCTTTAT
1401 TTCAATATAT GCCGTGCACT TGTTTGTCGG GTCATCTTTT CATGCTTTTT
1451 TTTGTCTTGG TTGTGATGAT GTGGTCTGGT TGGGCGGTCG TTCTAGATCG
1501 GAGTAGAATT CTGTTTCAAA CTACCTGGTG GATTTATTAA TTTTGGATCT
1551 GTATGTGTGT GCCATACATA TTCATAGTTA CGAATTGAAG ATGATGGATG
1601 GAAATATCGA TCTAGGATAG GTATACATGT TGATGCGGGT TTTACTGATG
1651 CATATACAGA GATGCTTTTT GTTCGCTTGG TTGTGATGAT GTGGTGTGGT
```

FIG 5B CONT.

```
1701 TGGGCGGTCG TTCATTCGTT CTAGATCGGA GTAGAATACT GTTTCAAACT
1751 ACCTGGTGTA TTTATTAATT TGGAACTGT ATGTGTGT CATACATCTT
1801 CATAGTTACG AGTTTAAGAT GGATGGAAAT ATCGATCTAG GATAGGTATA
1851 CATGTTGATG TGGGTTTTAC TGATGCATAT ACATGATGGC ATATGCAGCA
1901 TCTATTCATA TGCTCTAACC TTGAGTACCT ATCTATTATA ATAAACAAGT
1951 ATGTTTTATA ATTATTTGA TCTTGATATA CTTGGATGAT GGCATATGCA
2001 GCAGCTATAT GTGGATTTT TTAGCCCTGC CTTCATACGC TATTTATTTG
2051 CTTGGTACTG TTTCTTTTGT CGATGCTCAC CCTGTTGTTT GGTGTTACTT
2101 CTGCAGGGTA CCCCCGGGGT CGACCATGGT AAGGGCAGC CACCACCACC
2151 ACCACCACAT GGTCCGTCCT GTAGAAACCC CAACCCGTGA AATCAAAAAA
2201 CTCGACGGCC TGTGGGCATT CAGTCTGGAT CGCGAAAACT GTGGAATTGA
2251 TCAGCGTTGG TGGGAAAGCG CGTTACAAGA AAGCCGGGCA ATTGCTGTGC
2301 CAGGCAGTTT TAACGATCAG TTCGCCGATG CAGATATTCG TAATTATGCG
2351 GGCAACGTCT GGTATCAGCG CGAAGTCTTT ATACCGAAAG GTTGGGCAGG
2401 CCAGCGTATC GTGCTGCGTT TCGATGCGGT CACTCATTAC GGCAAAGTGT
2451 GGGTCAATAA TCAGGAAGTG ATGGAGCATC AGGGCGGCTA TACGCCATTT
2501 GAAGCCGATG TCACGCCGTA TGTTATTGCC GGGAAAAGTG TACGTATCAC
2551 CGTTTGTGTG AACAACGAAC TGAACTGGCA GACTATCCCG CCATGATTTC
2601 TGATTACCGA CGAAAACGGC AAGAAAAAGC AGTCTTACTT CCACGCCGAA
2651 TTTAACTATG CCGGAATCCA TCGCAGCGTA ATGCTCTACA CCACGCCGAA
2701 CACCTGGGTG GACGATATCA CCGTGGTGAC GCATGTCGCG CAAGACTGTA
2751 ACCACGCGTC TGTTGACTGG CAGGTGGTGG CCAATGGTGA TGTCAGCGTT
2801 GAACTGCGTG ATGCGGATCA ACAGGTGGTT GCAACTGGAC AAGGCACTAG
2851 CGGGACTTTG CAAGTGGTGA ATCCGCACCT CTGGCAACCG GGTGAAGGTT
2901 ATCTCTATGA ACTGTGCGTC ACAGCCAAAA GCCAGACAGA GTGTGATATC
2951 TACCCGCTTC GCGTCGGCAT CCGGTCAGTG GCAGTGAAGG GCGAACAGTT
3001 CCTGATTAAC CACAAACCGT TCTACTTTAC TGGCTTTGGT CGTCATGAAG
3051 ATGCGGACTT ACGTGGCAAA GGATTCGATA ACGTGCTGAT GGTGCACGAC
3101 CACGCATTAA TGGACTGGAT TGGGGCCAAC TCCTACCGTA CCTCGGCATTA
3151 CCCTTACGCT GAAGAGATGC TCGACTGGGC AGATGAACAT GGCATCGTGG
3201 TGATTGATGA AACTGCTGCT GTCGGCTTTA ACCTCTCTTT AGGCATTGGT
```

FIG 5B CONT.

```
3251 TTCGAAGCGG GCAACAAGCC GAAAGAACTG TACAGCGAAG AGGCAGTCAA
3301 CGGGGAAACT CAGCAAGCGC ACTTACAGGC GATTAAAGAG CTGATAGCGC
3351 GTGACAAAAA CCACCAAGC GTGGTGATGT GGAGTATTGC CAACGAACCG
3401 GATACCCGTC CGCAAGTGCA CGGGAATATT TCGCCACTGG CGGAAGCAAC
3451 GCGTAAACTC GACCCGACGC GTCCGATCAC CTGCGTCAAT GTAATGTTCT
3501 GCGACGCTCA CACCGATACC ATCAGCGATC TCTTTGATGT GCTGTGCCTG
3551 AACCGTTATT ACGGATGGTA TGTCCAAAGC GGCGATTTGG AAACGGCAGA
3601 GAAGGTACTG GAAAAAGAAC TTCTGGCCTG GCAGGAGAAA CTGCATCAGC
3651 CGATTATCAT CACCGAATAC GGCGTGGATA CGTTAGCCGG GCTGCACTCA
3701 ATGTACACCG ACATGTGGAG TGAAGAGTAT CAGTGTGCAT GGCTGGATAT
3751 GTATCACCGC GTCTTTGATC GCGTCAGCGC CGTCGTCGGT GAACAGGTAT
3801 GGAATTTGCG CGATTTTGCG ACCTCGCAAG GCATATTGCG CGTTGGCGGT
3851 AACAAGAAAG GGATCTTCAC TCGCGACCGC AAACCGAAGT CGGCGGCTTT
3901 TCTGCTGCAA AAACGCTGGA CTGGCATGAA CTTCGGTGAA AAACCGCAGC
3951 AGGGAGGCAA ACAATGATAA TGAGCTCGTT TAAACTGAGG GCACTGAAGT
4001 CGCTTGATGT GCTGAATTGT TTGTGATGTT GGTGGCGTAT TTTGTTTAAA
4051 TAAGTAAGCA TGGCTGTGAT TTTATCATAT GATCGATCTT TGGGGTTTTA
4101 TTTAACACAT TGTAAAATGT GTATCTATTA ATAACTCAAT GTATAAGATG
4151 TGTTCATTCT TCGGTTGCCA TAGATCTGCT TATTTGACCT GTGATGTTTT
4201 GACTCCAAAA ACCAAAATCA CAACTCAATA AACTCATGGA ATATGTCCAC
4251 CTGTTTCTTG AAGAGTTCAT CTACCATTCC AGTTGGCATT TATCAGTGTT
4301 GCAGCGGCGC TGTGCTTTGT AACATAACAA TTGTTACGGC ATATATCCAA
4351 CGGCCGGCCT AGCTAGCCAC GGTGGCCAGA TCCACTAGTT CTAGAGCGGC
4401 CGCTTAATTC ACTGGCCGTC GTTTTACAAC GTCGTGACTG GGAAAACCCT
4451 GGCGTTACCC AACTTAATCG CCTTGCAGCA CATCCCCCTT TCGCCAGCTG
4501 GCGTAATAGC GAAGAGGCCC GCACCGATCG CCCTTCCCAA CAGTTGCGCA
4551 GCCTGAATGG CGAATGGCGC CTGATGCGGT ATTTTCTCCT TACGCATCTG
4601 TGCGGTATTT CACACCGCAT ATGGTGCACT CTCAGTACAA TCTGCTCTGA
4651 TGCCGCATAG TTAAGCCAGC CCCGACACCC GCCAACACCC GCTGACGCGC
4701 CCTGACGGGC TTGTCTGCTC CCGGCATCCG CTTACAGACA AGCTGTGACC
4751 GTCTCCGGGA GCTGCATGTG TCAGAGGTTT TCACCGTCAT CACCGAAACG
```

FIG 5B CONT.

```
4801  CGCGAGACGA  AAGGGCCTCG  TGATACGCCT  ATTTTTATAG  GTTAATGTCA
4851  TGATAATAAT  GGTTTCTTAG  ACGTCAGGTG  GCACTTTTCG  GGGAAATGTG
4901  CGCGAACCC   CTATTTGTTT  ATTTTTCTAA  ATACATTCAA  ATATGTATCC
4951  GCTCATGAGA  CAATAACCCT  GATAAATGCT  TCAATAATAT  TGAAAAAGGA
5001  AGAGTATGAG  TATTCAACAT  TTCCGTGTCG  CCCTTATTCC  CTTTTTTGCG
5051  GCATTTTGCC  TTCCTGTTTT  TGCTCACCCA  GAAACGCTGG  TGAAAGTAAA
5101  AGATGCTGAA  GATCAGTTGG  GTGCACGAGT  GGGTTACATC  GAACTGGATC
5151  TCAACAGCGG  TAAGATCCTT  GAGAGTTTTC  GCCCCGAAGA  ACGTTTTCCA
5201  ATGATGAGCA  CTTTTAAAGT  TCTGCTATGT  GGCGCGGTAT  TATCCCGTAT
5251  TGACGCCGGG  CAAGAGCAAC  TCGGTCGCCG  CATACACTAT  TCTCAGAATG
5301  ACTTGGTTGA  GTACTCACCA  GTCACAGAAA  AGCATCTTAC  GGATGGCATG
5351  ACAGTAAGAG  AATTATGCAG  TGCTGCCATA  ACCATGAGTG  ATAACACTGC
5401  GGCCAACTTA  CTTCTGACAA  CGATCGGAGG  ACCGAAGGAG  CTAACCGCTT
5451  TTTTGCACAA  CATGGGGGAT  CATGTAACTC  GCCTTGATCG  TTGGGAACCG
5501  GAGCTGAATG  AAGCCATACC  AAACGACGAG  CGTGACACCA  CGATGCCTGT
5551  AGCAATGGCA  ACAACGTTGC  GCAAACTATT  AACTGGCGAA  CTACTTACTC
5601  TAGCTTCCCG  GCAACAATTA  ATAGACTGGA  TGGAGGCGGA  TAAAGTTGCA
5651  GGACCACTTC  TGCGCTCGGC  CCTTCCGGCT  GGCTGGTTTA  TTGCTGATAA
5701  ATCTGGAGCC  GGTGAGCGTG  GGTCTCGCGG  TATCATTGCA  GCACTGGGGC
5751  CAGATGGTAA  GCCCTCCCGT  ATCGTAGTTA  TCTACACGAC  GGGGAGTCAG
5801  GCAACTATGG  ATGAACGAAA  TAGACAGATC  GCTGAGATAG  GTGCCTCACT
5851  GATTAAGCAT  TGGTAACTGT  CAGACCAAGT  TTACTCATAT  ATACTTTAGA
5901  TTGATTTAAA  ACTTCATTTT  TAATTTAAAA  GGATCTAGGT  GAAGATCCTT
5951  TTTGATAATC  TCATGACCAA  AATCCCTTAA  CGTGAGTTTT  CGTTCCACTG
6001  AGCGTCAGAC  CCCGTAGAAA  AGATCAAAGG  ATCTTCTTGA  GATCCTTTTT
6051  TTCTGCGCGT  AATCTGCTGC  TTGCAAACAA  AAAAACCACC  GCTACCAGCG
6101  GTGGTTTGTT  TGCCGGATCA  AGAGCTACCA  ACTCTTTTTC  CGAAGGTAAC
6151  TGGCTTCAGC  AGAGCGCAGA  TACCAAATAC  TGTCCTTCTA  GTGTAGCCGT
6201  AGTTAGGCCA  CCACTTCAAG  AACTCTGTAG  CACCGCCTAC  ATACCTCGCT
6251  CTGCTAATCC  TGTTACCAGT  GGCTGCTGCC  AGTGGCGATA  AGTCGTGTCT
6301  TACCGGGTTG  GACTCAAGAC  GATAGTTACC  GGATAAGGCG  CAGCGGTCGG
```

FIG 5B CONT.

```
6351  GCTGAACGGG  GGGTTCGTGC  ACACAGCCCA  GCTTGGAGCG  AACGACCTAC
6401  ACCGAACTGA  GATACCTACA  GCGTGAGCAT  TGAGAAAGCG  CCACGCTTCC
6451  CGAAGGGAGA  AAGCCGGACA  GGTATCCGGT  AAGCGGCAGG  GTCGGAACAG
6501  GAGAGCGCAC  GAGGGAGCTT  CCAGGGGGAA  ACGCCTGGTA  TCTTTATAGT
6551  CCTGTCGGGT  TTCGCCACCT  CTGACTTGAG  CGTCGATTTT  TGTGATGCTC
6601  GTCAGGGGGG  CGGAGCCTAT  GGAAAAACGC  CAGCAACGCG  GCCTTTTTAC
6651  GGTTCCTGGC  CTTTTGCTGG  CCTTTTGCTC  ACATGTTCTT  TCCTGCGTTA
6701  TCCCCTGATT  CTGTGGATAA  CCGTATTACC  GCCTTTGAGT  GAGCTGATAC
6751  CGCTCGCCGC  AGCCGAACGA  CCGAGCGCAG  CGAGTCAGTG  AGCGAGGAAG
6801  CGGAAGAGCG  CCCAATACGC  AAACCGCCTC  TCCCCGCGCG  TTGGCCGATT
6851  CATTAATGCA  GCTGGCACGA  CAGGTTTCCC  GACTGGAAAG  CGGGCAGTGA
6901  GCGCAACGCA  ATTAATGTGA  GTTAGCTCAC  TCATTAGGCA  CCCCAGGCTT
6951  TACACTTTAT  GCTTCCGGCT  CGTATGTTGT  GTGGAATTGT  GAGCGGATAA
7001  CAATTTCACA  CAGGAAACAG  CTATGAC
```

FIG 5B CONT.

| Sequence | Feature |
|---|---|
| 1-38 Linker | CCTGCAGATCCCCGGGGATCCTCTAGAGTCGACCTGCA |
| 39-2028 | Maize Ubiquitin 1 promoter |
| 2029-2047 Linker | GGGTACCCCCGGGGTCGAC |
| 2048-3695 | GNT III v.2 plus TAGGTTT |
| 2462 | C to replace G as reported in original sequence |
| 3696-3699 PmeI | AAAC |
| 3700-4064 | Maize Per 5 3'UTR |
| 4065-6818 | pUC19 backbone |
| 4259-4264 | TGCGCA FspI |
| 4720-5580 | Ampicillin Resistance gene |
| 5282-5287 | TGCGCA FspI |

```
                       BamHI
                       ~~~~~~~
  1  CCTGCAGATC CCCGGGGATC CTCTAGAGTC GACCTGCAGT
     GCAGCGTGAC CCGGTCGTGC CCCTCTCTAG AGATAATGAG
     CATTGCATGT CTAAGTTATA
101  AAAAATTACC ACATATTTTT TTTGTCACAC TTGTTTGAAG
     TGCAGTTTAT CTATCTTTAT ACATATATTT AAACTTTAAT
     CTACGAATAA TATAATCTAT
201  AGTACTACAA TAATATCAGT GTTTTAGAGA ATCATATAAA
     TGAACAGTTA GACATGGTCT AAAGGACAAT TGAGTATTTT
     GACAACAGGA CTCTACAGTT
301  TTATCTTTTT AGTGTGCATG TGTTCTCCTT TTTTTTTGCA
     AATAGCTTCA CCTATATAAT ACTTCATCCA TTTTATTAGT
     ACATCCATTT AGGGTTTAGG
401  GTTAATGGTT TTTATAGACT AATTTTTTTA GTACATCTAT
     TTTATTCTAT TTTAGCCTCT AAATTAAGAA AACTAAAACT
     CTATTTTAGT TTTTTTATTT
501  AATAATTTAG ATATAAAATA GAATAAAATA AAGTGACTAA
     AAATTAAACA AATACCCTTT AAGAAATTAA AAAAACTAAG
     GAAACATTTT TCTTGTTTCG
601  AGTAGATAAT GCCAGCCTGT TAAACGCCGT CGACGAGTCT
     AACGGACACC AACCAGCGAA CCAGCAGCGT CGCGTCGGGC
     CAAGCGAAGC AGACGGCACG
701  GCATCTCTGT CGCTGCCTCT GGACCCCTCT CGAGAGTTCC
     GCTCCACCGT TGGACTTGCT CCGCTGTCGG CATCCAGAAA
     TTGCGTGGCG GAGCGGCAGA
801  CGTGAGCCGG CACGGCAGGC GGCCTCCTCC TCCTCTCACG
     GCACGGCAGC TACGGGGGAT TCCTTTCCCA CCGCTCCTTC
     GCTTTCCCTT CCTCGCCCGC
```

FIG 6B

```
 901  CGTAATAAAT AGACACCCCC TCCACACCCT CTTTCCCCAA
      CCTCGTGTTG TTCGGAGCGC ACACACACAC AACCAGATCT
      CCCCCAAATC CACCCGTCGG
1001  CACCTCCGCT TCAAGGTACG CCGCTCGTCC TCCCCCCCCC
      CCCCTCTCTA CCTTCTCTAG ATCGGCGTTC CGGTCCATGC
      ATGGTTAGGG CCCGGTAGTT
1101  CTACTTCTGT TCATGTTTGT GTTAGATCCG TGTTTGTGTT
      AGATCCGTGC TGCTAGCGTT CGTACACGGA TGCGACCTGT
      ACGTCAGACA CGTTCTGATT
1201  GCTAACTTGC CAGTGTTTCT CTTTGGGGAA TCCTGGGATG
      GCTCTAGCCG TTCCGCAGAC GGGATCGATT TCATGATTTT
      TTTTGTTTCG TTGCATAGGG
1301  TTTGGTTTGC CCTTTTCCTT TATTTCAATA TATGCCGTGC
      ACTTGTTTGT CGGGTCATCT TTTCATGCTT TTTTTTGTCT
      TGGTTGTGAT GATGTGGTCT
1401  GGTTGGGCGG TCGTTCTAGA TCGGAGTAGA ATTCTGTTTC
      AAACTACCTG GTGGATTTAT TAATTTTGGA TCTGTATGTG
      TGTGCCATAC ATATTCATAG
1501  TTACGAATTG AAGATGATGG ATGGAAATAT CGATCTAGGA
      TAGGTATACA TGTTGATGCG GGTTTTACTG ATGCATATAC
      AGAGATGCTT TTTGTTCGCT
1601  TGGTTGTGAT GATGTGGTGT GGTTGGGCGG TCGTTCATTC
      GTTCTAGATC GGAGTAGAAT ACTGTTTCAA ACTACCTGGT
      GTATTTATTA ATTTTGGAAC
1701  TGTATGTGTG TGTCATACAT CTTCATAGTT ACGAGTTTAA
      GATGGATGGA AATATCGATC TAGGATAGGT ATACATGTTG
      ATGTGGGTTT TACTGATGCA
1801  TATACATGAT GGCATATGCA GCATCTATTC ATATGCTCTA
      ACCTTGAGTA CCTATCTATT ATAATAAACA AGTATGTTTT
      ATAATTATTT TGATCTTGAT
1901  ATACTTGGAT GATGGCATAT GCAGCAGCTA TATGTGGATT
      TTTTTAGCCC TGCCTTCATA CGCTATTTAT TTGCTTGGTA
      CTGTTTCTTT TGTCGATGCT

NcoI
      FseI

~~~~~~~
      ~~~~~~~~~~

2001  CACCCTGTTG TTTGGTGTTA CTTCTGCAGG GTACCCCCGG
      GGTCGACCAT GGTGATGAGA CGCTACAAGC TCTTTCTCAT
      GTTCTGTATG GCCGGCCTGT
2101  GCCTCATCTC CTTCCTGCAC TTCTTCAAGA CCCTGTCCTA
      TGTCACCTTC CCCCGAGAAC TGGCCTCCCT CAGCCCTAAC
      CTGGTGTCCA GCTTTTTCTG
2201  GAACAATGCC CCGGTCACGC CCCAGGCCAG CCCCGAGCCA
      GGAGGCCCTG ACCTGCTGCG TACCCCACTC TACTCCCACT
      CGCCCCTGCT GCAGCCGCTG
```

FIG 6B CONT.

```
                      SacI
        FspI          ~~~~~~
        ~~~~~~
2301  CCGCCCAGCA AGGCGGCCGA GGAGCTCCAC CGGGTGGACT
      TGGTGCTGCC CGAGGACACC ACCGAGTATT TCGTGCGCAC
      CAAGGCCGGC GGCGTCTGCT
2401  TCAAACCCGG CACCAAGATG CTGGAGAGGC CCCCCCCGGG
      ACGGCCGGAG GAGAAGCCTG AGGGGGCCAA CGGCTCCTCG
      GCCCGGCGGC CACCCCGGTA
2501  CCTCCTGAGC GCCCGGGAGC GCACGGGGGG CCGAGGCGCC
      CGGCGCAAGT GGGTGGAGTG CGTGTGCCTG CCCGGCTGGC
      ACGGACCCAG CTGCGGCGTG
2601  CCCACTGTGG TGCAGTACTC CAACCTGCCC ACCAAGGAGC
      GGCTGGTGCC CAGGGAGGTG CCGCGCCGCG TCATCAACGC
      CATCAACGTC AACCACGAGT

NotI
      ~~~~~~~~
2701  TCGACCTGCT GGACGTGCGC TTCCACGAGC TGGGCGACGT
      GGTGGACGCC TTTGTGGTGT GCGAGTCCAA CTTCACGGCT
      TATGGGGAGC CGCGGCCGCT
2801  CAAGTTCCGG GAGATGCTGA CCAATGGCAC CTTCGAGTAC
      ATCCGCCACA AGGTGCTCTA TGTCTTCCTG GACCACTTCC
      CGCCCGGCGG CCGGCAGGAC
                                   FspI
      FspI                         ~~~~~~
      ~~~~~~
2901  GGCTGGATCG CCGACGACTA CCTGCGCACC TTCCTCACCC
      AGGACGGCGT CTCGCGGCTG CGCAACCTGC GGCCCGACGA
      CGTCTTCATC ATTGACGATG

FspI
      ~~~~~~
3001  CGGACGAGAT CCCGGCCCGT GACGGCGTCC TTTTCCTCAA
      GCTCTACGAT GGCTGGACCG AGCCCTTCGC CTTCCACATG
      CGCAAGTCGC TCTACGGCTT
3101  CTTCTGGAAG CAGCCGGGCA CCCTGGAGGT GGTGTCAGGC
      TGCACGGTGG ACATGCTGCA GGCAGTGTAT GGGCTGGACG
      GCATCCGCCT GCGCCGCCGC
3201  CAGTACTACA CCATGCCCAA CTTCAGACAG TATGAGAACC
      GCACCGGCCA CATCCTGGTG CAGTGGTCGC TGGGCAGCCC
      CCTGCACTTC GCCGGCTGGC
```

FIG 6B CONT.

3301 ACTGCTCCTG GTGCTTCACG CCCGAGGGCA TCTACTTCAA
     GCTCGTGTCC GCCCAGAATG GCGACTTCCC ACGCTGGGGT
     GACTACGAGG ACAAGCGGGA
3401 CCTGAACTAC ATCCGCGGCC TGATCCGCAC CGGGGGCTGG
     TTCGACGGCA CGCAGCAGGA GTACCCGCCT GCAGACCCCA
     GCGAGCACAT GTATGCGCCC
3501 AAGTACCTGC TGAAGAACTA CGACCGGTTC CACTACCTGC
     TGGACAACCC CTACCAGGAG CCCAGGAGCA CGGCGGCGGG
     CGGGTGGCGC CACAGGGGTC

BamHI      PmeI

~~~~~~     ~~~~~~~~

3601 CCGAGGGAAG GCCGCCCGCC CGGGGCAAAC TGGACGAGGC
     GGAAGTCGAA CAAAAACTCA TCTCAGAAGA GGATCTGAAT
     TAGGATCCTA GGTTTAAACT
3701 GAGGGCACTG AAGTCGCTTG ATGTGCTGAA TTGTTTGTGA
     TGTTGGTGGC GTATTTTGTT TAAATAAGTA AGCATGGCTG
     TGATTTTATC ATATGATCGA
3801 TCTTTGGGGT TTTATTTAAC ACATTGTAAA ATGTGTATCT
     ATTAATAACT CAATGTATAA GATGTGTTCA TTCTTCGGTT
     GCCATAGATC TGCTTATTTG
3901 ACCTGTGATG TTTTGACTCC AAAAACCAAA ATCACAACTC
     AATAAACTCA TGGAATATGT CCACCTGTTT CTTGAAGAGT
     TCATCTACCA TTCCAGTTGG

FseI

~~~~~~~~~

4001 CATTTATCAG TGTTGCAGCG GCGCTGTGCT TTGTAACATA
     ACAATTGTTC ACGGCATATA TCCACGGCCG GCCTAGCTAG
     CCACGGTGGC CAGATCCACT
              NotI
              ~~~~~~~~~
4101 AGTTCTAGAG CGGCCGCTTA ATTCACTGGC CGTCGTTTTA
     CAACGTCGTG ACTGGGAAAA CCCTGGCGTT ACCCAACTTA
     ATCGCCTTGC AGCACATCCC

FspI

~~~~~~~

4201 CCTTTCGCCA GCTGGCGTAA TAGCGAAGAG GCCCGCACCG
     ATCGCCCTTC CCAACAGTTG CGCAGCCTGA ATGGCGAATG
     GCGCCTGATG CGGTATTTTC
4301 TCCTTACGCA TCTGTGCGGT ATTTCACACC GCATATGGTG
     CACTCTCAGT ACAATCTGCT CTGATGCCGC ATAGTTAAGC
     CAGCCCCGAC ACCCGCCAAC

FIG 6B CONT.

```
4401  ACCCGCTGAC GCGCCCTGAC GGGCTTGTCT GCTCCCGGCA
      TCCGCTTACA GACAAGCTGT GACCGTCTCC GGGAGCTGCA
      TGTGTCAGAG GTTTTCACCG
4501  TCATCACCGA AACGCGCGAG ACGAAAGGGC CTCGTGATAC
      GCCTATTTTT ATAGGTTAAT GTCATGATAA TAATGGTTTC
      TTAGACGTCA GGTGGCACTT
4601  TTCGGGAAA TGTGCGCGGA ACCCCTATTT GTTTATTTTT
      CTAAATACAT TCAAATATGT ATCCGCTCAT GAGACAATAA
      CCCTGATAAA TGCTTCAATA
4701  ATATTGAAAA AGGAAGAGTA TGAGTATTCA ACATTTCCGT
      GTCGCCCTTA TTCCCTTTTT TGCGGCATTT TGCCTTCCTG
      TTTTTGCTCA CCCAGAAACG
4801  CTGGTGAAAG TAAAAGATGC TGAAGATCAG TTGGGTGCAC
      GAGTGGGTTA CATCGAACTG GATCTCAACA GCGGTAAGAT
      CCTTGAGAGT TTTCGCCCCG
4901  AAGAACGTTT TCCAATGATG AGCACTTTTA AAGTTCTGCT
      ATGTGGCGCG GTATTATCCC GTATTGACGC CGGGCAAGAG
      CAACTCGGTC GCCGCATACA
5001  CTATTCTCAG AATGACTTGG TTGAGTACTC ACCAGTCACA
      GAAAAGCATC TTACGGATGG CATGACAGTA AGAGAATTAT
      GCAGTGCTGC CATAACCATG
5101  AGTGATAACA CTGCGGCCAA CTTACTTCTG ACAACGATCG
      GAGGACCGAA GGAGCTAACC GCTTTTTTGC ACAACATGGG
      GGATCATGTA ACTCGCCTTG

FspI
      ~~~~~~

5201  ATCGTTGGGA ACCGGAGCTG AATGAAGCCA TACCAAACGA
      CGAGCGTGAC ACCACGATGC CTGTAGCAAT GGCAACAACG
      TTGCGCAAAC TATTAACTGG
5301  CGAACTACTT ACTCTAGCTT CCCGGCAACA ATTAATAGAC
      TGGATGGAGG CGGATAAAGT TGCAGGACCA CTTCTGCGCT
      CGGCCCTTCC GGCTGGCTGG
5401  TTTATTGCTG ATAAATCTGG AGCCGGTGAG CGTGGGTCTC
      GCGGTATCAT TGCAGCACTG GGGCCAGATG GTAAGCCCTC
      CCGTATCGTA GTTATCTACA
5501  CGACGGGGAG TCAGGCAACT ATGGATGAAC GAAATAGACA
      GATCGCTGAG ATAGGTGCCT CACTGATTAA GCATTGGTAA
      CTGTCAGACC AAGTTTACTC
5601  ATATATACTT TAGATTGATT TAAAACTTCA TTTTTAATTT
      AAAAGGATCT AGGTGAAGAT CCTTTTTGAT AATCTCATGA
      CCAAAATCCC TTAACGTGAG
5701  TTTTCGTTCC ACTGAGCGTC AGACCCCGTA GAAAAGATCA
      AAGGATCTTC TTGAGATCCT TTTTTTCTGC GCGTAATCTG
      CTGCTTGCAA ACAAAAAAAC
```

FIG 6B CONT.

5801 CACCGCTACC AGCGGTGGTT TGTTTGCCGG ATCAAGAGCT
     ACCAACTCTT TTTCCGAAGG TAACTGGCTT CAGCAGAGCG
     CAGATACCAA ATACTGTCCT
5901 TCTAGTGTAG CCGTAGTTAG GCCACCACTT CAAGAACTCT
     GTAGCACCGC CTACATACCT CGCTCTGCTA ATCCTGTTAC
     CAGTGGCTGC TGCCAGTGGC
6001 GATAAGTCGT GTCTTACCGG GTTGGACTCA AGACGATAGT
     TACCGGATAA GGCGCAGCGG TCGGGCTGAA CGGGGGGTTC
     GTGCACACAG CCCAGCTTGG
6101 AGCGAACGAC CTACACCGAA CTGAGATACC TACAGCGTGA
     GCATTGAGAA AGCGCCACGC TTCCCGAAGG GAGAAAGGCG
     GACAGGTATC CGGTAAGCGG
6201 CAGGGTCGGA ACAGGAGAGC GCACGAGGGA GCTTCCAGGG
     GGAAACGCCT GGTATCTTTA TAGTCCTGTC GGGTTTCGCC
     ACCTCTGACT TGAGCGTCGA
6301 TTTTTGTGAT GCTCGTCAGG GGGGCGGAGC CTATGGAAAA
     ACGCCAGCAA CGCGGCCTTT TTACGGTTCC TGGCCTTTTG
     CTGGCCTTTT GCTCACATGT
6401 TCTTTCCTGC GTTATCCCCT GATTCTGTGG ATAACCGTAT
     TACCGCCTTT GAGTGAGCTG ATACCGCTCG CCGCAGCCGA
     ACGACCGAGC GCAGCGAGTC
6501 AGTGAGCGAG GAAGCGGAAG AGCGCCCAAT ACGCAAACCG
     CCTCTCCCCG CGCGTTGGCC GATTCATTAA TGCAGCTGGC
     ACGACAGGTT TCCCGACTGG
6601 AAAGCGGGCA GTGAGCGCAA CGCAATTAAT GTGAGTTAGC
     TCACTCATTA GGCACCCCAG GCTTTACACT TTATGCTTCC
     GGCTCGTATG TTGTGTGGAA

NotI
     ~~~~~~~~~
6701 TTGTGAGCGG ATAACAATTT CACACAGGAA ACAGCTATGA
     CCATGATTAC GCCAAGCTAG CGGCCGCATT CCCGGGAAGC
     TAGGCCACCG TGGCCCGCCT
             HindIII
             ~~~~~~~
6801 GCAGGGGAAG CTTGCATG

FIG 6B CONT.

Plasmid pDAB8504 (7545 bp)
Description: Cloning vector with Rb7 MARs (inverted orientation) flanking a multiple cloning site and the rice actin/PAT/lipase selectable marker cassette

| Nucleotide start | Nucleotide end | Sequence Feature |
|---|---|---|
| 1 | 1166 | Tobacco Rb7 MARs |
| 1167 | 1304 | Linker Sequence with multiple cloning site: TGGCCACCGCTTAATTAAGGCGCGCCATGCCCGGGCAAGCGGCCGCTTAATTAAATTTAAATGTTTAAACTAGGAAATCCAAGCTTGGGCTGCAGGTCAATCCCATTGCTTTTGAAGCAGCTCAACATTGATCTCTTT |
| 1305 | 2701 | Rice actin promoter with intron |
| 2235 | 2696 | Rice actin intron |
| 2702 | 2703 | CC |
| 2704 | 3258 | PAT gene (phosphinothricin acyl transferase) |
| 3259 | 3272 | Linker sequence: GGTACCCTGAGCTC |
| 3273 | 3629 | Maize lipase 3' UTR |
| 3630 | 3670 | Linker sequence: GAATTCATATTTCCTCCTGCAGGGTTTAAACTTGCCGTGGC |
| 3671 | 4836 | Tobacco Rb7 MAR (complementary) |
| 4837 | 4857 | Linker sequence: CGGCCCACTAGTCACCGGTGT |
| 4858 | 5103 | Puc19 |
| 5104 | 5130 | Linker sequence: GCGCACGCTGCGCACGCTGCGCACGCT |
| 5130 | 7523 | Puc19 |
| 7524 | 7545 | Linker sequence: ACACCGGTGTGATCATGGGCCG |

Sequence
```
  1    CGATTAAAAA TCTCAATTAT ATTTGGTCTA ATTTAGTTTG GTATTGAGTA
 51    AAACAAATTC GAACCAAACC AAAATATAAA TATATAGTTT TTATATATAT
101    GCCTTTAAGA CTTTTTATAG AATTTTCTTT AAAAAATATC TAGAAATATT
151    TGCGACTCTT CTGGCATGTA ATATTTCGTT AAATATGAAG TGCTCCATTT
201    TTATTAACTT TAAATAATTG GTTGTACGAT CACTTTCTTA TCAAGTGTTA
251    CTAAAATGCG TCAATCTCTT TGTTCTTCCA TATTCATATG TCAAAACCTA
301    TCAAAATTCT TATATATCTT TTTCGAATTT GAAGTGAAAT TTCGATAATT
351    TAAAATTAAA TAGAACATAT CATTATTTAG GTATCATATT GATTTTTATA
401    CTTAATTACT AAATTTGGTT AACTTTGAAA GTGTACATCA ACGAAAAATT
451    AGTCAAACGA CTAAAATAAA TAAATATCAT GTGTTATTAA GAAAATTCTC
501    CTATAAGAAT ATTTTAATAG ATCATATGTT TGTAAAAAAA ATTAATTTTT
551    ACTAACACAT ATATTTACTT ATCAAAAATT TGACAAAGTA AGATTAAAAT
601    AATATTCATC TAACAAAAAA AAAACCAGAA AATGCTGAAA ACCCGGCAAA
651    ACCGAACCAA TCCAAACCGA TATAGTTGGT TTGGTTTGAT TTTGATATAA
701    ACCGAACCAA CTCGGTCCAT TTGCACCCCT AATCATAATA GCTTTAATAT
751    TTCAAGATAT TATTAAGTTA ACGTTGTCAA TATCCTGGAA ATTTTGCAAA
801    ATGAATCAAG CCTATATGGC TGTAATATGA ATTAAAAGC AGCTCGATGT
851    GGTGGTAATA TGTAATTTAC TTGATTCTAA AAAAATATCC CAAGTATTAA
```

FIG 7B

```
 901   TAATTTCTGC TAGGAAGAAG GTTAGCTACG ATTTACAGCA AAGCCAGAAT
 951   ACAATGAACC ATAAAGTGAT TGAAGCTCGA AATATACGAA GGAACAAATA
1001   TTTTTAAAAA AATACGCAAT GACTTGGAAC AAAAGAAAGT GATATATTTT
1051   TTGTTCTTAA ACAAGCATCC CCTCTAAAGA ATGGCAGTTT TCCTTTGCAT
1101   GTAACTATTA TGCTCCCTTC GTTACAAAAA TTTTGGACTA CTATTGGGAA
1151   CTTCTTCTGA AAATAGTGGC CACCGCTTAA TTAAGGCGCG CCATGCCCGG
1201   GCAAGCGGCC GCTTAATTAA ATTTAAATGT TTAAACTAGG AAATCCAAGC
1251   TTGGGCTGCA GGTCAATCCC ATTGCTTTTG AAGCAGCTCA ACATTGATCT
1301   CTTTCTCGAG GTCATTCATA TGCTTGAGAA GAGAGTCGGG ATAGTCCAAA
1351   ATAAAACAAA GGTAAGATTA CCTGGTCAAA AGTGAAAACA TCAGTTAAAA
1401   GGTGGTATAA AGTAAAATAT CGGTAATAAA AGGTGGCCCA AAGTGAAATT
1451   TACTCTTTTC TACTATTATA AAAATTGAGG ATGTTTTTGT CGGTACTTTG
1501   ATACGTCATT TTTGTATGAA TTGGTTTTTA AGTTTATTCG CTTTTGGAAA
1551   TGCATATCTG TATTTGAGTC GGGTTTTAAG TTCGTTTGCT TTTGTAAATA
1601   CAGAGGGATT TGTATAAGAA ATATCTTTAA AAAACCCAT ATGCTAATTT
1651   GACATAATTT TTGAGAAAAA TATATATTCA GGCGAATTCT CACAATGAAC
1701   AATAATAAGA TTAAATAGC TTTCCCCCGT TGCAGCGCAT GGGTATTTTT
1751   TCTAGTAAAA ATAAAGATA AACTTAGACT CAAAACATTT ACAAAAACAA
1801   CCCCTAAAGT TCCTAAAGCC CAAAGTGCTA TCCACGATCC ATAGCAAGCC
1851   CAGCCCAACC CAACCCAACC CAACCCACCC CAGTCCAGCC AACTGGACAA
1901   TAGTCTCCAC ACCCCCCCAC TATCACCGTG AGTTGTCCGC ACGCACCGCA
1951   CGTCTCGCAG CCAAAAAAAA AAAAAGAAAG AAAAAAAAGA AAAAGAAAAA
2001   ACAGCAGGTG GGTCCGGGTC GTGGGGCCG GAAACGCGAG GAGGATCGCG
2051   AGCCAGCGAC GAGGCCGGCC CTCCCTCCGC TTCCAAAGAA ACGCCCCCA
2101   TCGCCACTAT ATACATACCC CCCCCTCTCC TCCCATCCCC CAACCCTAC
2151   CACCACCACC ACCACCACCT CCACCTCCTC CCCCCTCGCT GCCGGACGAC
2201   GCCTCCCCCC TCCCCCTCCG CCGCCGCCGC GCCGGTAACC ACCCCGCCCC
2251   TCTCCTCTTT CTTTCTCCGT TTTTTTTTC CGTCTCGGTC TCGATCTTTG
2301   GCCTTGGTAG TTTGGGTGGG CGAGAGGCGG CTTCGTGCGC GCCCAGATCG
2351   GTGCGCGGGA GGGGCGGGAT CTCGCGGCTG GGCTCTCGC CGGCGTGGAT
2401   CCGGCCCGGA TCTCGCGGGG AATGGGGCTC TCGGATGTAG ATCTGCGATC
2451   CGCCGTTGTT GGGGGAGATG ATGGGGGGTT TAAAATTTCC GCCATGCTAA
2501   ACAAGATCAG GAAGAGGGGA AAAGGGCACT ATGGTTTATA TTTTTATATA
2551   TTTCTGCTGC TTCGTCAGGC TTAGATGTGC TAGATCTTTC TTTCTTCTTT
2601   TTGTGGGTAG AATTTGAATC CCTCAGCATT GTTCATCGGT AGTTTTCTT
2651   TTCATGATTT GTGACAAATG CAGCCTCGTG CGGAGCTTTT TTGTAGGTAG
2701   ACCATGGCTT CTCCGGAGAG GAGACCAGTT GAGATTAGGC CAGCTACAGC
2751   AGCTGATATG GCCGCGGTTT GTGATATCGT TAACCATTAC ATTGAGACGT
2801   CTACAGTGAA CTTTAGGACA GAGCCACAAA CACCACAAGA GTGGATTGAT
2851   GATCTAGAGA GGTTGCAAGA TAGATACCCT TGGTTGGTTG CTGAGGTTGA
2901   GGGTGTTGTG GCTGGTATTG CTTACGCTGG GCCCTGGAAG GCTAGGAACG
2951   CTTACGATTG GACAGTTGAG AGTACTGTTT ACGTGTCACA TAGGCATCAA
3001   AGGTTGGGCC TAGGATCCAC ATTGTACACA CATTTGCTTA AGTCTATGGA
3051   GGCGCAAGGT TTTAAGTCTG TGGTTGCTGT TATAGGCCTT CCAAACGATC
3101   CATCTGTTAG GTTGCATGAG GCTTTGGGAT ACACAGCCCG GGGTACATTG
3151   CGCGCAGCTG GATACAAGCA TGGTGGATGG CATGATGTTG GTTTTGGCA
3201   AAGGGATTTT GAGTTGCCAG CTCCTCCAAG GCCAGTTAGG CCAGTTACCC
3251   AGATCTGAGG TACCCTGAGC TCGGTCGCAG CGTGTGCGTG TCCGTCGTAC
3301   GTTCTGGCCG GCCGGGCCTT GGGCGCGCGA TCAGAAGCGT TGCGTTGGCG
3351   TGTGTGTGCT TCTGGTTTGC TTTAATTTTA CCAAGTTTGT TTCAAGGTGG
3401   ATCGCGTGGT CAAGGCCCGT GTGCTTTAAA GACCCACCGG CACTGGCAGT
3451   GAGTGTTGCT GCTTGTGTAG GCTTTGGTAC GTATGGGCTT TATTTGCTTC
```

FIG 7B CONT.

```
3501  TGGATGTTGT GTACTACTTG GGTTTGTTGA ATTATTATGA GCAGTTGCGT
3551  ATTGTAATTC AGCTGGGCTA CCTGGACATT GTTATGTATT AATAAATGCT
3601  TTGCTTTCTT CTAAAGATCT TTAAGTGCTG AATTCATATT TCCTCCTGCA
3651  GGGTTTAAAC TTGCCGTGGC CTATTTTCAG AAGAAGTTCC CAATAGTAGT
3701  CCAAAATTTT TGTAACGAAG GGAGCATAAT AGTTACATGC AAAGGAAAAC
3751  TGCCATTCTT TAGAGGGGAT GCTTGTTTAA GAACAAAAAA TATATCACTT
3801  TCTTTTGTTC CAAGTCATTG CGTATTTTTT TAAAAATATT TGTTCCTTCG
3851  TATATTTCGA GCTTCAATCA CTTTATGGTT CTTTGTATTC TGGCTTTGCT
3901  GTAAATCGTA GCTAACCTTC TTCCTAGCAG AAATTATTAA TACTTGGGAT
3951  ATTTTTTTAG AATCAAGTAA ATTACATATT ACCACCACAT CGAGCTGCTT
4001  TTAAATTCAT ATTACAGCCA TATAGGCTTG ATTCATTTTG CAAAATTTCC
4051  AGGATATTGA CAACGTTAAC TTAATAATAT CTTGAAATAT TAAAGCTATT
4101  ATGATTAGGG GTGCAAATGG ACCGAGTTGG TTCGGTTTAT ATCAAAATCA
4151  AACCAAACCA ACTATATCGG TTTGGATTGG TTCGGTTTTG CCGGGTTTTC
4201  AGCATTTTCT GGTTTTTTTT TTGTTAGATG AATATTATTT TAATCTTACT
4251  TTGTCAAATT TTTGATAAGT AAATATATGT GTTAGTAAAA ATTAATTTTT
4301  TTTACAAACA TATGATCTAT TAAAATATTC TTATAGGAGA ATTTTCTTAA
4351  TAACACATGA TATTTATTTA TTTTAGTCGT TTGACTAATT TTTCGTTGAT
4401  GTACACTTTC AAAGTTAACC AAATTTAGTA ATTAAGTATA AAAATCAATA
4451  TGATACCTAA ATAATGATAT GTTCTATTTA ATTTTAAATT ATCGAAATTT
4501  CACTTCAAAT TCGAAAAAGA TATATAAGAA TTTTGATAGA TTTTGACATA
4551  TGAATATGGA AGAACAAAGA GATTGACGCA TTTTAGTAAC ACTTGATAAG
4601  AAAGTGATCG TACAACCAAT TATTTAAAGT TAATAAAAAT GGAGCACTTC
4651  ATATTTAACG AAATATTACA TGCCAGAAGA GTCGCAAATA TTTCTAGATA
4701  TTTTTTAAAG AAAATTCTAT AAAAAGTCTT AAAGGCATAT ATATAAAAAC
4751  TATATATTTA TATTTTGGTT TGGTTCGAAT TTGTTTTACT CAATACCAAA
4801  CTAAATTAGA CCAAATATAA TTGGGATTTT TAATCGCGGC CCACTAGTCA
4851  CCGGTGTAGC TTGGCGTAAT CATGGTCATA GCTGTTTCCT GTGTGAAATT
4901  GTTATCCGCT CACAATTCCA CACAACATAC GAGCCGGAAG CATAAAGTGT
4951  AAAGCCTGGG GTGCCTAATG AGTGAGCTAA CTCACATTAA TTGCGTTGCG
5001  CTCACTGCCC GCTTTCCAGT CGGGAAACCT GTCGTGCCAG CTGCATTAAT
5051  GAATCGGCCA ACGCGCGGGG AGAGGCGGTT TGCGTATTGG GCGCTCTTCC
5101  GCTGCGCACG CTGCGCACGC TGCGCACGCT TCCTCGCTCA CTGACTCGCT
5151  GCGCTCGGTC GTTCGGCTGC GGCGAGCGGT ATCAGCTCAC TCAAAGGCGG
5201  TAATACGGTT ATCCACAGAA TCAGGGGATA ACGCAGGAAA GAACATGTGA
5251  GCAAAAGGCC AGCAAAAGGC CAGGAACCGT AAAAAGGCCG CGTTGCTGGC
5301  GTTTTTCCAT AGGCTCCGCC CCCCTGACGA GCATCACAAA AATCGACGCT
5351  CAAGTCAGAG GTGGCGAAAC CCGACAGGAC TATAAAGATA CCAGGCGTTT
5401  CCCCCTGGAA GCTCCCTCGT GCGCTCTCCT GTTCCGACCC TGCCGCTTAC
5451  CGGATACCTG TCCGCCTTTC TCCCTTCGGG AAGCGTGGCG CTTTCTCATA
5501  GCTCACGCTG TAGGTATCTC AGTTCGGTGT AGGTCGTTCG CTCCAAGCTG
5551  GGCTGTGTGC ACGAACCCCC CGTTCAGCCC GACCGCTGCG CCTTATCCGG
5601  TAACTATCGT CTTGAGTCCA ACCCGGTAAG ACACGACTTA TCGCCACTGG
5651  CAGCAGCCAC TGGTAACAGG ATTAGCAGAG CGAGGTATGT AGGCGGTGCT
5701  ACAGAGTTCT TGAAGTGGTG GCCTAACTAC GGCTACACTA GAAGGACAGT
5751  ATTTGGTATC TGCGCTCTGC TGAAGCCAGT TACCTTCGGA AAAAGAGTTG
5801  GTAGCTCTTG ATCCGGCAAA CAAACCACCG CTGGTAGCGG TGGTTTTTTT
5851  GTTTGCAAGC AGCAGATTAC GCGCAGAAAA AAAGGATCTC AAGAAGATCC
5901  TTTGATCTTT TCTACGGGGT CTGACGCTCA GTGGAACGAA AACTCACGTT
5951  AAGGGATTTT GGTCATGAGA TTATCAAAAA GGATCTTCAC CTAGATCCTT
6001  TTAAATTAAA AATGAAGTTT TAAATCAATC TAAAGTATAT ATGAGTAAAC
6051  TTGGTCTGAC AGTTACCAAT GCTTAATCAG TGAGGCACCT ATCTCAGCGA
```

FIG 7B CONT.

```
6101  TCTGTCTATT TCGTTCATCC ATAGTTGCCT GACTCCCCGT CGTGTAGATA
6151  ACTACGATAC GGGAGGGCTT ACCATCTGGC CCCAGTGCTG CAATGATACC
6201  GCGAGACCCA CGCTCACCGG CTCCAGATTT ATCAGCAATA AACCAGCCAG
6251  CCGGAAGGGC CGAGCGCAGA AGTGGTCCTG CAACTTTATC CGCCTCCATC
6301  CAGTCTATTA ATTGTTGCCG GGAAGCTAGA GTAAGTAGTT CGCCAGTTAA
6351  TAGTTTGCGC AACGTTGTTG CCATTGCTAC AGGCATCGTG GTGTCACGCT
6401  CGTCGTTTGG TATGGCTTCA TTCAGCTCCG GTTCCCAACG ATCAAGGCGA
6451  GTTACATGAT CCCCCATGTT GTGCAAAAAA GCGGTAGCT CCTTCGGTCC
6501  TCCGATCGTT GTCAGAAGTA AGTTGGCCGC AGTGTTATCA CTCATGGTTA
6551  TGGCAGCACT GCATAATTCT CTTACTGTCA TGCCATCCGT AAGATGCTTT
6601  TCTGTGACTG GTGAGTACTC AACCAAGTCA TTCTGAGAAT AGTGTATGCG
6651  GCGACCGAGT TGCTCTTGCC CGGCGTCAAT ACGGGATAAT ACCGCGCCAC
6701  ATAGCAGAAC TTTAAAAGTG CTCATCATTG GAAAACGTTC TTCGGGGCGA
6751  AAACTCTCAA GGATCTTACC GCTGTTGAGA TCCAGTTCGA TGTAACCCAC
6801  TCGTGCACCC AACTGATCTT CAGCATCTTT TACTTTCACC AGCGTTTCTG
6851  GGTGAGCAAA AACAGGAAGG CAAAATGCCG CAAAAAAGGG AATAAGGGCG
6901  ACACGGAAAT GTTGAATACT CATACTCTTC CTTTTTCAAT ATTATTGAAG
6951  CATTTATCAG GGTTATTGTC TCATGAGCGG ATACATATTT GAATGTATTT
7001  AGAAAAATAA ACAAATAGGG GTTCCGCGCA CATTTCCCCG AAAAGTGCCA
7051  CCTGACGTCT AAGAAACCAT TATTATCATG ACATTAACCT ATAAAAATAG
7101  GCGTATCACG AGGCCCTTTC GTCTCGCGCG TTTCGGTGAT GACGGTGAAA
7151  ACCTCTGACA CATGCAGCTC CCGGAGACGG TCACAGCTTG TCTGTAAGCG
7201  GATGCCGGGA GCAGACAAGC CCGTCAGGGC GCGTCAGCGG GTGTTGGCGG
7251  GTGTCGGGGC TGGCTTAACT ATGCGGCATC AGAGCAGATT GTACTGAGAG
7301  TGCACCATAT GCGGTGTGAA ATACCGCACA GATGCGTAAG GAGAAAATAC
7351  CGCATCAGGC GCCATTCGCC ATTCAGGCTG CGCAACTGTT GGGAAGGGCG
7401  ATCGGTGCGG GCCTCTTCGC TATTACGCCA GCTGGCGAAA GGGGGATGTG
7451  CTGCAAGGCG ATTAAGTTGG GTAACGCCAG GGTTTTCCCA GTCACGACGT
7501  TGTAAAACGA CGGCCAGTGA ATTACACCGG TGTGATCATG GGCCG
```

FIG 7B CONT.

pDAB7113 11643bp

| Sequence | Feature |
|---|---|
| 1-1164bp | RB7 MAR v3 |
| 1165-1233 Linker | TGGCCACCGCTTAATTAAGGCGCGCCATGCCCCCTGCAGATCCCCGGGGATCCTCTAGAGTCGACCTGC |
| 1234-3224 | Maize Ubiquitin 1 promoter |
| 3224-4891 | GNT III v.2 |
| 3627 | C to replace G as reported in original sequence |
| 4892-4895 Linker | TAGGTTT |
| 4896-5260 | Maize Per5 3'UTR v2 |
| 5261-5404 multiple cloning sites | CGGCCGGCCTAGCTAGCCACGGTGGCCAGATCCACTAGGGGCAAGCGGCCGCTTAATTAAATTTAAATGTTTAAACTAGGAAATCCAAGCTTGGGCTGCAGGTCAATCCCATTGCTTTTGAAGCAGCTCAACATTGATCTCTTT |
| 5405-6802 | Rice Actin 1 Promoter v2 |
| 6803-7358 | PAT v3 |
| 7359-7372 Linker | GGTACCCTGAGCTC |
| 7373-7729 | Maize Lipase 3' UTR v1 |
| 7730-7770 Linker | GAATTCATATTTCCTCCTGCAGGGTTTAAACTTGCCGTGGC |
| 7771-8934 | RB7 MAR v3 |
| 8935-11643 | PUC19 |
| 9201-9225 | 3 FspI sites (TGCGCAA) with CG in between sites |
| 10164-11021 | Ampicillin resistance gene |
| 10454-10459 | TGCGCAA FspI |
| 11477-11482 | TGCGCAA FspI |

```
  1  CGATTAAAAA CCCAATTATA TTTGGTCTAA TTTAGTTTGG
     TATTGAGTAA AACAAATTCG AACCAAACCA AAATATAAAT
     ATATAGTTTT TATATATATG
101  CCTTTAAGAC TTTTTATAGA ATTTTCTTTA AAAAATATCT
     AGAAATATTT GCGACTCTTC TGGCATGTAA TATTTCGTTA
     AATATGAAGT GCTCCATTTT
201  TATTAACTTT AAATAATTGG TTGTACGATC ACTTTCTTAT
     CAAGTGTTAC TAAAATGCGT CAATCTCTTT GTTCTTCCAT
     ATTCATATGT CAAAATCTAT
301  CAAAATTCTT ATATATCTTT TTCGAATTTG AAGTGAAATT
     TCGATAATTT AAAATTAAAT AGAACATATC ATTATTTAGG
     TATCATATTG ATTTTTATAC
```

FIG 8B

401 TTAATTACTA AATTTGGTTA ACTTTGAAAG TGTACATCAA
    CGAAAAATTA GTCAAACGAC TAAAATAAAT AAATATCATG
    TGTTATTAAG AAAATTCTCC
501 TATAAGAATA TTTTAATAGA TCATATGTTT GTAAAAAAAA
    TTAATTTTTA CTAACACATA TATTTACTTA TCAAAAATTT
    GACAAAGTAA GATTAAAATA
601 ATATTCATCT AACAAAAAAA AAACCAGAAA ATGCTGAAAA
    CCCGGCAAAA CCGAACCAAT CCAAACCGAT ATAGTTGGTT
    TGGTTTGATT TTGATATAAA
701 CCGAACCAAC TCGGTCCATT TGCACCCCTA ATCATAATAG
    CTTTAATATT TCAAGATATT ATTAAGTTAA CGTTGTCAAT
    ATCCTGGAAA TTTTGCAAAA
801 TGAATCAAGC CTATATGGCT GTAATATGAA TTTAAAAGCA
    GCTCGATGTG GTGGTAATAT GTAATTTACT TGATTCTAAA
    AAAATATCCC AAGTATTAAT
901 AATTTCTGCT AGGAAGAAGG TTAGCTACGA TTTACAGCAA
    AGCCAGAATA CAAAGAACCA TAAAGTGATT GAAGCTCGAA
    ATATACGAAG GAACAAATAT
1001 TTTTAAAAAA ATACGCAATG ACTTGGAACA AAAGAAAGTG
     ATATATTTTT TGTTCTTAAA CAAGCATCCC CTCTAAAGAA
     TGGCAGTTTT CCTTTGCATG

PacI

~~~~~~~~~

AscI

~~~~~~~~~

1101 TAACTATTAT GCTCCCTTCG TTACAAAAAT TTTGGACTAC
     TATTGGGAAT TCTTCTGAAA ATAGTGGCCA CCGCTTAATT
     AAGGCGCGCC ATGCCCCCTG
                          BamHI
                          ~~~~~~
1201 CAGATCCCCG GGGATCCTCT AGAGTCGACC TGCAGTGCAG
     CGTGACCCGG TCGTGCCCCT CTCTAGAGAT AATGAGCATT
     GCATGTCTAA GTTATAAAAA
1301 ATTACCACAT ATTTTTTTTG TCACACTTGT TTGAAGTGCA
     GTTTATCTAT CTTTATACAT ATATTTAAAC TTTAATCTAC
     GAATAATATA ATCTATAGTA
1401 CTACAATAAT ATCAGTGTTT TAGAGAATCA TATAAATGAA
     CAGTTAGACA TGGTCTAAAG GACAATTGAG TATTTTGACA
     ACAGGACTCT ACAGTTTTAT
1501 CTTTTTAGTG TGCATGTGTT CTCCTTTTTT TTTGCAAATA
     GCTTCACCTA TATAATACTT CATCCATTTT ATTAGTACAT
     CCATTTAGGG TTTAGGGTTA

FIG 8B CONT.

1601 ATGGTTTTTA TAGACTAATT TTTTTAGTAC ATCTATTTTA
     TTCTATTTTA GCCTCTAAAT TAAGAAAACT AAAACTCTAT
     TTTAGTTTTT TTATTTAATA
1701 ATTTAGATAT AAAATAGAAT AAAATAAAGT GACTAAAAAT
     TAAACAAATA CCCTTTAAGA AATTAAAAAA ACTAAGGAAA
     CATTTTTCTT GTTTCGAGTA
1801 GATAATGCCA GCCTGTTAAA CGCCGTCGAC GAGTCTAACG
     GACACCAACC AGCGAACCAG CAGCGTCGCG TCGGGCCAAG
     CGAAGCAGAC GGCACGGCAT
1901 CTCTGTCGCT GCCTCTGGAC CCCTCTCGAG AGTTCCGCTC
     CACCGTTGGA CTTGCTCCGC TGTCGGCATC CAGAAATTGC
     GTGGCGGAGC GGCAGACGTG
2001 AGCCGGCACG GCAGGCGGCC TCCTCCTCCT CTCACGGCAC
     GGCAGCTACG GGGGATTCCT TTCCCACCGC TCCTTCGCTT
     TCCCTTCCTC GCCCGCCGTA
2101 ATAAATAGAC ACCCCTCCA CACCCTCTTT CCCCAACCTC
     GTGTTGTTCG GAGCGCACAC ACACACAACC AGATCTCCCC
     CAAATCCACC CGTCGGCACC
2201 TCCGCTTCAA GGTACGCCGC TCGTCCTCCC CCCCCCCCCC
     TCTCTACCTT CTCTAGATCG GCGTTCCGGT CCATGCATGG
     TTAGGGCCCG GTAGTTCTAC
2301 TTCTGTTCAT GTTTGTGTTA GATCCGTGTT TGTGTTAGAT
     CCGTGCTGCT AGCGTTCGTA CACGGATGCG ACCTGTACGT
     CAGACACGTT CTGATTGCTA
2401 ACTTGCCAGT GTTTCTCTTT GGGGAATCCT GGGATGGCTC
     TAGCCGTTCC GCAGACGGGA TCGATTTCAT GATTTTTTTT
     GTTTCGTTGC ATAGGGTTTG
2501 GTTTGCCCTT TTCCTTTATT TCAATATATG CCGTGCACTT
     GTTTGTCGGG TCATCTTTTC ATGCTTTTTT TTGTCTTGGT
     TGTGATGATG TGGTCTGGTT
2601 GGGCGGTCGT TCTAGATCGG AGTAGAATTC TGTTTCAAAC
     TACCTGGTGG ATTTATTAAT TTTGGATCTG TATGTGTGTG
     CCATACATAT TCATAGTTAC
2701 GAATTGAAGA TGATGGATGG AAATATCGAT CTAGGATAGG
     TATACATGTT GATGCGGGTT TTACTGATGC ATATACAGAG
     ATGCTTTTTG TTCGCTTGGT
2801 TGTGATGATG TGGTGTGGTT GGGCGGTCGT TCATTCGTTC
     TAGATCGGAG TAGAATACTG TTTCAAACTA CCTGGTGTAT
     TTATTAATTT TGGAACTGTA
2901 TGTGTGTGTC ATACATCTTC ATAGTTACGA GTTTAAGATG
     GATGGAAATA TCGATCTAGG ATAGGTATAC ATGTTGATGT
     GGGTTTTACT GATGCATATA
3001 CATGATGGCA TATGCAGCAT CTATTCATAT GCTCTAACCT
     TGAGTACCTA TCTATTATAA TAAACAAGTA TGTTTTATAA
     TTATTTTGAT CTTGATATAC
3101 TTGGATGATG GCATATGCAG CAGCTATATG TGGATTTTTT
     TAGCCCTGCC TTCATACGCT ATTTATTTGC TTGGTACTGT
     TTCTTTTGTC GATGCTCACC

FIG 8B CONT.

```
            NcoI
            FseI

~~~~~~
            ~~~~~~~~~
    3201    CTGTTGTTTG GTGTTACTTC TGCAGGGTAC CCCCGGGGTC
            GACCATGGTG ATGAGACGCT ACAAGCTCTT TCTCATGTTC
            TGTATGGCCG GCCTGTGCCT
    3301    CATCTCCTTC CTGCACTTCT TCAAGACCCT GTCCTATGTC
            ACCTTCCCCC GAGAACTGGC CTCCCTCAGC CCTAACCTGG
            TGTCCAGCTT TTTCTGGAAC
    3401    AATGCCCCGG TCACGCCCCA GGCCAGCCCC GAGCCAGGAG
            GCCCTGACCT GCTGCGTACC CCACTCTACT CCCACTCGCC
            CCTGCTGCAG CCGCTGCCGC
                            SacI
                            ~~~~~~~~
    3501    CCAGCAAGGC GGCCGAGGAG CTCCACCGGG TGGACTTGGT
            GCTGCCCGAG GACACCACCG AGTATTTCGT GCGCACCAAG
            GCCGGCGGCG TCTGCTTCAA
    3601    ACCCGGCACC AAGATGCTGG AGAGGCCCCC CCCGGGACGG
            CCGGAGGAGA AGCCTGAGGG GGCCAACGGC TCCTCGGCCC
            GGCGGCCACC CCGGTACCTC
    3701    CTGAGCGCCC GGGAGCGCAC GGGGGGCCGA GGCGCCCGGC
            GCAAGTGGGT GGAGTGCGTG TGCCTGCCCG GCTGGCACGG
            ACCCAGCTGC GGCGTGCCCA
    3801    CTGTGGTGCA GTACTCCAAC CTGCCCACCA AGGAGCGGCT
            GGTGCCCAGG GAGGTGCCGC GCCGCGTCAT CAACGCCATC
            AACGTCAACC ACGAGTTCGA

NotI

~~~~~~~~~~
    3901    CCTGCTGGAC GTGCGCTTCC ACGAGCTGGG CGACGTGGTG
            GACGCCTTTG TGGTGTGCGA GTCCAACTTC ACGGCTTATG
            GGGAGCCGCG GCCGCTCAAG
    4001    TTCCGGGAGA TGCTGACCAA TGGCACCTTC GAGTACATCC
            GCCACAAGGT GCTCTATGTC TTCCTGGACC ACTTCCCGCC
            CGGCGGCCGG CAGGACGGCT
    4101    GGATCGCCGA CGACTACCTG CGCACCTTCC TCACCCAGGA
            CGGCGTCTCG CGGCTGCGCA ACCTGCGGCC CGACGACGTC
            TTCATCATTG ACGATGCGGA
    4201    CGAGATCCCG GCCCGTGACG GCGTCCTTTT CCTCAAGCTC
            TACGATGGCT GGACCGAGCC CTTCGCCTTC CACATGCGCA
            AGTCGCTCTA CGGCTTCTTC
    4301    TGGAAGCAGC CGGGCACCCT GGAGGTGGTG TCAGGCTGCA
            CGGTGGACAT GCTGCAGGCA GTGTATGGGC TGGACGGCAT
            CCGCCTGCGC CGCCGCCAGT
```

FIG 8B CONT.

4401 ACTACACCAT GCCCAACTTC AGACAGTATG AGAACCGCAC
     CGGCCACATC CTGGTGCAGT GGTCGCTGGG CAGCCCCCTG
     CACTTCGCCG GCTGGCACTG
4501 CTCCTGGTGC TTCACGCCCG AGGGCATCTA CTTCAAGCTC
     GTGTCCGCCC AGAATGGCGA CTTCCCACGC TGGGGTGACT
     ACGAGGACAA GCGGGACCTG
4601 AACTACATCC GCGGCCTGAT CCGCACCGGG GGCTGGTTCG
     ACGGCACGCA GCAGGAGTAC CCGCCTGCAG ACCCCAGCGA
     GCACATGTAT GCGCCCAAGT
4701 ACCTGCTGAA GAACTACGAC CGGTTCCACT ACCTGCTGGA
     CAACCCCTAC CAGGAGCCCA GGAGCACGGC GGCGGGCGGG
     TGGCGCCACA GGGGTCCCGA

BamHI        PmeI
     ~~~~~~~      ~~~~~~~~~

4801 GGGAAGGCCG CCCGCCCGGG GCAAACTGGA CGAGGCGGAA
     GTCGAACAAA AACTCATCTC AGAAGAGGAT CTGAATTAGG
     ATCCTAGGTT TAAACTGAGG
4901 GCACTGAAGT CGCTTGATGT GCTGAATTGT TTGTGATGTT
     GGTGGCGTAT TTTGTTTAAA TAAGTAAGCA TGGCTGTGAT
     TTTATCATAT GATCGATCTT
5001 TGGGGTTTTA TTTAACACAT TGTAAAATGT GTATCTATTA
     ATAACTCAAT GTATAAGATG TGTTCATTCT TCGGTTGCCA
     TAGATCTGCT TATTTGACCT
5101 GTGATGTTTT GACTCCAAAA ACCAAAAATCA CAACTCAATA
     AACTCATGGA ATATGTCCAC CTGTTTCTTG AAGAGTTCAT
     CTACCATTCC AGTTGGCATT

FseI
     ~~~~~~~~

5201 TATCAGTGTT GCAGCGGCGC TGTGCTTTGT AACATAACAA
     TTGTTCACGG CATATATCCA CGGCCGGCCT AGCTAGCCAC
     GGTGGCCAGA TCCACTAGGG
                         PacI
                         ~~~~~~~~~~
                ı    SwaI
                     ~~~~~~~~
         NotI                    PmeI
     HindIII                     ~~~~~~~~~
     ~~~~~~
5301 GCAAGCGGCC GCTTAATTAA ATTTAAATGT TTAAACTAGG
     AAATCCAAGC TTGGGCTGCA GGTCAATCCC ATTGCTTTTG
     AAGCAGCTCA ACATTGATCT

FIG 8B CONT.

5401 CTTTCTCGAG GTCATTCATA TGCTTGAGAA GAGAGTCGGG
     ATAGTCCAAA ATAAAACAAA GGTAAGATTA CCTGGTCAAA
     AGTGAAAACA TCAGTTAAAA
5501 GGTGGTATAA AGTAAAATAT CGGTAATAAA AGGTGGCCCA
     AAGTGAAATT TACTCTTTTC TACTATTATA AAAATTGAGG
     ATGTTTTTGT CGGTACTTTG
5601 ATACGTCATT TTTGTATGAA TTGGTTTTTA AGTTTATTCG
     CTTTTGGAAA TGCATATCTG TATTTGAGTC GGGTTTTAAG
     TTCGTTTGCT TTTGTAAATA
5701 CAGAGGGATT TGTATAAGAA ATATCTTTAA AAAAACCCAT
     ATGCTAATTT GACATAATTT TTGAGAAAAA TATATATTCA
     GGCGAATTCT CACAATGAAC
5801 AATAATAAGA TTAAAATAGC TTTCCCCCGT TGCAGCGCAT
     GGGTATTTTT TCTAGTAAAA ATAAAGATA AACTTAGACT
     CAAAACATTT ACAAAAACAA
5901 CCCCTAAAGT TCCTAAAGCC CAAAGTGCTA TCCACGATCC
     ATAGCAAGCC CAGCCCAACC CAACCCAACC CAACCCACCC
     CAGTCCAGCC AACTGGACAA
6001 TAGTCTCCAC ACCCCCCCAC TATCACCGTG AGTTGTCCGC
     ACGCACCGCA CGTCTCGCAG CCAAAAAAAA AAAAAGAAAG
     AAAAAAAGA AAAAGAAAAA

FseI

~~~~~~~~~~

6101 ACAGCAGGTG GGTCCGGGTC GTGGGGGCCG GAAACGCGAG
     GAGGATCGCG AGCCAGCGAC GAGGCCGGCC CTCCCTCCGC
     TTCCAAAGAA ACGCCCCCCA
6201 TCGCCACTAT ATACATACCC CCCCTCTCC TCCCATCCCC
     CCAACCCTAC CACCACCACC ACCACCACCT CCACCTCCTC
     CCCCCTCGCT GCCGGACGAC
6301 GCCTCCCCCC TCCCCCTCCG CCGCCGCCGC GCCGGTAACC
     ACCCCGCCCC TCTCCTCTTT CTTTCTCCGT TTTTTTTTTC
     CGTCTCGGTC TCGATCTTTG

BamHI

~~~~

6401 GCCTTGGTAG TTTGGGTGGG CGAGAGGCGG CTTCGTGCGC
     GCCCAGATCG GTGCGCGGGA GGGGCGGGAT CTCGCGGCTG
     GGGCTCTCGC CGGCGTGGAT
     BamHI
     ~~
6501 CCGGCCCGGA TCTCGCGGGG AATGGGGCTC TCGGATGTAG
     ATCTGCGATC CGCCGTTGTT GGGGGAGATG ATGGGGGGTT
     TAAAATTTCC GCCATGCTAA

FIG 8B CONT.

6601 ACAAGATCAG GAAGAGGGGA AAAGGGCACT ATGGTTTATA
     TTTTTATATA TTTCTGCTGC TTCGTCAGGC TTAGATGTGC
     TAGATCTTTC TTTCTTCTTT
6701 TTGTGGGTAG AATTTGAATC CCTCAGCATT GTTCATCGGT
     AGTTTTTCTT TTCATGATTT GTGACAAATG CAGCCTCGTG
     CGGAGCTTTT TTGTAGGTAG
          NcoI
          ~~~~~~
6801 ACCATGGCTT CTCCGGAGAG GAGACCAGTT GAGATTAGGC
     CAGCTACAGC AGCTGATATG GCCGCGGTTT GTGATATCGT
     TAACCATTAC ATTGAGACGT
6901 CTACAGTGAA CTTTAGGACA GAGCCACAAA CACCACAAGA
     GTGGATTGAT GATCTAGAGA GGTTGCAAGA TAGATACCCT
     TGGTTGGTTG CTGAGGTTGA
7001 GGGTGTTGTG GCTGGTATTG CTTACGCTGG GCCCTGGAAG
     GCTAGGAACG CTTACGATTG GACAGTTGAG AGTACTGTTT
     ACGTGTCACA TAGGCATCAA
                    BamHI
                    ~~~~~~
7101 AGGTTGGGCC TAGGATCCAC ATTGTACACA CATTTGCTTA
     AGTCTATGGA GGCGCAAGGT TTTAAGTCTG TGGTTGCTGT
     TATAGGCCTT CCAAACGATC
7201 CATCTGTTAG GTTGCATGAG GCTTTGGGAT ACACAGCCCG
     GGGTACATTG CGCGCAGCTG GATACAAGCA TGGTGGATGG
     CATGATGTTG GTTTTTGGCA

SacI

~~~~~~~
7301 AAGGGATTTT GAGTTGCCAG CTCCTCCAAG GCCAGTTAGG
     CCAGTTACCC AGATCTGAGG TACCCTGAGC TCGGTCGCAG
     CGTGTGCGTG TCCGTCGTAC
              FseI
              ~~~~~~~~~~
7401 GTTCTGGCCG GCCGGGCCTT GGGCGCGCGA TCAGAAGCGT
     TGCGTTGGCG TGTGTGTGCT TCTGGTTTGC TTTAATTTTA
     CCAAGTTTGT TTCAAGGTGG
7501 ATCGCGTGGT CAAGGCCCGT GTGCTTTAAA GACCCACCGG
     CACTGGCAGT GAGTGTTGCT GCTTGTGTAG GCTTTGGTAC
     GTATGGGCTT TATTTGCTTC
7601 TGGATGTTGT GTACTACTTG GGTTTGTTGA ATTATTATGA
     GCAGTTGCGT ATTGTAATTC AGCTGGGCTA CCTGGACATT
     GTTATGTATT AATAAATGCT

PmeI

```
7701  TTGCTTTCTT CTAAAGATCT TTAAGTGCTG AATTCATATT
      TCCTCCTGCA GGGTTTAAAC TTGCCGTGGC CTATTTTCAG
      AAGAATTCCC AATAGTAGTC
7801  CAAAATTTTT GTAACGAAGG GAGCATAATA GTTACATGCA
      AAGGAAAACT GCCATTCTTT AGAGGGGATG CTTGTTTAAG
      AACAAAAAAT ATATCACTTT
7901  CTTTTGTTCC AAGTCATTGC GTATTTTTTT AAAAATATTT
      GTTCCTTCGT ATATTTCGAG CTTCAATCAC TTTATGGTTC
      TTTGTATTCT GGCTTTGCTG
8001  TAAATCGTAG CTAACCTTCT TCCTAGCAGA AATTATTAAT
      ACTTGGGATA TTTTTTTAGA ATCAAGTAAA TTACATATTA
      CCACCACATC GAGCTGCTTT
8101  TAAATTCATA TTACAGCCAT ATAGGCTTGA TTCATTTTGC
      AAAATTTCCA GGATATTGAC AACGTTAACT TAATAATATC
      TTGAAATATT AAAGCTATTA
8201  TGATTAGGGG TGCAAATGGA CCGAGTTGGT TCGGTTTATA
      TCAAAATCAA ACCAAACCAA CTATATCGGT TTGGATTGGT
      TCGGTTTTGC CGGGTTTTCA
8301  GCATTTTCTG GTTTTTTTTT TGTTAGATGA ATATTATTTT
      AATCTTACTT TGTCAAATTT TTGATAAGTA AATATATGTG
      TTAGTAAAAA TTAATTTTTT
8401  TTACAAACAT ATGATCTATT AAAATATTCT TATAGGAGAA
      TTTTCTTAAT AACACATGAT ATTTATTTAT TTTAGTCGTT
      TGACTAATTT TTCGTTGATG
8501  TACACTTTCA AAGTTAACCA AATTTAGTAA TTAAGTATAA
      AAATCAATAT GATACCTAAA TAATGATATG TTCTATTTAA
      TTTTAAATTA TCGAAATTTC
8601  ACTTCAAATT CGAAAAAGAT ATATAAGAAT TTTGATAGAT
      TTTGACATAT GAATATGGAA GAACAAAGAG ATTGACGCAT
      TTTAGTAACA CTTGATAAGA
8701  AAGTGATCGT ACAACCAATT ATTTAAAGTT AATAAAAATG
      GAGCACTTCA TATTTAACGA AATATTACAT GCCAGAAGAG
      TCGCAAATAT TTCTAGATAT
8801  TTTTTAAAGA AAATTCTATA AAAAGTCTTA AAGGCATATA
      TATAAAAACT ATATATTTAT ATTTTGGTTT GGTTCGAATT
      TGTTTTACTC AATACCAAAC
8901  TAAATTAGAC CAAATATAAT TGGGTTTTTA ATCGCGGCCC
      ACTAGTCACC GGTGTAGCTT GGCGTAATCA TGGTCATAGC
      TGTTTCCTGT GTGAAATTGT
9001  TATCCGCTCA CAATTCCACA CAACATACGA GCCGGAAGCA
      TAAAGTGTAA AGCCTGGGGT GCCTAATGAG TGAGCTAACT
      CACATTAATT GCGTTGCGCT
9101  CACTGCCCGC TTTCCAGTCG GGAAACCTGT CGTGCCAGCT
      GCATTAATGA ATCGGCCAAC GCGCGGGGAG AGGCGGTTTG
      CGTATTGGGC GCTCTTCCGC
9201  TGCGCACGCT GCGCACGCTG CGCACGCTTC CTCGCTCACT
      GACTCGCTGC GCTCGGTCGT TCGGCTGCGG CGAGCGGTAT
      CAGCTCACTC AAAGGCGGTA
```

FIG 8B CONT.

```
 9301  ATACGGTTAT CCACAGAATC AGGGGATAAC GCAGGAAAGA
       ACATGTGAGC AAAAGGCCAG CAAAAGGCCA GGAACCGTAA
       AAAGGCCGCG TTGCTGGCGT
 9401  TTTTCCATAG GCTCCGCCCC CCTGACGAGC ATCACAAAAA
       TCGACGCTCA AGTCAGAGGT GGCGAAACCC GACAGGACTA
       TAAAGATACC AGGCGTTTCC
 9501  CCCTGGAAGC TCCCTCGTGC GCTCTCCTGT TCCGACCCTG
       CCGCTTACCG GATACCTGTC CGCCTTTCTC CCTTCGGGAA
       GCGTGGCGCT TTCTCATAGC
 9601  TCACGCTGTA GGTATCTCAG TTCGGTGTAG GTCGTTCGCT
       CCAAGCTGGG CTGTGTGCAC GAACCCCCCG TTCAGCCCGA
       CCGCTGCGCC TTATCCGGTA
 9701  ACTATCGTCT TGAGTCCAAC CCGGTAAGAC ACGACTTATC
       GCCACTGGCA GCAGCCACTG GTAACAGGAT TAGCAGAGCG
       AGGTATGTAG GCGGTGCTAC
 9801  AGAGTTCTTG AAGTGGTGGC CTAACTACGG CTACACTAGA
       AGGACAGTAT TTGGTATCTG CGCTCTGCTG AAGCCAGTTA
       CCTTCGGAAA AAGAGTTGGT
 9901  AGCTCTTGAT CCGGCAAACA AACCACCGCT GGTAGCGGTG
       GTTTTTTTGT TTGCAAGCAG CAGATTACGC GCAGAAAAAA
       AGGATCTCAA GAAGATCCTT
10001  TGATCTTTTC TACGGGGTCT GACGCTCAGT GGAACGAAAA
       CTCACGTTAA GGGATTTTGG TCATGAGATT ATCAAAAAGG
       ATCTTCACCT AGATCCTTTT
10101  AAATTAAAAA TGAAGTTTTA AATCAATCTA AGTATATAT
       GAGTAAACTT GGTCTGACAG TTACCAATGC TTAATCAGTG
       AGGCACCTAT CTCAGCGATC
10201  TGTCTATTTC GTTCATCCAT AGTTGCCTGA CTCCCCGTCG
       TGTAGATAAC TACGATACGG GAGGGCTTAC CATCTGGCCC
       CAGTGCTGCA ATGATACCGC
10301  GAGACCCACG CTCACCGGCT CCAGATTTAT CAGCAATAAA
       CCAGCCAGCC GGAAGGGCCG AGCGCAGAAG TGGTCCTGCA
       ACTTTATCCG CCTCCATCCA
10401  GTCTATTAAT TGTTGCCGGG AAGCTAGAGT AAGTAGTTCG
       CCAGTTAATA GTTTGCGCAA CGTTGTTGCC ATTGCTACAG
       GCATCGTGGT GTCACGCTCG
10501  TCGTTTGGTA TGGCTTCATT CAGCTCCGGT TCCCAACGAT
       CAAGGCGAGT TACATGATCC CCCATGTTGT GCAAAAAAGC
       GGTTAGCTCC TTCGGTCCTC
10601  CGATCGTTGT CAGAAGTAAG TTGGCCGCAG TGTTATCACT
       CATGGTTATG GCAGCACTGC ATAATTCTCT TACTGTCATG
       CCATCCGTAA GATGCTTTTC
10701  TGTGACTGGT GAGTACTCAA CCAAGTCATT CTGAGAATAG
       TGTATGCGGC GACCGAGTTG CTCTTGCCCG GCGTCAATAC
       GGGATAATAC CGCGCCACAT
10801  AGCAGAACTT TAAAAGTGCT CATCATTGGA AAACGTTCTT
       CGGGGCGAAA ACTCTCAAGG ATCTTACCGC TGTTGAGATC
       CAGTTCGATG TAACCCACTC
```

FIG 8B CONT.

```
10901   GTGCACCCAA CTGATCTTCA GCATCTTTTA CTTTCACCAG
        CGTTTCTGGG TGAGCAAAAA CAGGAAGGCA AAATGCCGCA
        AAAAAGGGAA TAAGGGCGAC
11001   ACGGAAATGT TGAATACTCA TACTCTTCCT TTTTCAATAT
        TATTGAAGCA TTTATCAGGG TTATTGTCTC ATGAGCGGAT
        ACATATTTGA ATGTATTTAG
11101   AAAAATAAAC AAATAGGGGT TCCGCGCACA TTTCCCCGAA
        AAGTGCCACC TGACGTCTAA GAAACCATTA TTATCATGAC
        ATTAACCTAT AAAAATAGGC
11201   GTATCACGAG GCCCTTTCGT CTCGCGCGTT TCGGTGATGA
        CGGTGAAAAC CTCTGACACA TGCAGCTCCC GGAGACGGTC
        ACAGCTTGTC TGTAAGCGGA
11301   TGCCGGGAGC AGACAAGCCC GTCAGGGCGC GTCAGCGGGT
        GTTGGCGGGT GTCGGGCTG GCTTAACTAT GCGGCATCAG
        AGCAGATTGT ACTGAGAGTG
11401   CACCATATGC GGTGTGAAAT ACCGCACAGA TGCGTAAGGA
        GAAAATACCG CATCAGGCGC CATTCGCCAT TCAGGCTGCG
        CAACTGTTGG GAAGGGCGAT
11501   CGGTGCGGGC CTCTTCGCTA TTACGCCAGC TGGCGAAAGG
        GGGATGTGCT GCAAGGCGAT TAAGTTGGGT AACGCCAGGG
        TTTTCCCAGT CACGACGTTG
11601   TAAAACGACG GCCAGTGAAT TACACCGGTG TGATCATGGG CCG
```

FIG 8B CONT.

atgaagatgagacgctacaagctctttctcatgttctgtatggccggcctgtgcctcatctccttcctgcacttcttcaagaccct
gtcctatgtcaccttcccccgagaactggcctccctcagccctaacctggtgtccagcttttctggaacaatgccccggtca
cgcccaggccagccccgagccaggaggccctgacctgctgcgtaccccactctactcccactcgcccctgctgcagcc
gctgccgcccagcaaggcggccgaggagctccaccgggtggacttggtgctgcccgaggacaccaccgagtatttcgt
gcgcaccaaggccggcggcgtctgcttcaaacccggcaccaagatgctggagaggccgcccccgggacggccggag
gagaagcctgaggggggccaacggctcctcggcccggcggccaccccggtacctcctgagcgcccgggagcgcacgg
ggggccgaggcgcccggcgcaagtgggtggagtgcgtgtgcctgcccggctggcacggacccagctgcggcgtgcc
cactgtggtgcagtactccaacctgcccaccaaggagcggctggtgcccagggaggtgccgcgccgcgtcatcaacgc
catcaacgtcaaccacgagttcgacctgctggacgtgcgcttccacgagctgggcgacgtggtggacgcctttgtggtgtg
cgagtccaacttcacggcttatggggagccgcggccgctcaagttccgggagatgctgaccaatggcaccttcgagtaca
tccgccacaaggtgctctatgtcttcctggaccacttcccgcccggcggccggcaggacggctggatcgccgacgactac
ctgcgcaccttcctcacccaggacggcgtctcgcggctgcgcaacctgcggcccgacgacgtcttcatcattgacgatgc
ggacgagatcccggcccgtgacggcgtccttttcctcaagctctacgatggctggaccgagcccttcgccttccacatgcg
caagtcgctctacggcttcttctggaagcagccgggcaccctggaggtggtgtcaggctgcacggtggacatgctgcagg
cagtgtatgggctggacggcatccgcctgcgccgccgccagtactacaccatgcccaacttcagacagtatgagaaccgc
accggccacatcctggtgcagtggtcgctgggcagccccctgcacttcgccggctggcactgctcctggtgcttcacgcc
cgagggcatctacttcaagctcgtgtccgcccagaatggcgacttcccacgctggggtgactacgaggacaagcgggac
ctgaactacatccgcggcctgatccgcaccggggctggttcgacggcacgcagcaggagtacccgcctgcagacccc
agcgagcacatgtatgcgcccaagtacctgctgaagaactacgaccggttccactacctgctggacaaccctaccagga
gcccaggagcacggcggcgggcgggtggcgccacaggggtcccgagggaaggccgcccgcccggggcaaactgg
acgaggcggaagtctag

FIG. 10

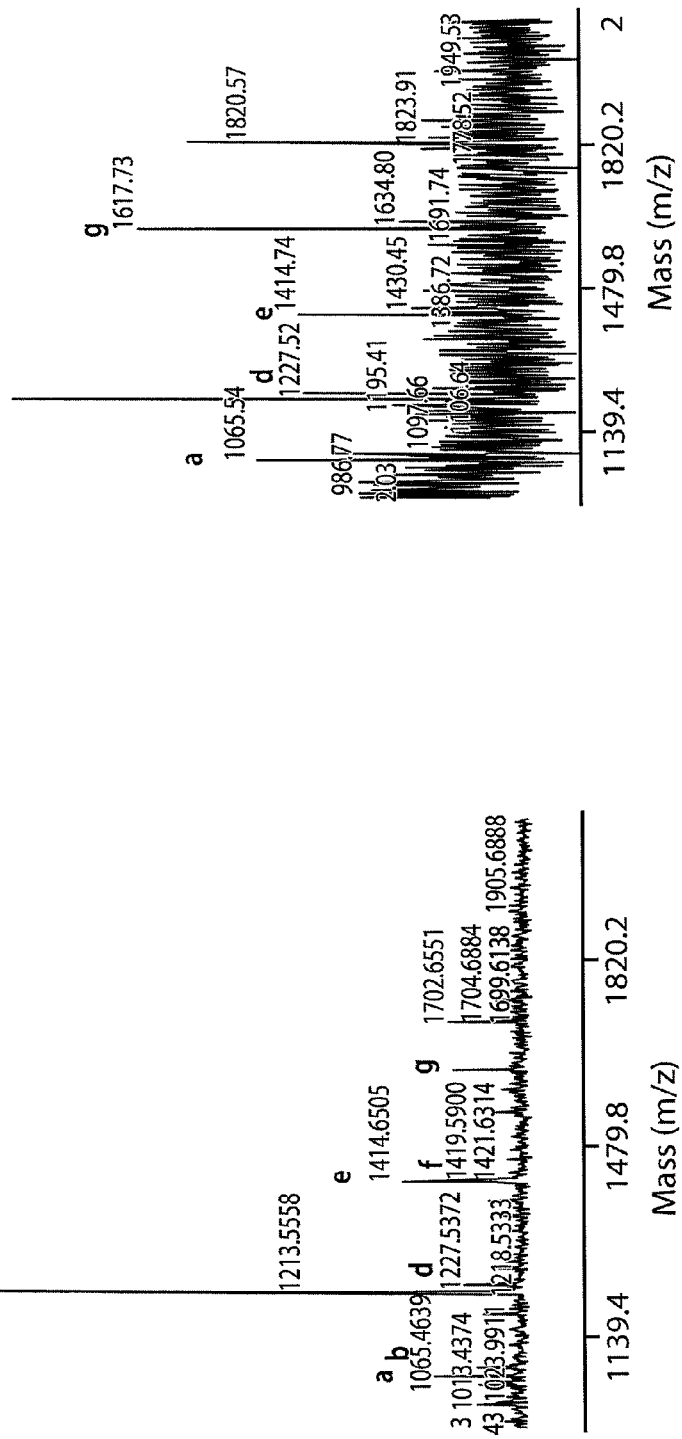

SEQUENCE LISTING

<160> NUMBER OF SEQ ID NOS: 34

<210> SEQ ID NO 1
<211> LENGTH: 1593
<212> TYPE: DNA
<213> ORGANISM: Homo sapiens

<400> SEQUENCE: 1

```
atgagacgct acaagctctt tctcatgttc tgtatggccg gcctgtgcct catctccttc      60
ctgcacttct tcaagaccct gtcctatgtc accttccccc gagaactggc ctccctcagc     120
cctaacctgg tgtccagctt tttctggaac aatgccccgg tcacgcccca ggccagcccc     180
gagccaggag gccctgacct gctgcgtacc ccactctact cccactcgcc cctgctgcag     240
ccgctgccgc ccagcaaggc ggccgaggag ctccaccggg tggacttggt gctgcccgag     300
gacaccaccg agtatttcgt gcgcaccaag gccggcggcg tctgcttcaa acccggcacc     360
aagatgctgg agaggccgcc cccgggacgg ccggaggaga agcctgaggg ggccaacggc     420
tcctcggccc ggcggccacc ccggtacctc ctgagcgccc gggagcgcac gggggccga      480
ggcgcccggc gcaagtgggt ggagtgcgtg tgcctgcccg gctggcacgg acccagctgc     540
ggcgtgccca ctgtggtgca gtactccaac ctgcccacca aggagcggct ggtgcccagg     600
gaggtgccgc gccgcgtcat caacgccatc aacgtcaacc acgagttcga cctgctggac     660
gtgcgcttcc acgagctggg cgacgtggtg gacgcctttg tggtgtgcga gtccaacttc     720
acggcttatg gggagccgcg gccgctcaag ttccgggaga tgctgaccaa tggcaccttc     780
gagtacatcc gccacaaggt gctctatgtc ttcctggacc acttcccgcc cggcggccgg     840
caggacggct ggatcgccga cgactacctg cgcaccttcc tcacccagga cggcgtctcg     900
cggctgcgca acctgcggcc cgacgacgtc ttcatcattg acgatgcgga cgagatcccg     960
```

```
gcccgtgacg gcgtcctttt cctcaagctc tacgatggct ggaccgagcc cttcgccttc    1020
cacatgcgca agtcgctcta cggcttcttc tggaagcagc cgggcaccct ggaggtggtg    1080
tcaggctgca cggtggacat gctgcaggca gtgtatgggc tggacggcat ccgcctgcgc    1140
cgccgccagt actacaccat gcccaacttc agacagtatg agaaccgcac cggccacatc    1200
ctggtgcagt ggtcgctggg cagccccctg cacttcgccg gctggcactg ctcctggtgc    1260
ttcacgcccg agggcatcta cttcaagctc gtgtccgccc agaatggcga cttcccacgc    1320
tggggtgact acgaggacaa gcgggacctg aactacatcc gcggcctgat ccgcaccggg    1380
ggctggttcg acggcacgca gcaggagtac ccgcctgcag accccagcga gcacatgtat    1440
gcgcccaagt acctgctgaa gaactacgac cggttccact acctgctgga caaccctac     1500 caggagccca ggagcacggc ggcgggcggg tggcgccaca ggggtcccga gggaaggccg    1560
cccgcccggg gcaaactgga cgaggcggaa gtc                                 1593
```

<210> SEQ ID NO 2
<211> LENGTH: 531
<212> TYPE: PRT
<213> ORGANISM: Homo sapiens

<400> SEQUENCE: 2

```
Met Arg Arg Tyr Lys Leu Phe Leu Met Phe Cys Met Ala Gly Leu Cys
1               5                   10                  15

Leu Ile Ser Phe Leu His Phe Lys Thr Leu Ser Tyr Val Thr Phe
            20                  25                  30

Pro Arg Glu Leu Ala Ser Leu Ser Pro Asn Leu Val Ser Phe Phe
        35                  40                  45

Trp Asn Asn Ala Pro Val Thr Pro Gln Ala Ser Pro Glu Pro Gly Gly
    50                  55                  60

Pro Asp Leu Leu Arg Thr Pro Leu Tyr Ser His Ser Pro Leu Leu Gln
65                  70                  75                  80

Pro Leu Pro Pro Ser Lys Ala Ala Glu Glu Leu His Arg Val Asp Leu
                85                  90                  95

Val Leu Pro Glu Asp Thr Thr Glu Tyr Phe Val Arg Thr Lys Ala Gly
            100                 105                 110

Gly Val Cys Phe Lys Pro Gly Thr Lys Met Leu Glu Arg Pro Pro
        115                 120                 125

Gly Arg Pro Glu Glu Lys Pro Glu Gly Ala Asn Gly Ser Ser Ala Arg
    130                 135                 140

Arg Pro Pro Arg Tyr Leu Leu Ser Ala Arg Glu Arg Thr Gly Gly Arg
145                 150                 155                 160

Gly Ala Arg Arg Lys Trp Val Glu Cys Val Cys Leu Pro Gly Trp His
                165                 170                 175

Gly Pro Ser Cys Gly Val Pro Thr Val Val Gln Tyr Ser Asn Leu Pro
            180                 185                 190

Thr Lys Glu Arg Leu Val Pro Arg Glu Val Pro Arg Val Ile Asn
        195                 200                 205

Ala Ile Asn Val Asn His Glu Phe Asp Leu Leu Asp Val Arg Phe His
    210                 215                 220

Glu Leu Gly Asp Val Val Asp Ala Phe Val Val Cys Glu Ser Asn Phe
225                 230                 235                 240

Thr Ala Tyr Gly Glu Pro Arg Pro Leu Lys Phe Arg Glu Met Leu Thr
                245                 250                 255

Asn Gly Thr Phe Glu Tyr Ile Arg His Lys Val Leu Tyr Val Phe Leu
            260                 265                 270
```

Asp His Phe Pro Pro Gly Gly Arg Gln Asp Gly Trp Ile Ala Asp Asp
                275                 280                 285

Tyr Leu Arg Thr Phe Leu Thr Gln Asp Gly Val Ser Arg Leu Arg Asn
        290                 295                 300

Leu Arg Pro Asp Val Phe Ile Ile Asp Ala Asp Glu Ile Pro
305                 310                 315                 320

Ala Arg Asp Gly Val Leu Phe Leu Lys Leu Tyr Asp Gly Trp Thr Glu
                325                 330                 335

Pro Phe Ala Phe His Met Arg Lys Ser Leu Tyr Gly Phe Phe Trp Lys
                340                 345                 350

Gln Pro Gly Thr Leu Glu Val Val Ser Gly Cys Thr Val Asp Met Leu
            355                 360                 365

Gln Ala Val Tyr Gly Leu Asp Gly Ile Arg Leu Arg Arg Arg Gln Tyr
        370                 375                 380

Tyr Thr Met Pro Asn Phe Arg Gln Tyr Glu Asn Arg Thr Gly His Ile
385                 390                 395                 400

Leu Val Gln Trp Ser Leu Gly Ser Pro Leu His Phe Ala Gly Trp His
                405                 410                 415

Cys Ser Trp Cys Phe Thr Pro Glu Gly Ile Tyr Phe Lys Leu Val Ser
                420                 425                 430

Ala Gln Asn Gly Asp Phe Pro Arg Trp Gly Asp Tyr Glu Asp Lys Arg
            435                 440                 445

Asp Leu Asn Tyr Ile Arg Gly Leu Ile Arg Thr Gly Gly Trp Phe Asp
        450                 455                 460

Gly Thr Gln Gln Glu Tyr Pro Pro Ala Asp Pro Ser Glu His Met Tyr
465                 470                 475                 480

Ala Pro Lys Tyr Leu Leu Lys Asn Tyr Asp Arg Phe His Tyr Leu Leu
                485                 490                 495

Asp Asn Pro Tyr Gln Glu Pro Arg Ser Thr Ala Ala Gly Gly Trp Arg
            500                 505                 510

His Arg Gly Pro Glu Gly Arg Pro Pro Ala Arg Gly Lys Leu Asp Glu
        515                 520                 525

Ala Glu Val
    530

<210> SEQ ID NO 3
<211> LENGTH: 31
<212> TYPE: DNA
<213> ORGANISM: Artificial Sequence
<220> FEATURE:
<223> OTHER INFORMATION: Synthetic

<400> SEQUENCE: 3
atactcgagt taacaatgaa gatgagacgc t                           31

<210> SEQ ID NO 4
<211> LENGTH: 35
<212> TYPE: DNA
<213> ORGANISM: Artificial Sequence
<220> FEATURE:
<223> OTHER INFORMATION: Synthetic

<400> SEQUENCE: 4
tatggatcct aattcagatc ctcttctgag atgag                       35

<210> SEQ ID NO 5
<211> LENGTH: 20
<212> TYPE: DNA
<213> ORGANISM: Artificial Sequence

```
<220> FEATURE:
<223> OTHER INFORMATION: Synthetic

<400> SEQUENCE: 5
ccatggtgat gagacgctac                                                       20

<210> SEQ ID NO 6
<211> LENGTH: 32
<212> TYPE: DNA
<213> ORGANISM: Artificial Sequence
<220> FEATURE:
<223> OTHER INFORMATION: Synthetic

<400> SEQUENCE: 6
gtttaaacct aggatcctaa ttcagatcct ct                                         32

<210> SEQ ID NO 7
<211> LENGTH: 1602
<212> TYPE: DNA
<213> ORGANISM: Homo sapiens

<400> SEQUENCE: 7
atgaagatga gacgctacaa gctctttctc atgttctgta tggccggcct gtgcctcatc           60
tccttcctgc acttcttcaa gaccctgtcc tatgtcacct tccccgaga actggcctcc          120 ctcagcccta acctggtgtc cagcttttt c tggaacaatg ccccggtcac gccccaggcc         180
agccccgagc caggaggccc tgacctgctg cgtaccccac tctactccca ctcgcccctg         240
ctgcagccgt gccgcccag caaggcgccc gaggagctcc accgggtgga cttggtgctg          300
cccgaggaca ccaccgagta tttcgtgcgc accaaggccg gcggcgtctg cttcaaaccc         360
ggcaccaaga tgctggagag gccgcccccg ggacggccgg aggagaagcc tgagggggcc         420
aacggctcct cggcccggcg gccacccc gg tacctcctga gcgcccggga gcgcacgggg         480
ggccgaggcg cccggcgcaa gtgggtggag tgcgtgtgcc tgcccggctg cacggaccc          540 agctgcggcg tgcccactgt ggtgcagtac tccaacctgc ccaccaagga gcggctggtg         600
cccagggagg tgcgcgccg cgtcatcaac gccatcaacg tcaaccacga gttcgacctg          660
ctggacgtgc gcttccacga gctgggcgac gtggtggacg cctttgtggt gtgcgagtcc         720
aacttcacgg cttatgggga gccgcggccg ctcaagttcc gggagatgct gaccaatggc         780
accttcgagt acatccgcca aaggtgctc tatgtcttcc tggaccactt cccgcccggc          840
ggccggcagg acggctggat cgccgacgac tacctgcgca ccttcctcac ccaggacggc         900
gtctcgcggc tgcgcaacct gcggcccgac gacgtcttca tcattgacga tgcggacgag         960
atcccggccc gtgacggcgt cctttttcctc aagctctacg atggctggac cgagcccttc        1020
gccttccaca tgcgcaagtc gctctacggc ttcttctgga gcagccgggg caccctggag        1080
gtggtgtcag gctgcacggt ggacatgctg caggcagtgt atgggctgga cggcatccgc        1140
ctgcgccgcc gccagtacta ccatgcccc aacttcagac agtatgagaa ccgcaccggc         1200
cacatcctgg tgcagtggtc gctgggcagc ccctgcact cgccggctg gcactgctcc          1260 tggtgcttca cgcccgaggg catctacttc aagctcgtgt ccgcccagaa tggcgacttc        1320
ccacgctggg gtgactacga ggacaagcgg gacctgaact acatccgcgg cctgatccgc        1380 accggggct ggttcgacgg cacgcagcag gagtacccgc ctgcagaccc cagcgagcac         1440
atgtatgcgc caagtacct gctgaagaac tacgaccggt tccactacct gctggacaac        1500
ccctaccagg agcccaggag cacggcggcg ggcggtggc gccacagggg tcccgaggga        1560
aggccgcccg ccgggcaa actggacgag gcggaagtct ag                            1602
```

```
<210> SEQ ID NO 8
<211> LENGTH: 7027
<212> TYPE: DNA
<213> ORGANISM: Artificial Sequence
<220> FEATURE:
<223> OTHER INFORMATION: Synthetic

<400> SEQUENCE: 8
catgattacg ccaagctagc ggccgcattc ccgggaagct aggccaccgt ggcccgcctg      60
caggggaagc ttgcatgcct gcagatcccc ggggatcctc tagagtcgac ctgcagtgca     120
gcgtgacccg gtcgtgcccc tctctagaga taatgagcat tgcatgtcta agttataaaa     180
aattaccaca tattttttttt gtcacacttg tttgaagtgc agtttatcta tctttataca    240
tatatttaaa ctttaatcta cgaataatat aatctatagt actacaataa tatcagtgtt    300
ttagagaatc atataaatga acagttagac atggtctaaa ggacaattga gtattttgac    360
aacaggactc tacagtttta tcttttttagt gtgcatgtgt tctccttttt ttttgcaaat    420
agcttcacct atataatact tcatccattt tattagtaca tccatttagg gtttaggttt    480
aatggttttt atagactaat tttttttagta catctatttt attctatttt agcctctaaa    540
ttaagaaaac taaaactcta ttttagtttt tttatttaat aatttagata taaaatagaa    600
taaaataaag tgactaaaaa ttaaacaaat acccttttaag aaattaaaaa aactaaggaa    660
acatttttct tgtttcgagt agataatgcc agcctgttaa acgccgtcga cgagtctaac    720
ggacaccaac cagcgaacca gcagcgtcgc gtcgggccaa gcgaagcaga cggcacggca    780
tctctgtcgc tgcctctgga cccctctcga gagttccgct ccaccgttgg acttgctccg    840
ctgtcggcat ccagaaattg cgtggcggag cggcagacgt gagccggcac ggcaggcggc    900
ctcctcctcc tctcacggca cggcagctac ggggggattcc tttcccaccg ctccttcgct    960
ttcccttcct cgcccgccgt aataaataga caccccctcc acacctcttt tccccaacct   1020
cgtgttgttc ggagcgcaca cacacacaac cagatctccc ccaaatccac ccgtcggcac   1080
ctccgcttca aggtacgccg ctcgtcctcc cccccccccc ctctctacct tctctagatc   1140
ggcgttccgg tccatgcatg gttagggccc ggtagttcta cttctgttca tgtttgtgtt   1200
agatccgtgt ttgtgttaga tccgtgctgc tagcgttcgt acacggatgc gacctgtacg   1260
tcagacacgt tctgattgct aacttgccag tgtttctctt tggggaatcc tgggatggct   1320
ctagccgttc cgcagacggg atcgatttca tgatttttttt tgtttcgttg catagggttt   1380
ggtttgccct tttcctttat ttcaatatat gccgtgcact tgtttgtcgg tcatcttttt   1440
catgcttttt tttgtcttgg ttgtgatgat gtggtctggt tgggcggtcg ttctagatcg   1500
gagtagaatt ctgtttcaaa ctacctggtg gatttattaa ttttggatct gtatgtgtgt   1560
gccatacata ttcatagtta cgaattgaag atgatggatg gaaatatcga tctaggatag   1620
gtatacatgt tgatgcgggt tttactgatg catatacaga gatgcttttt gttcgcttgg   1680
ttgtgatgat gtggtgtggt tgggcggtcg ttcattcgtt ctagatcgga gtagaatact   1740
gtttcaaact acctggtgta tttattaatt ttggaactgt atgtgtgtgt catacatctt   1800
catagttacg agtttaagat ggatggaaat atcgatctag gataggtata catgttgatg   1860
tgggttttac tgatgcatat acatgatggc atatgcagca tctattcata tgctctaacc   1920
ttgagtacct atctattata ataaacaagt atgttttata attattttga tcttgatata   1980
cttggatgat ggcatatgca gcagctatat gtggattttt tagccctgc cttcatacgc    2040 tatttatttg cttggtactg tttctttttgt cgatgctcac cctgttgttt ggtgttactt    2100
ctgcagggta cccccgggt cgaccatggt aaggggcagc caccaccacc accaccacat   2160
```

-continued

```
ggtccgtcct gtagaaaccc caacccgtga atcaaaaaa ctcgacggcc tgtgggcatt    2220
cagtctggat cgcgaaaact gtggaattga tcagcgttgg tgggaaagcg cgttacaaga    2280
aagccgggca attgctgtgc caggcagttt taacgatcag ttcgccgatg cagatattcg    2340
taattatgcg ggcaacgtct ggtatcagcg cgaagtcttt ataccgaaag gttgggcagg    2400
ccagcgtatc gtgctgcgtt tcgatgcggt cactcattac ggcaaagtgt gggtcaataa    2460
tcaggaagtg atggagcatc agggcggcta tacgccattt gaagccgatg tcacgccgta    2520
tgttattgcc gggaaaagtg tacgtatcac cgtttgtgtg aacaacgaac tgaactggca    2580
gactatcccg ccgggaatgg tgattaccga cgaaaacggc aagaaaaagc agtcttactt    2640
ccatgatttc tttaactatg ccggaatcca tcgcagcgta atgctctaca ccacgccgaa    2700
cacctgggtg gacgatatca ccgtggtgac gcatgtcgcg caagactgta accacgcgtc    2760
tgttgactgg caggtggtgg ccaatggtga tgtcagcgtt gaactgcgtg atgcggatca    2820
acaggtggtt gcaactggac aaggcactag cgggactttg caagtggtga atccgcacct    2880
ctggcaaccg ggtgaaggtt atctctatga actgtgcgtc acagccaaaa gccagacaga    2940
gtgtgatatc tacccgcttc gcgtcggcat ccggtcagtg gcagtgaagg cgaacagtt     3000 cctgattaac cacaaaccgt tctactttac tggctttggt cgtcatgaag atgcggactt    3060
acgtggcaaa ggattcgata acgtgctgat ggtgcacgac cacgcattaa tggactggat    3120
tggggccaac tcctaccgta cctcgcatta cccttacgct gaagagatgc tcgactgggc    3180
agatgaacat ggcatcgtgg tgattgatga aactgctgct gtcggctttta acctctcttt    3240 aggcattggt ttcgaagcgg gcaacaagcc gaaagaactg tacagcgaag aggcagtcaa    3300
cggggaaact cagcaagcgc acttacaggc gattaaagag ctgatagcgc gtgacaaaaa    3360
ccacccaagc gtggtgatgt ggagtattgc caacgaaccg gatacccgtc cgcaagtgca    3420
cgggaatatt tcgccactgg cggaagcaac gcgtaaactc gacccgacgc gtccgatcac    3480
ctgcgtcaat gtaatgttct gcgacgctca caccgatacc atcagcgatc tctttgatgt    3540
gctgtgcctg aaccgttatt acggatggta tgtccaaagc ggcgatttgg aaacggcaga    3600
gaaggtactg aaaaagaac ttctggcctg caggagaaa ctgcatcagc cgattatcat     3660
caccgaatac ggcgtggata cgttagccgg gctgcactca atgtacaccg acatgtggag    3720
tgaagagtat cagtgtgcat ggctggatat gtatcaccgc gtctttgatc gcgtcagcgc    3780
cgtcgtcggt gaacaggtat ggaatttcgc cgattttgcg acctcgcaag gcatattgcg    3840
cgttggcggt aacaagaaag ggatcttcac tcgcgaccgc aaaccgaagt cggcggcttt    3900
tctgctgcaa aaacgctgga ctggcatgaa cttcggtgaa aaaccgcagc agggaggcaa    3960
acaatgataa tgagctcgtt taaactgagg gcactgaagt cgcttgatgt gctgaattgt    4020
ttgtgatgtt ggtggcgtat tttgtttaaa taagtaagca tggctgtgat tttatcatat    4080
gatcgatctt tggggtttta tttaacacat tgtaaaatgt gtatctatta ataactcaat    4140
gtataagatg tgttcattct tcggttgcca tagatctgct tatttgacct gtgatgtttt    4200
gactccaaaa accaaaatca caactcaata aactcatgga atatgtccac ctgtttcttg    4260
aagagttcat ctaccattcc agttggcatt tatcagtgtt gcagcggcgc tgtgcttgt     4320 aacataacaa ttgttacggc atatatccaa cggccggcct agctagccac ggtggccaga    4380
tccactagtt ctagagcggc cgcttaattc actggccgtc gttttacaac gtcgtgactg    4440
ggaaaaccct ggcgttaccc aacttaatcg ccttgcagca catccccctt tcgccagctg    4500
gcgtaatagc gaagaggccc gcaccgatcg cccttcccaa cagttgcgca gcctgaatgg    4560
```

```
cgaatggcgc ctgatgcggt attttctcct tacgcatctg tgcggtattt cacaccgcat   4620
atggtgcact ctcagtacaa tctgctctga tgccgcatag ttaagccagc ccgacaccc    4680 gccaacaccc gctgacgcgc cctgacgggc ttgtctgctc ccggcatccg cttacagaca   4740
agctgtgacc gtctccggga gctgcatgtg tcagaggttt tcaccgtcat caccgaaacg   4800
cgcgagacga aagggcctcg tgatacgcct attttatag gttaatgtca tgataataat    4860
ggtttcttag acgtcaggtg gcacttttcg gggaaatgtg cgcggaaccc ctatttgttt   4920 attttctaa atacattcaa atatgtatcc gctcatgaga caataaccct gataaatgct    4980
tcaataatat tgaaaaagga gagtatgag tattcaacat ttccgtgtcg cccttattcc    5040
cttttttgcg gcattttgcc ttcctgtttt tgctcaccca gaaacgctgg tgaaagtaaa   5100
agatgctgaa gatcagttgg gtgcacgagt gggttacatc gaactggatc tcaacagcgg   5160
taagatcctt gagagttttc gccccgaaga acgttttcca atgatgagca cttttaaagt   5220
tctgctatgt ggcgcggtat tatcccgtat tgacgccggg caagagcaac tcggtcgccg   5280
catacactat tctcagaatg acttggttga gtactcacca gtcacagaaa agcatcttac   5340
ggatggcatg acagtaagag aattatgcag tgctgccata accatgagtg ataacactgc   5400
ggccaactta cttctgacaa cgatcggagg accgaaggag ctaaccgctt ttttgcacaa   5460
catgggggat catgtaactc gccttgatcg ttgggaaccg gagctgaatg aagccatacc   5520
aaacgacgag cgtgacacca cgatgcctgt agcaatggca acaacgttgc gcaaactatt   5580
aactggcgaa ctacttactc tagcttcccg gcaacaatta atagactgga tggaggcgga   5640
taaagttgca ggaccacttc tgcgctcggc ccttccggct ggctggttta ttgctgataa   5700
atctggagcc ggtgagcgtg ggtctcgcgg tatcattgca gcactggggc cagatggtaa   5760
gccctcccgt atcgtagtta tctacacgac ggggagtcag gcaactatgg atgaacgaaa   5820
tagacagatc gctgagatag gtgcctcact gattaagcat tggtaactgt cagaccaagt   5880
ttactcatat atactttaga ttgatttaaa acttcatttt taatttaaaa ggatctaggt   5940
gaagatcctt tttgataatc tcatgaccaa atcccttaa cgtgagtttt cgttccactg    6000
agcgtcagac cccgtagaaa agatcaaagg atcttcttga tccttttt ttctgcgcgt     6060 aatctgctgc ttgcaaacaa aaaaaccacc gctaccagcg gtggtttgtt tgccggatca   6120
agagctacca actctttttc cgaaggtaac tggcttcagc agagcgcaga taccaaatac   6180
tgtccttcta gtgtagccgt agttaggcca ccacttcaag aactctgtag caccgcctac   6240
atacctcgct ctgctaatcc tgttaccagt ggctgctgcc agtggcgata agtcgtgtct   6300
taccgggttg gactcaagac gatagttacc ggataaggcg cagcggtcgg gctgaacggg   6360
gggttcgtgc acacagccca gcttggagcg aacgacctac accgaactga gatacctaca   6420
gcgtgagcat tgagaaagcg ccacgcttcc cgaagggaga aaggcggaca ggtatccggt   6480
aagcggcagg gtcggaacag gagagcgcac gagggagctt ccaggggaa acgcctggta    6540 tctttatagt cctgtcgggt ttcgccacct ctgacttgag cgtcgatttt tgtgatgctc   6600
gtcagggggg cggagcctat ggaaaaacgc cagcaacgcg gcctttttac ggttcctggc   6660
cttttgctgg ccttttgctc acatgttctt tcctgcgtta tccctgattc tgtggataa    6720 ccgtattacc gcctttgagt gagctgatac cgctcgccgc agccgaacga ccgagcgcag   6780
cgagtcagtg agcgaggaag cggaagagcg cccaatacgc aaaccgcctc tccccgcgcg   6840
ttggccgatt cattaatgca gctggcacga caggtttccc gactgaaag cgggcagtga    6900 gcgcaacgca attaatgtga gttagctcac tcattaggca ccccaggctt tacactttat   6960
```

-continued

| | |
|---|---|
| gcttccggct cgtatgttgt gtggaattgt gagcggataa caatttcaca caggaaacag | 7020 |
| ctatgac | 7027 |

<210> SEQ ID NO 9
<211> LENGTH: 6818
<212> TYPE: DNA
<213> ORGANISM: Artificial Sequence
<220> FEATURE:
<223> OTHER INFORMATION: Synthetic

<400> SEQUENCE: 9

| | |
|---|---|
| cctgcagatc cccggggatc ctctagagtc gacctgcagt gcagcgtgac ccggtcgtgc | 60 |
| ccctctctag agataatgag cattgcatgt ctaagttata aaaaattacc acatattttt | 120 |
| tttgtcacac ttgtttgaag tgcagtttat ctatctttat acatatattt aaactttaat | 180 |
| ctacgaataa tataatctat agtactacaa taatatcagt gttttagaga atcatataaa | 240 |
| tgaacagtta gacatggtct aaaggacaat tgagtatttt gacaacagga ctctacagtt | 300 |
| ttatcttttt agtgtgcatg tgttctcctt ttttttttgca aatagcttca cctatataat | 360 |
| acttcatcca ttttattagt acatccattt agggtttagg gttaatggtt tttatagact | 420 |
| aattttttta gtacatctat tttattctat tttagcctct aaattaagaa aactaaaact | 480 |
| ctatttttagt ttttttattt aataatttag atataaaata gaataaaata aagtgactaa | 540 |
| aaattaaaca aatacccttt aagaaattaa aaaaactaag gaaacatttt tcttgtttcg | 600 |
| agtagataat gccagcctgt taaacgccgt cgacgagtct aacggacacc aaccagcgaa | 660 |
| ccagcagcgt cgcgtcgggc caagcgaagc agacggcacg gcatctctgt cgctgcctct | 720 |
| ggacccctct cgagagttcc gctccaccgt tggacttgct ccgctgtcgg catccagaaa | 780 |
| ttgcgtggcg gagcggcaga cgtgagccgg cacggcaggc ggcctcctcc tcctctcacg | 840 |
| gcacggcagc tacggggat tccttttccca ccgctcctc gctttccctt cctcgcccgc | 900 |
| cgtaataaat agacaccccc tccacaccct ctttccccaa cctcgtgttg ttcggagcgc | 960 |
| acacacacac aaccagatct cccccaaatc caccgtcgg cacctccgct tcaaggtacg | 1020 |
| ccgctcgtcc tccccccccc cccctctcta ccttctctag atcggcgttc cggtccatgc | 1080 |
| atggttaggg cccggtagtt ctacttctgt tcatgtttgt gttagatccg tgtttgtgtt | 1140 |
| agatccgtgc tgctagcgtt cgtacacgga tgcgacctgt acgtcagaca cgttctgatt | 1200 |
| gctaacttgc cagtgtttct ctttggggaa tcctgggatg gctctagccg ttccgcagac | 1260 |
| gggatcgatt tcatgatttt ttttgtttcg ttgcataggg tttggtttgc ccttttcctt | 1320 |
| tatttcaata tatgccgtgc acttgtttgt cgggtcatct tttcatgctt ttttttgtct | 1380 |
| tggttgtgat gatgtggtct ggttgggcgg tcgttctaga tcggagtaga attctgtttc | 1440 |
| aaactacctg gtggatttat taattttgga tctgtatgtg tgtgccatac atattcatag | 1500 |
| ttacgaattg aagatgatgg atggaaatat cgatctagga taggtataca tgttgatgcg | 1560 |
| ggttttactg atgcatatac agagatgctt tttgttcgct tggttgtgat gatgtggtgt | 1620 |
| ggttgggcgg tcgttcattc gttctagatc ggagtagaat actgtttcaa actacctggt | 1680 |
| gtatttatta attttggaac tgtatgtgtg tgtcatacat cttcatagtt acgagtttaa | 1740 |
| gatggatgga aatatcgatc taggataggt atacatgttg atgtgggttt tactgatgca | 1800 |
| tatacatgat ggcatatgca gcatctattc atatgctcta accttgagta cctatctatt | 1860 |
| ataataaaca agtatgtttt ataattattt tgatcttgat atacttggat gatggcatat | 1920 |
| gcagcagcta tatgtggatt ttttagccc tgccttcata cgctatttat ttgcttggta | 1980 |

```
ctgtttctttt tgtcgatgct caccctgttg tttggtgtta cttctgcagg gtaccccgg    2040 ggtcgaccat ggtgatgaga cgctacaagc tctttctcat gttctgtatg gccggcctgt    2100
gcctcatctc cttcctgcac ttcttcaaga ccctgtccta tgtcaccttc cccgagaac     2160 tggcctccct cagccctaac ctggtgtcca gcttttttctg gaacaatgcc ccggtcacgc   2220
cccaggccag ccccgagcca ggaggccctg acctgctgcg taccccactc tactcccact   2280 cgccctgct gcagccgctg ccgcccagca aggcggccga ggagctccac cgggtggact    2340
tggtgctgcc cgaggacacc accgagtatt tcgtgcgcac caaggccggc ggcgtctgct   2400
tcaaacccgg caccaagatg ctggagaggc ccccccgggg acggccggag gagaagcctg   2460 aggggggccaa cggctcctcg gcccggcggc caccccggta cctcctgagc gcccgggagc  2520
gcacgggggg ccgaggcgcc cggcgcaagt gggtggagtg cgtgtgcctg cccggctggc   2580
acggacccag ctgcggcgtg cccactgtgg tgcagtactc caacctgccc accaaggagc   2640
ggctggtgcc cagggaggtg ccgcgccgcg tcatcaacgc catcaacgtc aaccacgagt   2700
tcgacctgct ggacgtgcgc ttccacgagc tgggcgacgt ggtggacgcc tttgtggtgt   2760
gcgagtccaa cttcacggct tatggggagc gcggccgct caagttccgg gagatgctga    2820
ccaatggcac cttcgagtac atccgccaca aggtgctcta tgtcttcctg gaccacttcc   2880 cgcccgcgg ccggcaggac ggctggatcg ccgacgacta cctgcgcacc ttcctcaccc    2940
aggacggcgt ctcgcggctg cgcaacctgc ggcccgacga cgtcttcatc attgacgatg   3000
cggacgagat cccggcccgt gacggcgtcc ttttcctcaa gctctacgat ggctggaccg   3060
agcccttcgc cttccacatg cgcaagtcgc tctacggctt cttctggaag cagccgggca   3120
ccctggaggt ggtgtcaggc tgcacggtgg acatgctgca ggcagtgtat gggctggacg   3180
gcatccgcct gcgccgccgc cagtactaca ccatgcccaa cttcagacag tatgagaacc   3240
gcaccggcca catcctggtg cagtggtcgc tgggcagccc cctgcacttc gccggctggc   3300
actgctcctg gtgcttcacg cccgagggca tctacttcaa gctcgtgtcc gcccagaatg   3360
gcgacttccc acgctggggt gactacgagg acaagcggga cctgaactac atccgcggcc   3420
tgatccgcac cggggggctgg ttcgacggca cgcagcagga gtaccgcct gcagaccccca   3480 gcgagcacat gtatgcgccc aagtacctgc tgaagaacta cgaccggttc cactacctgc   3540
tggacaaccc ctaccaggag cccaggagca cggcggcggg cgggtggcgc cacagggggtc  3600 ccgagggaag gccgcccgcc cggggcaaac tggacgaggc ggaagtcgaa caaaaactca   3660
tctcagaaga ggatctgaat taggatccta ggtttaaact gagggcactg aagtcgcttg   3720
atgtgctgaa ttgtttgtga tgttggtggc gtattttgtt taaataagta agcatggctg   3780 tgatttatc atatgatcga tctttggggt tttatttaac acattgtaaa atgtgtatct    3840
attaataact caatgtataa gatgtgttca ttcttcggtt gccatagatc tgcttatttg   3900
acctgtgatg ttttgactcc aaaaaccaaa atcacaactc aataaactca tggaatatgt    3960
ccacctgttt cttgaagagt tcatctacca ttccagttgg catttatcag tgttgcagcg   4020
gcgctgtgct ttgtaacata acaattgttc acggcatata ccacggccg gcctagctag   4080 ccacggtggc cagatccact agttctagag cggccgctta attcactggc cgtcgtttta   4140
caacgtcgtg actgggaaaa ccctggcgtt acccaactta atcgccttgc agcacatccc   4200
cctttcgcca gctggcgtaa tagcgaagag gcccgcaccg atcgccttc ccaacagttg    4260 cgcagcctga atggcgaatg gcgcctgatg cggtattttc tccttacgca tctgtgcggt   4320
atttcacacc gcatatggtg cactctcagt acaatctgct ctgatgccgc atagttaagc   4380
```

```
cagccccgac acccgccaac acccgctgac gcgccctgac gggcttgtct gctcccggca    4440
tccgcttaca gacaagctgt gaccgtctcc gggagctgca tgtgtcagag gttttcaccg    4500
tcatcaccga aacgcgcgag acgaaagggc ctcgtgatac gcctattttt ataggttaat    4560
gtcatgataa taatggtttc ttagacgtca ggtggcactt ttcggggaaa tgtgcgcgga    4620
acccctattt gtttattttt ctaaatacat tcaaatatgt atccgctcat gagacaataa    4680
ccctgataaa tgcttcaata atattgaaaa aggaagagta tgagtattca acatttccgt    4740
gtcgccctta ttccctttt  tgcggcattt tgccttcctg ttttctgca  cccagaaacg    4800 ctggtgaaag taaaagatgc tgaagatcag ttgggtgcac gagtgggtta catcgaactg    4860
gatctcaaca gcggtaagat ccttgagagt tttcgccccg aagaacgttt tccaatgatg    4920
agcactttta aagttctgct atgtggcgcg gtattatccc gtattgacgc cgggcaagag    4980
caactcggtc gccgcataca ctattctcag aatgacttgg ttgagtactc accagtcaca    5040
gaaaagcatc ttacggatgg catgacagta agagaattat gcagtgctgc cataaccatg    5100
agtgataaca ctgcggccaa cttacttctg acaacgatcg gaggaccgaa ggagctaacc    5160
gcttttttgc acaacatggg ggatcatgta actcgccttg atcgttggga accggagctg    5220
aatgaagcca taccaaacga cgagcgtgac accacgatgc ctgtagcaat ggcaacaacg    5280
ttgcgcaaac tattaactgg cgaactactt actctagctt cccggcaaca attaatagac    5340
tggatggagg cggataaagt tgcaggacca cttctgcgct cggcccttcc ggctggctgg    5400
tttattgctg ataaatctgg agccggtgag cgtgggtctc gcggtatcat tgcagcactg    5460
gggccagatg gtaagccctc ccgtatcgta gttatctaca cgacggggag tcaggcaact    5520
atggatgaac gaaatagaca gatcgctgag ataggtgcct cactgattaa gcattggtaa    5580
ctgtcagacc aagtttactc atatatactt tagattgatt taaaacttca tttttaattt    5640
aaaaggatct aggtgaagat cctttttgat aatctcatga ccaaaatccc ttaacgtgag    5700
ttttcgttcc actgagcgtc agaccccgta gaaaagatca aaggatcttc ttgagatcct    5760
ttttttctgc gcgtaatctg ctgcttgcaa acaaaaaaac caccgctacc agcggtggtt    5820
tgtttgccgg atcaagagct accaactctt tttccgaagg taactggctt cagcagagcg    5880
cagataccaa atactgtcct tctagtgtag ccgtagttag gccaccactt caagaactct    5940
gtagcaccgc ctacatacct cgctctgcta atcctgttac cagtggctgc tgccagtggc    6000
gataagtcgt gtcttaccgg gttggactca agacgatagt taccggataa ggcgcagcgg    6060
tcgggctgaa cggggggttc gtgcacacag cccagcttgg agcgaacgac ctacaccgaa    6120
ctgagatacc tacagcgtga gcattgagaa agcgccacgc ttcccgaagg gagaaaggcg    6180
gacaggtatc cggtaagcgg cagggtcgga acaggagagc gcacgaggga gcttccaggg    6240
ggaaacgcct ggtatcttta tagtcctgtc gggtttcgcc acctctgact tgagcgtcga    6300
tttttgtgat gctcgtcagg ggggcggagc ctatggaaaa acgccagcaa cgcggccttt    6360
ttacggttcc tggccttttg ctggcctttt gctcacatgt tctttcctgc gttatcccct    6420
gattctgtgg ataaccgtat taccgccttt gagtgagctg ataccgctcg ccgcagccga    6480
acgaccgagc gcagcgagtc agtgagcgag gaagcggaag agcgcccaat acgcaaaccg    6540
cctctccccg cgcgttggcc gattcattaa tgcagctggc acgacaggtt tcccgactgg    6600
aaagcgggca gtgagcgcaa cgcaattaat gtgagttagc tcactcatta ggcaccccag    6660
gctttacact ttatgcttcc ggctcgtatg ttgtgtggaa ttgtgagcgg ataacaattt    6720
```

| | |
|---|---|
| cacacaggaa acagctatga ccatgattac gccaagctag cggccgcatt cccgggaagc | 6780 |
| taggccaccg tggcccgcct gcaggggaag cttgcatg | 6818 |

<210> SEQ ID NO 10
<211> LENGTH: 7545
<212> TYPE: DNA
<213> ORGANISM: Artificial Sequence
<220> FEATURE:
<223> OTHER INFORMATION: Synthetic

<400> SEQUENCE: 10

| | |
|---|---|
| cgattaaaaa tctcaattat atttggtcta atttagtttg gtattgagta aaacaaattc | 60 |
| gaaccaaacc aaaatataaa tatatagttt ttatatatat gcctttaaga cttttttatag | 120 |
| aattttcttt aaaaaatatc tagaaatatt tgcgactctt ctggcatgta atatttcgtt | 180 |
| aaatatgaag tgctccattt ttattaactt taaataattg gttgtacgat cactttctta | 240 |
| tcaagtgtta ctaaaatgcg tcaatctctt tgttcttcca tattcatatg tcaaaaccta | 300 |
| tcaaaattct tatatatctt tttcgaattt gaagtgaaat ttcgataatt taaaattaaa | 360 |
| tagaacatat cattatttag gtatcatatt gattttttata cttaattact aaatttggtt | 420 |
| aactttgaaa gtgtacatca acgaaaaatt agtcaaacga ctaaaataaa taaatatcat | 480 |
| gtgttattaa gaaaattctc ctataagaat attttaatag atcatatgtt tgtaaaaaaa | 540 |
| attaattttt actaacacat atatttactt atcaaaaatt tgacaaagta agattaaaat | 600 |
| aatattcatc taacaaaaaa aaaaccagaa aatgctgaaa acccggcaaa accgaaccaa | 660 |
| tccaaaccga tatagttggt ttggtttgat tttgatataa accgaaccaa ctcggtccat | 720 |
| ttgcacccct aatcataata gctttaatat ttcaagatat tattaagtta acgttgtcaa | 780 |
| tatcctggaa attttgcaaa atgaatcaag cctatatggc tgtaatatga atttaaaagc | 840 |
| agctcgatgt ggtggtaata tgtaatttac ttgattctaa aaaaatatcc caagtattaa | 900 |
| taatttctgc taggaagaag gttagctacg atttacagca aagccagaat acaatgaacc | 960 |
| ataaagtgat tgaagctcga aatatacgaa ggaacaaata ttttttaaaaa aatacgcaat | 1020 |
| gacttggaac aaaagaaagt gatatatttt ttgttcttaa acaagcatcc cctctaaaga | 1080 |
| atggcagttt tcctttgcat gtaactatta tgctcccttc gttacaaaaa ttttggacta | 1140 |
| ctattgggaa cttcttctga aaatagtggc caccgcttaa ttaaggcgcg ccatgcccgg | 1200 |
| gcaagcggcc gcttaattaa atttaaatgt ttaaactagg aaatccaagc ttgggctgca | 1260 |
| ggtcaatccc attgcttttg aagcagctca acattgatct ctttctcgag gtcattcata | 1320 |
| tgcttgagaa gagagtcggg atagtccaaa ataaaacaaa ggtaagatta cctggtcaaa | 1380 |
| agtgaaaaca tcagttaaaa ggtggtataa agtaaaatat cggtaataaa aggtggccca | 1440 |
| aagtgaaatt tactctttttc tactattata aaaattgagg atgttttttgt cggtactttg | 1500 |
| atacgtcatt tttgtatgaa ttggtttttta agtttattcg cttttggaaa tgcatatctg | 1560 |
| tatttgagtc gggttttaag ttcgtttgct tttgtaaata cagagggatt tgtataagaa | 1620 |
| atatctttaa aaaacccat atgctaattt gacataattt ttgagaaaaa tatatattca | 1680 |
| ggcgaattct cacaatgaac aataataaga ttaaaatagc tttcccccgt tgcagcgcat | 1740 |
| gggtattttt tctagtaaaa ataaaagata aacttagact caaacatttt acaaaaacaa | 1800 |
| cccctaaagt tcctaaagcc caagtgctca tccacgatcc atagcaagcc cagcccaacc | 1860 |
| caacccaacc caacccaccc cagtccagcc aactggacaa tagtctccac accccccccac | 1920 |
| tatcaccgtg agttgtccgc acgcaccgca cgtctcgcag ccaaaaaaaa aaaaagaaag | 1980 |

```
aaaaaaaaga aaaagaaaaa acagcaggtg ggtccgggtc gtgggggccg gaaacgcgag    2040
gaggatcgcg agccagcgac gaggccggcc ctccctccgc ttccaaagaa acgccccca     2100 tcgccactat atacataccc ccccctctcc tcccatcccc caaccctac caccaccacc     2160 accaccacct ccacctcctc cccctcgct gccggacgac gcctccccc tccccctccg      2220 ccgccgccgc gccggtaacc accccgcccc tctcctcttt ctttctccgt ttttttttc     2280 cgtctcggtc tcgatctttg gccttggtag tttgggtggg cgagaggcgg cttcgtgcgc    2340
gcccagatcg gtgcgcggga ggggcgggat ctcgcggctg gggctctcgc cggcgtggat    2400
ccggcccgga tctcgcgggg aatgggctc tcggatgtag atctgcgatc cgccgttgtt     2460
gggggagatg atggggggtt taaaatttcc gccatgctaa acaagatcag gaagagggga    2520
aaagggcact atggtttata tttttatata tttctgctgc ttcgtcaggc ttagatgtgc    2580
tagatctttc tttcttcttt ttgtgggtag aatttgaatc cctcagcatt gttcatcggt    2640 agttttctt ttcatgattt gtgacaaatg cagcctcgtg cggagctttt ttgtaggtag     2700
accatggctt ctccggagag gagaccagtt gagattaggc cagctacagc agctgatatg    2760
gccgcggttt gtgatatcgt taaccattac attgagacgt ctacagtgaa ctttaggaca    2820
gagccacaaa caccacaaga gtggattgat gatctagaga ggttgcaaga tagataccct    2880
tggttggttg ctgaggttga gggtgttgtg gctggtattg cttacgctgg gccctggaag    2940
gctaggaacg cttacgattg gacagttgag agtactgttt acgtgtcaca taggcatcaa    3000
aggttgggcc taggatccac attgtacaca catttgctta agtctatgga ggcgcaaggt    3060
tttaagtctg tggttgctgt tataggcctt ccaaacgatc catctgttag gttgcatgag    3120
gctttgggat acacagcccg gggtacattg cgcgcagctg gatacaagca tggtggatgg    3180
catgatgttg gtttttggca aagggatttt gagttgccag ctcctccaag gccagttagg    3240
ccagttaccc agatctgagg tacctgagc tcggtcgcag cgtgtgcgtg tccgtcgtac      3300
gttctggccg gccgggcctt gggcgcgcga tcagaagcgt tgccgttggcg tgtgtgtgct   3360 tctggtttgc tttaattta ccaagtttgt ttcaaggtgg atcgcgtggt caaggcccgt     3420
gtgctttaaa gacccaccgg cactggcagt gagtgttgct gcttgtgtag gctttggtac    3480
gtatgggctt tatttgcttc tggatgttgt gtactacttg ggtttgttga attattatga    3540
gcagttgcgt attgtaattc agctgggcta cctggacatt gttatgtatt aataaatgct    3600
ttgctttctt ctaaagatct ttaagtgctg aattcatatt tcctcctgca gggtttaaac    3660
ttgccgtggc ctattttcag aagaagttcc caatagtagt ccaaattttt tgtaacgaag    3720
ggagcataat agttacatgc aaaggaaaac tgccattctt tagaggggat gcttgtttaa    3780
gaacaaaaaa tatatcactt tcttttgttc caagtcattg cgtattttt taaaaatatt     3840 tgttccttcg tatatttcga gcttcaatca ctttatggtt cttttgtattc tggctttgct   3900 gtaaatcgta gctaaccttc ttcctagcag aaattattaa tacttgggat atttttttag    3960
aatcaagtaa attacatatt accaccacat cgagctgctt ttaaattcat attacagcca    4020
tataggcttg attcattttg caaaattttcc aggatattga caacgttaac ttaataatat   4080
cttgaaatat taaagctatt atgattaggg gtgcaaatgg accgagttgg ttcggtttat    4140
atcaaaatca aaccaaacca actatatcgg tttggattgg ttcggttttg ccgggttttc    4200 agcatttttct ggtttttttt ttgttagatg aatattattt taatcttact ttgtcaaatt   4260
tttgataagt aaatatatgt gttagtaaaa attaattttt tttacaaaca tatgatctat    4320
taaaatattc ttataggaga atttttcttaa taacacatga tatttattta ttttagtcgt   4380
```

```
ttgactaatt tttcgttgat gtacactttc aaagttaacc aaatttagta attaagtata    4440
aaaatcaata tgatacctaa ataatgatat gttctattta atttttaaatt atcgaaattt   4500
cacttcaaat tcgaaaaaga tatataagaa ttttgataga ttttgacata tgaatatgga    4560
agaacaaaga gattgacgca ttttagtaac acttgataag aaagtgatcg tacaaccaat    4620
tatttaaagt taataaaaat ggagcacttc atatttaacg aaatattaca tgccagaaga    4680
gtcgcaaata tttctagata tttttaaag aaaattctat aaaaagtctt aaaggcatat     4740
atataaaaac tatatattta tattttggtt tggttcgaat ttgttttact caataccaaa    4800
ctaaattaga ccaaatataa ttgggatttt taatcgcggc ccactagtca ccggtgtagc    4860
ttggcgtaat catggtcata gctgtttcct gtgtgaaatt gttatccgct cacaattcca    4920
cacaacatac gagccggaag cataaagtgt aaagcctggg gtgcctaatg agtgagctaa    4980
ctcacattaa ttgcgttgcg ctcactgccc gctttccagt cgggaaacct gtcgtgccag    5040
ctgcattaat gaatcggcca acgcgcgggg agaggcggtt tgcgtattgg gcgctcttcc    5100
gctgcgcacg ctgcgcacgc tgcgcacgct tcctcgctca ctgactcgct gcgctcggtc    5160
gttcggctgc ggcgagcggt atcagctcac tcaaaggcgg taatacggtt atccacagaa    5220
tcagggata acgcaggaaa gaacatgtga gcaaaaggcc agcaaaaggc caggaaccgt     5280
aaaaaggccg cgttgctggc gtttttccat aggctccgcc ccctgacga gcatcacaaa     5340
aatcgacgct caagtcagag gtggcgaaac ccgacaggac tataaagata ccaggcgttt    5400
cccctggaa gctccctcgt gcgctctcct gttccgaccc tgccgcttac cggatacctg     5460
tccgccttc tcccttcggg aagcgtggcg ctttctcata gctcacgctg taggtatctc     5520
agttcggtgt aggtcgttcg ctccaagctg ggctgtgtgc acgaaccccc cgttcagccc    5580
gaccgctgcg ccttatccgg taactatcgt cttgagtcca acccggtaag acacgactta    5640
tcgccactgg cagcagccac tggtaacagg attagcagag cgaggtatgt aggcggtgct    5700
acagagttct tgaagtggtg gcctaactac ggctacacta aaggacagt atttggtatc     5760
tgcgctctgc tgaagccagt taccttcgga aaaagagttg gtagctcttg atccggcaaa    5820
caaaccaccg ctggtagcgg tggttttttt gtttgcaagc agcagattac gcgcagaaaa    5880
aaaggatctc aagaagatcc tttgatcttt tctacggggt ctgacgctca gtggaacgaa    5940
aactcacgtt aagggatttt ggtcatgaga ttatcaaaaa ggatcttcac ctagatcctt    6000
ttaaattaaa aatgaagttt taaatcaatc taaagtatat atgagtaaac ttggtctgac    6060
agttaccaat gcttaatcag tgaggcacct atctcagcga tctgtctatt tcgttcatcc    6120
atagttgcct gactccccgt cgtgtagata actacgatac gggagggctt accatctggc    6180
cccagtgctg caatgatacc gcgagaccca cgctcaccgg ctccagattt atcagcaata    6240
aaccagccag ccggaagggc cgagcgcaga agtggtcctg caactttatc cgcctccatc    6300
cagtctatta attgttgccg ggaagctaga gtaagtagtt cgccagttaa tagtttgcgc    6360
aacgttgttg ccattgctac aggcatcgtg gtgtcacgct cgtcgtttgg tatggcttca    6420
ttcagctccg gttcccaacg atcaaggcga gttacatgat ccccatgtt gtgcaaaaaa    6480
gcggttagct ccttcggtcc tccgatcgtt gtcagaagta agttggccgc agtgttatca    6540
ctcatggtta tggcagcact gcataattct cttactgtca tgccatccgt aagatgcttt    6600
tctgtgactg gtgagtactc aaccaagtca ttctgagaat agtgtatgcg gcgaccgagt    6660
tgctcttgcc cggcgtcaat acgggataat accgcgccac atagcagaac tttaaaagtg    6720
ctcatcattg gaaaacgttc ttcggggcga aaactctcaa ggatcttacc gctgttgaga    6780
```

-continued

| | |
|---|---|
| tccagttcga tgtaacccac tcgtgcaccc aactgatctt cagcatcttt tactttcacc | 6840 |
| agcgtttctg ggtgagcaaa acaggaagg caaaatgccg caaaaaggg aataagggcg | 6900 |
| acacggaaat gttgaatact catactcttc cttttcaat attattgaag catttatcag | 6960 |
| ggttattgtc tcatgagcgg atacatattt gaatgtattt agaaaataa acaataggg | 7020 |
| gttccgcgca catttccccg aaaagtgcca cctgacgtct aagaaaccat tattatcatg | 7080 |
| acattaacct ataaaatag gcgtatcacg aggccctttc gtctcgcgcg tttcggtgat | 7140 |
| gacggtgaaa acctctgaca catgcagctc ccggagacgg tcacagcttg tctgtaagcg | 7200 |
| gatgccggga gcagacaagc ccgtcagggc gcgtcagcgg gtgttggcgg gtgtcggggc | 7260 |
| tggcttaact atgcggcatc agagcagatt gtactgagag tgcaccatat gcggtgtgaa | 7320 |
| ataccgcaca gatgcgtaag gagaaaatac cgcatcaggc gccattcgcc attcaggctg | 7380 |
| cgcaactgtt gggaagggcg atcggtgcgg gcctcttcgc tattacgcca gctggcgaaa | 7440 |
| gggggatgtg ctgcaaggcg attaagttgg gtaacgccag ggttttccca gtcacgacgt | 7500 |
| tgtaaaacga cggccagtga attacaccgg tgtgatcatg ggccg | 7545 |

<210> SEQ ID NO 11
<211> LENGTH: 11643
<212> TYPE: DNA
<213> ORGANISM: Artificial Sequence
<220> FEATURE:
<223> OTHER INFORMATION: Synthetic

<400> SEQUENCE: 11

| | |
|---|---|
| cgattaaaaa cccaattata tttggtctaa tttagtttgg tattgagtaa aacaaattcg | 60 |
| aaccaaacca aaatataaat atatagtttt tatatatatg cctttaagac tttttataga | 120 |
| attttcttta aaaatatct agaaatatt gcgactcttc tggcatgtaa tattcgtta | 180 |
| aatatgaagt gctccatttt tattaacttt aaataaттgg ттgтacgатc асттсття | 240 |
| caagtgttac taaaatgcgt caatctcttt gttcttccat attcatatgt caaaatctat | 300 |
| caaaатт стт атататстт тт cgaatttg aagtgaaatt tcgataatt aaaataaat | 360 |
| agaacatatc atatttagg tatcatattg atttatac ttaattacta atttggtta | 420 |
| асттт gaaag tg tacatcaa cgaaaaatta gtcaaacgac taaataaat aaatatcatg | 480 |
| tgttattaag aaaattctcc tataagaata tttta atga tcatatgttt gtaaaaaaaa | 540 |
| ttaattttta ctaacacata tatttactta tcaaaattt gacaaagtaa gattaaaata | 600 |
| atattcatct aacaaaaaaa aaaccagaaa atgctgaaaa cccggcaaaa ccgaaccaat | 660 |
| ccaaaccgat atagttggtt tggtttgatt ttgatataaa ccgaaccaac tcggtccatt | 720 |
| tgcaccccta atcataatag cttt аататт tcaagatatt attaagttaa cgttgtcaat | 780 |
| atcctggaaa tttt gcaaaa tgaatcaagc ctatatggct gtaatatgaa tttaaaagca | 840 |
| gctcgatgtg gtggtaatat gtaattact tgatt ctaaa aaaatatccc aagtattaat | 900 |
| ааттт ctgct aggaagaagg ttagctacga tttacagcaa agccagaata caaagaacca | 960 |
| taaagtgatt gaagctcgaa ататтacgaag gaacaaatat tttt aaaaaa atacgcaatg | 1020 |
| acttggaaca aagaaagtg atatatttt tgttctt aaa caagcatccc ctctaaagaa | 1080 |
| tggcagtttt ccttt gcatg taacttattat gctccctt cg ttacaaaaat tttggactac | 1140 |
| tattgggaat tcttctgaaa atagtggcca ccgctt aatt aaggcgcgcc atgccccctg | 1200 |
| cagatccccg gggatcctct agagtcgacc tgcagtgcag cgtgacccgg tcgtgccct | 1260 |
| ctctagagat aatgagcatt gcatgtctaa gttataaaaa attaccacat attttttttg | 1320 |

```
tcacacttgt ttgaagtgca gtttatctat ctttatacat atatttaaac tttaatctac   1380
gaataatata atctatagta ctacaataat atcagtgttt tagagaatca tataaatgaa   1440
cagttagaca tggtctaaag gacaattgag tattttgaca acaggactct acagttttat   1500 cttttagtg tgcatgtgtt ctccttttt tttgcaaata gcttcaccta tataatactt   1560
catccatttt attagtacat ccatttaggg tttagggtta atggttttta tagactaatt   1620
tttttagtac atctatttta ttctatttta gcctctaaat taagaaaact aaaactctat   1680
tttagttttt ttatttaata atttagatat aaaatagaat aaaataaagt gactaaaaat   1740
taaacaaata cccttaaga aattaaaaaa actaaggaaa catttttctt gtttcgagta   1800
gataatgcca gcctgttaaa cgccgtcgac gagtctaacg gacaccaacc agcgaaccag   1860
cagcgtcgcg tcgggccaag cgaagcagac ggcacggcat ctctgtcgct gcctctggac   1920
ccctctcgag agttccgctc caccgttgga cttgctccgc tgtcggcatc cagaaattgc   1980
gtggcggagc ggcagacgtg agccggcacg gcaggcggcc tcctcctcct ctcacggcac   2040
ggcagctacg ggggattcct ttcccaccgc tccttcgctt tcccttcctc gcccgccgta   2100
ataaatagac ccccctcca caccctctttt ccccaacctc gtgttgttcg gagcgcacac   2160
acacacaacc agatctcccc caaatccacc cgtcggcacc tccgcttcaa ggtacgccgc   2220
tcgtcctccc cccccccc tctctacctt ctctagatcg gcgttccggt ccatgcatgg   2280
ttagggcccg gtagttctac ttctgttcat gtttgtgtta gatccgtgtt tgtgttagat   2340
ccgtgctgct agcgttcgta cacggatgcg acctgtacgt cagacacgtt ctgattgcta   2400
acttgccagt gtttctcttt ggggaatcct gggatggctc tagccgttcc gcagacggga   2460
tcgatttcat gattttttt gtttcgttgc atagggtttg gtttgccctt ttccttatt   2520 tcaatatatg ccgtgcactt gtttgtcggg tcatctttc atgcttttt ttgtcttggt   2580 tgtgatgatg tggtctggtt gggcggtcgt tctagatcgg agtagaattc tgtttcaaac   2640
tacctggtgg atttattaat tttggatctg tatgtgtgtg ccatacatat tcatagttac   2700
gaattgaaga tgatggatgg aaatatcgat ctaggatagg tatacatgtt gatgcgggtt   2760
ttactgatgc atatacagag atgctttttg ttcgcttggt tgtgatgatg tggtgtggtt   2820
gggcggtcgt tcattcgttc tagatcggag tagaatactg tttcaaacta cctggtgtat   2880
ttattaattt tggaactgta tgtgtgtgtc atacatcttc atagttacga gtttaagatg   2940
gatggaaata tcgatctagg ataggtatac atgttgatgt gggttttact gatgcatata   3000
catgatggca tatgcagcat ctattcatat gctctaacct tgagtaccta tctattataa   3060
taaacaagta tgttttataa ttattttgat cttgatatac ttggatgatg gcatatgcag   3120
cagctatatg tggatttttt tagccctgcc ttcatacgct atttatttgc ttggtactgt   3180
ttcttttgtc gatgctcacc ctgttgtttg gtgttacttc tgcagggtac ccccggggtc   3240
gaccatggtg atgagacgct acaagctctt tctcatgttc tgtatggccg gcctgtgcct   3300
catctccttc ctgcacttct tcaagaccct gtcctatgtc accttccccc gagaactggc   3360
ctccctcagc cctaacctgg tgtccagctt tttctggaac aatgcccgg tcacgcccca   3420 ggccagcccc gagccaggag gccctgacct gctgcgtacc ccactctact cccactcgcc   3480
cctgctgcag ccgctgccgc ccagcaaggc ggccgaggag ctccaccggg tggacttggt   3540
gctgcccgag gacaccaccg agtatttcgt gcgcaccaag gccggcgcg tctgcttcaa   3600 acccggcacc aagatgctgg agaggccccc ccgggacgg ccgaggagaa agcctgaggg   3660
ggccaacggc tcctcggccc ggcggccacc ccggtacctc ctgagcgccc gggagcgcac   3720
```

-continued

```
gggggggccga ggcgcccggc gcaagtgggt ggagtgcgtg tgcctgcccg gctggcacgg    3780
acccagctgc ggcgtgccca ctgtggtgca gtactccaac ctgcccacca aggagcggct    3840
ggtgcccagg gaggtgccgc gccgcgtcat caacgccatc aacgtcaacc acgagttcga    3900
cctgctggac gtgcgcttcc acgagctggg cgacgtggtg gacgcctttg tggtgtgcga    3960
gtccaacttc acggcttatg gggagccgcg gccgctcaag ttccgggaga tgctgaccaa    4020
tggcaccttc gagtacatcc gccacaaggt gctctatgtc ttcctggacc acttcccgcc    4080
cggcggccgg caggacggct ggatcgccga cgactacctg cgcaccttcc tcacccagga    4140
cggcgtctcg cggctgcgca acctgcggcc cgacgacgtc ttcatcattg acgatgcgga    4200
cgagatcccg gcccgtgacg gcgtcctttt cctcaagctc tacgatggct ggaccgagcc    4260
cttcgccttc cacatgcgca agtcgctcta cggcttcttc tggaagcagc cgggcaccct    4320
ggaggtggtg tcaggctgca cggtggacat gctgcaggca gtgtatgggc tggacggcat    4380
ccgcctgcgc cgccgccagt actacaccat gcccaacttc agacagtatg agaaccgcac    4440
cggccacatc ctggtgcagt ggtcgctggg cagcccctg cacttcgccg gctggcactg    4500
ctcctggtgc ttcacgcccg agggcatcta cttcaagctc gtgtccgccc agaatgggga    4560
cttcccacgc tggggtgact acgaggacaa gcgggacctg aactacatcc gcggcctgat    4620
ccgcaccggg ggctggttcg acggcacgca gcaggagtac ccgcctgcag accccagcga    4680
gcacatgtat gcgcccaagt acctgctgaa gaactacgac cggttccact acctgctgga    4740
caacccctac caggagccca ggagcacggc ggcgggcggg tggcgccaca ggggtcccga    4800
gggaaggccg cccgcccggg gcaaactgga cgaggcggaa gtcgaacaaa aactcatctc    4860
agaagaggat ctgaattagg atcctaggtt taaactgagg gcactgaagt cgcttgatgt    4920
gctgaattgt ttgtgatgtt ggtggcgtat tttgtttaaa taagtaagca tggctgtgat    4980
tttatcatat gatcgatctt tggggtttta tttaacacat tgtaaaatgt gtatctatta    5040
ataactcaat gtataagatg tgttcattct tcggttgcca tagatctgct tatttgacct    5100
gtgatgtttt gactccaaaa accaaaatca caactcaata aactcatgga atatgtccac    5160
ctgtttcttg aagagttcat ctaccattcc agttggcatt tatcagtgtt gcagcggcgc    5220
tgtgcttgt aacataacaa ttgttcacgg catatatcca cggccggcct agctagccac    5280
ggtggccaga tccactaggg gcaagcggcc gcttaattaa atttaaatgt ttaaactagg    5340
aaatccaagc ttgggctgca ggtcaatccc attgcttttg aagcagctca acattgatct    5400
cttttctcgag gtcattcata tgcttgagaa gagagtcggg atagtccaaa ataaaacaaa    5460
ggtaagatta cctggtcaaa agtgaaaaca tcagttaaaa ggtggtataa agtaaaatat    5520
cggtaataaa aggtggccca aagtgaaatt tactcttttc tactattata aaaattgagg    5580
atgttttgt cggtactttg atacgtcatt tttgtatgaa ttggtttta agtttattcg    5640
cttttggaaa tgcatatctg tatttgagtc gggttttaag ttcgtttgct tttgtaaata    5700
cagagggatt tgtataagaa atatctttaa aaaacccat atgctaattt gacataattt    5760
ttgagaaaaa tatatattca ggcgaattct cacaatgaac aataataaga ttaaaatagc    5820
tttccccgt tgcagcgcat gggtatttt tctagtaaaa ataaaagata aacttagact    5880
caaaacattt acaaaaacaa cccctaaagt tcctaaagcc caagtgcta tccacgatcc    5940
atagcaagcc cagcccaacc caacccaacc caacccaccc cagtccagcc aactggacaa    6000
tagtctccac acccccccac tatcaccgtg agttgtccgc acgcaccgca cgtctcgcag    6060
ccaaaaaaaa aaaagaaag aaaaaaaaga aaagaaaaa acagcaggtg gtccgggtc    6120
```

```
gtgggggccg gaaacgcgag gaggatcgcg agccagcgac gaggccggcc ctccctccgc    6180
ttccaaagaa acgcccccca tcgccactat atacataccc cccctctcc tcccatcccc    6240 ccaaccctac caccaccacc accaccacct ccacctcctc ccccctcgct gccggacgac    6300 gcctccccc tcccctccg ccgccgccgc gccgtaacc accccgcccc tctcctcttt      6360 cttctccgt ttttttttc cgtctcggtc tcgatctttg gccttggtag tttgggtggg     6420 cgagaggcg cttcgtgcgc gcccagatcg gtgcgcggga gggcgggat ctcgcggctg     6480 gggctctcgc cggcgtggat ccggcccgga tctcgcgggg aatgggctc tcggatgtag    6540 atctgcgatc cgccgttgtt gggggagatg atggggggtt taaaatttcc gccatgctaa   6600
acaagatcag gaagagggga aaagggcact atggtttata tttttatata tttctgctgc   6660
ttcgtcaggc ttagatgtgc tagatctttc tttcttcttt ttgtgggtag aatttgaatc   6720
cctcagcatt gttcatcggt agttttctt ttcatgattt gtgacaaatg cagcctcgtg    6780
cggagctttt ttgtaggtag accatggctt ctccggagag gagaccagtt gagattaggc   6840
cagctacagc agctgatatg gccgcggttt gtgatatcgt taaccattac attgagacgt   6900
ctacagtgaa ctttaggaca gagccacaaa caccacaaga gtggattgat gatctagaga   6960
ggttgcaaga tagatacccc tggttggttg ctgaggttga gggtgttgtg gctggtattg   7020
cttacgctgg gccctggaag gctaggaacg cttacgattg gacagttgag agtactgttt   7080
acgtgtcaca taggcatcaa aggttgggcc taggatccac attgtacaca catttgctta   7140
agtctatgga ggcgcaaggt tttaagtctg tggttgctgt tataggcctt ccaaacgatc   7200
catctgttag gttgcatgag gctttgggat acacagcccg gggtacattg cgcgcagctg   7260
gatacaagca tggtggatgg catgatgttg gttttggca aagggatttt gagttgccag    7320
ctcctccaag gccagttagg ccagttaccc agatctgagg taccctgagc tcggtcgcag   7380
cgtgtgcgtg tccgtcgtac gttctggccg gccgggcctt gggcgcgcga tcagaagcgt   7440
tgcgttggcg tgtgtgtgct tctggttttgc tttaatttta ccaagtttgt ttcaaggtgg   7500
atcgcgtggt caaggcccgt gtgctttaaa gacccaccgg cactggcagt gagtgttgct   7560
gcttgtgtag gctttggtac gtatgggctt tatttgcttc tggatgttgt gtactacttg   7620
ggtttgttga attattatga gcagttgcgt attgtaattc agctgggcta cctggacatt   7680
gttatgtatt aataaatgct ttgctttctt ctaaagatct ttaagtgctg aattcatatt   7740
tcctcctgca gggtttaaac ttgccgtggc ctattttcag aagaattccc aatagtagtc   7800 caaaatttt gtaacgaagg gagcataata gttacatgca aaggaaaact gccattcttt    7860
agaggggatg cttgtttaag aacaaaaaat atatcacttt cttttgttcc aagtcattgc   7920
gtattttttt aaaatatttt gttccttcgt atatttcgag cttcaatcac tttatggttc   7980
tttgtattct ggctttgctg taaatcgtag ctaaccttct tcctagcaga aattattaat   8040
acttgggata ttttttaga atcaagtaaa ttacatatta ccaccacatc gagctgcttt   8100
taaattcata ttacagccat ataggcttga ttcattttgc aaaatttcca ggatattgac   8160
aacgttaact taataatatc ttgaaatatt aaagctatta tgattagggg tgcaaatgga   8220
ccgagttggt tcggtttata tcaaaatcaa accaaaccaa ctatatcggt ttggattggt   8280
tcggttttgc cgggttttca gcattttctg gttttttttt tgttagatga atattatttt   8340
aatcttactt tgtcaaattt ttgataagta aatatatgtg ttagtaaaaa ttaattttt    8400 ttacaaacat atgatctatt aaaatattct tataggagaa ttttcttaat aacacatgat   8460
atttatttat tttagtcgtt tgactaattt ttcgttgatg tacactttca aagttaacca   8520
```

```
aatttagtaa ttaagtataa aaatcaatat gatacctaaa taatgatatg ttctatttaa    8580
ttttaaatta tcgaaatttc acttcaaatt cgaaaaagat atataagaat tttgatagat    8640
tttgacatat gaatatggaa gaacaaagag attgacgcat tttagtaaca cttgataaga    8700
aagtgatcgt acaaccaatt atttaaagtt aataaaaatg gagcacttca tatttaacga    8760
aatattacat gccagaagag tcgcaaatat ttctagatat ttttaaaga aaattctata     8820 aaagtctta aaggcatata tataaaaact atatatttat attttggttt ggttcgaatt     8880
tgttttactc aataccaaac taaattagac caaatataat tgggttttta atcgcggccc    8940
actagtcacc ggtgtagctt ggcgtaatca tggtcatagc tgtttcctgt gtgaaattgt    9000
tatccgctca caattccaca acatacga gccggaagca taaagtgtaa agcctggggt      9060
gcctaatgag tgagctaact cacattaatt gcgttgcgct cactgcccgc tttccagtcg    9120
ggaaacctgt cgtgccagct gcattaatga atcggccaac gcgcggggag aggcggtttg    9180
cgtattgggc gctcttccgc tcgcacgct gcgcacgctg cgcacgcttc ctcgctcact     9240
gactcgctgc gctcggtcgt tcggctgcgg cgagcggtat cagctcactc aaaggcggta    9300
atacggttat ccacagaatc aggggataac gcaggaaaga acatgtgagc aaaaggccag    9360
caaaaggcca ggaaccgtaa aaaggccgcg ttgctggcgt ttttccatag gctccgcccc    9420
cctgacgagc atcacaaaaa tcgacgctca agtcagaggt ggcgaaaccc gacaggacta    9480
taaagatacc aggcgtttcc ccctggaagc tccctcgtgc gctctcctgt tccgaccctg    9540
ccgcttaccg gatacctgtc cgcctttctc ccttcgggaa gcgtggcgct ttctcatagc    9600
tcacgctgta ggtatctcag ttcggtgtag gtcgttcgct ccaagctggg ctgtgtgcac    9660
gaaccccccg ttcagcccga ccgctgcgcc ttatccggta actatcgtct tgagtccaac    9720
ccggtaagac acgacttatc gccactggca gcagccactg gtaacaggat tagcagagcg    9780
aggtatgtag gcggtgctac agagttcttg aagtggtggc ctaactacgg ctacactaga    9840
aggacagtat ttggtatctg cgctctgctg aagccagtta ccttcggaaa aagagttggt    9900
agctcttgat ccggcaaaca aaccaccgct ggtagcggtg ttttttttgt ttgcaagcag    9960
cagattacgc gcagaaaaaa aggatctcaa gaagatcctt tgatcttttc tacggggtct    10020
gacgctcagt ggaacgaaaa ctcacgttaa gggattttgg tcatgagatt atcaaaaagg    10080
atcttcacct agatcctttt aaattaaaaa tgaagtttta aatcaatcta agtatatat     10140 gagtaaactt ggtctgacag ttaccaatgc ttaatcagtg aggcacctat ctcagcgatc    10200
tgtctatttc gttcatccat agttgcctga ctccccgtcg tgtagataac tacgatacgg    10260
gagggcttac catctggccc cagtgctgca atgataccgc gagacccacg ctcaccggct    10320
ccagatttat cagcaataaa ccagccagcc ggaagggccg agcgcagaag tggtcctgca    10380
actttatccg cctccatcca gtctattaat tgttgccggg aagctagagt aagtagttcg    10440
ccagttaata gtttgcgcaa cgttgttgcc attgctacag gcatcgtggt gtcacgctcg    10500
tcgtttggta tggcttcatt cagctccggt tcccaacgat caaggcgagt tacatgatcc    10560
cccatgttgt gcaaaaaagc ggttagctcc ttcggtcctc cgatcgttgt cagaagtaag    10620
ttggccgcag tgttatcact catggttatg gcagcactgc ataattctct tactgtcatg    10680
ccatccgtaa gatgcttttc tgtgactggt gagtactcaa ccaagtcatt ctgagaatag    10740
tgtatgcggc gaccgagttg ctcttgcccg gcgtcaatac gggataatac cgcgccacat    10800
agcagaactt taaaagtgct catcattgga aaacgttctt cggggcgaaa actctcaagg    10860
```

```
atcttaccgc tgttgagatc cagttcgatg taacccactc gtgcacccaa ctgatcttca    10920
gcatctttta ctttcaccag cgtttctggg tgagcaaaaa caggaaggca aaatgccgca    10980
aaaaagggaa taagggcgac acggaaatgt tgaatactca tactcttcct ttttcaatat    11040
tattgaagca tttatcaggg ttattgtctc atgagcggat acatatttga atgtatttag    11100
aaaaataaac aaatagggdt tccgcgcaca tttccccgaa aagtgccacc tgacgtctaa    11160 gaaccatta ttatcatgac attaacctat aaaaataggc gtatcacgag gccctttcgt     11220
ctcgcgcgtt tcggtgatga cggtgaaaac ctctgacaca tgcagctccc ggagacggtc    11280
acagcttgtc tgtaagcgga tgccgggagc agacaagccc gtcagggcgc gtcagcgggt    11340
gttggcgggt gtcggggctg gcttaactat gcggcatcag agcagattgt actgagagtg    11400
caccatatgc ggtgtgaaat accgcacaga tgcgtaagga gaaaataccg catcaggcgc    11460
cattcgccat tcaggctgcg caactgttgg gaagggcgat cggtgcgggc ctcttcgcta    11520
ttacgccagc tggcgaaagg gggatgtgct gcaaggcgat taagttgggt aacgccaggg    11580
ttttcccagt cacgacgttg taaaacgacg gccagtgaat taccggtg tgatcatggg     11640 ccg                                                                  11643

<210> SEQ ID NO 12
<211> LENGTH: 115
<212> TYPE: DNA
<213> ORGANISM: Artificial Sequence
<220> FEATURE:
<223> OTHER INFORMATION: Synthetic

<400> SEQUENCE: 12
catgattacg ccaagctagc ggccgcattc ccgggaagct aggccaccgt ggcccgcctg        60
caggggaagc ttgcatgcct gcagatcccc ggggatcctc tagagtcgac ctgca           115

<210> SEQ ID NO 13
<211> LENGTH: 19
<212> TYPE: DNA
<213> ORGANISM: Artificial Sequence
<220> FEATURE:
<223> OTHER INFORMATION: Synthetic

<400> SEQUENCE: 13
gggtaccccc ggggtcgac                                                    19

<210> SEQ ID NO 14
<211> LENGTH: 17
<212> TYPE: DNA
<213> ORGANISM: Artificial Sequence
<220> FEATURE:
<223> OTHER INFORMATION: Synthetic

<400> SEQUENCE: 14
taatgagctc gtttaaa                                                      17

<210> SEQ ID NO 15
<211> LENGTH: 55
<212> TYPE: DNA
<213> ORGANISM: Artificial Sequence
<220> FEATURE:
<223> OTHER INFORMATION: Synthetic

<400> SEQUENCE: 15
cggccggcct agctagccac ggtggccaga tccactagtt ctagagcggc cgctt            55
```

```
<210> SEQ ID NO 16
<211> LENGTH: 38
<212> TYPE: DNA
<213> ORGANISM: Artificial Sequence
<220> FEATURE:
<223> OTHER INFORMATION: Synthetic

<400> SEQUENCE: 16
cctgcagatc cccggggatc tctagagtc gacctgca                                38

<210> SEQ ID NO 17
<211> LENGTH: 19
<212> TYPE: DNA
<213> ORGANISM: Artificial Sequence
<220> FEATURE:
<223> OTHER INFORMATION: Synthetic

<400> SEQUENCE: 17 gggtacccccc ggggtcgac                                                   19

<210> SEQ ID NO 18
<211> LENGTH: 138
<212> TYPE: DNA
<213> ORGANISM: Artificial Sequence
<220> FEATURE:
<223> OTHER INFORMATION: Synthetic

<400> SEQUENCE: 18
tggccaccgc ttaattaagg cgcgccatgc ccgggcaagc ggccgcttaa ttaaatttaa        60
atgtttaaac taggaaatcc aagctgggc tgcaggtcaa tcccattgct tttgaagcag        120
ctcaacattg atctcttt                                                     138

<210> SEQ ID NO 19
<211> LENGTH: 14
<212> TYPE: DNA
<213> ORGANISM: Artificial Sequence
<220> FEATURE:
<223> OTHER INFORMATION: Synthetic

<400> SEQUENCE: 19
ggtaccctga gctc                                                         14

<210> SEQ ID NO 20
<211> LENGTH: 41
<212> TYPE: DNA
<213> ORGANISM: Artificial Sequence
<220> FEATURE:
<223> OTHER INFORMATION: Synthetic

<400> SEQUENCE: 20
gaattcatat ttcctcctgc agggtttaaa cttgccgtgg c                           41

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
cggcccacta gtcaccggtg t                                                 21

<210> SEQ ID NO 22
<211> LENGTH: 27
<212> TYPE: DNA
<213> ORGANISM: Artificial Sequence
```

```
<220> FEATURE:
<223> OTHER INFORMATION: Synthetic

<400> SEQUENCE: 22
gcgcacgctg cgcacgctgc gcacgct                                          27

<210> SEQ ID NO 23
<211> LENGTH: 22
<212> TYPE: DNA
<213> ORGANISM: Artificial Sequence
<220> FEATURE:
<223> OTHER INFORMATION: Synthetic

<400> SEQUENCE: 23
acaccggtgt gatcatgggc cg                                               22

<210> SEQ ID NO 24
<211> LENGTH: 69
<212> TYPE: DNA
<213> ORGANISM: Artificial Sequence
<220> FEATURE:
<223> OTHER INFORMATION: Synthetic

<400> SEQUENCE: 24
tggccaccgc ttaattaagg cgcgccatgc ccctgcaga tccccgggga tcctctagag       60
tcgacctgc                                                              69

<210> SEQ ID NO 25
<211> LENGTH: 144
<212> TYPE: DNA
<213> ORGANISM: Artificial Sequence
<220> FEATURE:
<223> OTHER INFORMATION: Synthetic

<400> SEQUENCE: 25
cggccggcct agctagccac ggtggccaga tccactaggg gcaagcggcc gcttaattaa      60
atttaaatgt ttaaactagg aaatccaagc ttgggctgca ggtcaatccc attgcttttg    120
aagcagctca acattgatct cttt                                            144

<210> SEQ ID NO 26
<211> LENGTH: 14
<212> TYPE: DNA
<213> ORGANISM: Artificial Sequence
<220> FEATURE:
<223> OTHER INFORMATION: Synthetic

<400> SEQUENCE: 26
ggtaccctga gctc                                                        14

<210> SEQ ID NO 27
<211> LENGTH: 41
<212> TYPE: DNA
<213> ORGANISM: Artificial Sequence
<220> FEATURE:
<223> OTHER INFORMATION: Synthetic

<400> SEQUENCE: 27
gaattcatat ttcctcctgc agggtttaaa cttgccgtgg c                          41

<210> SEQ ID NO 28
<211> LENGTH: 4
<212> TYPE: PRT
<213> ORGANISM: Homo sapiens
```

-continued

<400> SEQUENCE: 28

Lys Asp Glu Leu
1

<210> SEQ ID NO 29
<211> LENGTH: 8
<212> TYPE: DNA
<213> ORGANISM: Homo sapiens

<400> SEQUENCE: 29 ccatggtg                                                                   8

<210> SEQ ID NO 30
<211> LENGTH: 41
<212> TYPE: DNA
<213> ORGANISM: Homo sapiens

<400> SEQUENCE: 30
gaacaaaaac tcatctcaga agaggatctg aattaggatc c                              41

<210> SEQ ID NO 31
<211> LENGTH: 2
<212> TYPE: PRT
<213> ORGANISM: Homo sapiens

<400> SEQUENCE: 31

Met Val
1

<210> SEQ ID NO 32
<211> LENGTH: 11
<212> TYPE: PRT
<213> ORGANISM: Homo sapiens

<400> SEQUENCE: 32

Glu Gln Lys Leu Ile Ser Glu Glu Asp Leu Asn
1               5                   10

<210> SEQ ID NO 33
<211> LENGTH: 1642
<212> TYPE: DNA
<213> ORGANISM: Homo sapiens

<400> SEQUENCE: 33
ccatggtgat gagacgctac aagctctttc tcatgttctg tatggccggc ctgtgcctca         60
tctccttcct gcacttcttc aagaccctgt cctatgtcac cttcccccga gaactggcct        120
ccctcagccc taacctggtg tccagctttt tctggaacaa tgccccggtc acgcccaggg        180
ccagccccga gccaggaggc cctgacctgc tgcgtacccc actctactcc cactcgcccc        240
tgctgcagcc gctgccgccc agcaaggcgg ccgaggagct ccaccgggtg acttggtgc         300 tgcccgagga caccaccgag tatttcgtgc gcaccaaggc cggcggcgtc tgcttcaaac        360
ccggcaccaa gatgctggag aggccgcccc cgggacggcc ggaggagaag cctgaggggg        420
ccaacggctc ctcggcccgg cggccacccc ggtacctcct gagcgcccgg gagcgcacgg        480
ggggccgagg cgcccggcgc aagtgggtgg agtgcgtgtg cctgcccggc tggcacggac        540
ccagctgcgg cgtgcccact gtggtgcagt actccaacct gcccaccaag gagcggctgg        600
tgcccaggga ggtgccgcgc gcgtcatca acgccatcaa cgtcaaccac gagttcgacc        660
tgctggacgt gcgcttccac gagctgggcg acgtggtgga cgcctttgtg gtgtgcgagt        720
ccaacttcac ggcttatggg gagccgcggc cgctcaagtt ccgggagatg ctgaccaatg        780

```
gcaccttcga gtacatccgc cacaaggtgc tctatgtctt cctggaccac ttcccgcccg    840
gcggccggca ggacggctgg atcgccgacg actacctgcg caccttcctc acccaggacg    900
gcgtctcgcg gctgcgcaac ctgcggcccg acgacgtctt catcattgac gatgcggacg    960
agatcccggc ccgtgacggc gtccttttcc tcaagctcta cgatggctgg accgagccct   1020
tcgccttcca catgcgcaag tcgctctacg gcttcttctg gaagcagccg ggcaccctgg   1080
aggtggtgtc aggctgcacg gtggacatgc tgcaggcagt gtatgggctg acggcatcc    1140
gcctgcgccg ccgccagtac tacaccatgc ccaacttcag acagtatgag aaccgcaccg   1200
gccacatcct ggtgcagtgg tcgctgggca gcccccctgca cttcgccggc tggcactgct   1260
cctggtgctt cacgcccgag ggcatctact tcaagctcgt gtccgcccag aatggcgact   1320
tcccacgctg gggtgactac gaggacaagc gggacctgaa ctacatccgc ggcctgatcc   1380
gcaccggggg ctggttcgac ggcacgcagc aggagtaccc gcctgcagac cccagcgagc   1440
acatgtatgc gcccaagtac ctgctgaaga actacgaccg gttccactac ctgctggaca   1500
accccctacca ggagcccagg agcacggcgg cgggcgggtg gcgccacagg ggtcccgagg   1560
gaaggccgcc cgcccggggc aaactggacg aggcggaagt cgaacaaaaa ctcatctcag   1620
aagaggatct gaattaggat cc                                            1642
```

<210> SEQ ID NO 34
<211> LENGTH: 544
<212> TYPE: PRT
<213> ORGANISM: Homo sapiens

<400> SEQUENCE: 34

```
Met Val Met Arg Arg Tyr Lys Leu Phe Leu Met Phe Cys Met Ala Gly
1               5                   10                  15

Leu Cys Leu Ile Ser Phe Leu His Phe Phe Lys Thr Leu Ser Tyr Val
            20                  25                  30

Thr Phe Pro Arg Glu Leu Ala Ser Leu Ser Pro Asn Leu Val Ser Ser
        35                  40                  45

Phe Phe Trp Asn Asn Ala Pro Val Thr Pro Gln Ala Ser Pro Glu Pro
    50                  55                  60

Gly Gly Pro Asp Leu Leu Arg Thr Pro Leu Tyr Ser His Ser Pro Leu
65                  70                  75                  80

Leu Gln Pro Leu Pro Pro Ser Lys Ala Ala Glu Glu Leu His Arg Val
                85                  90                  95

Asp Leu Val Leu Pro Glu Asp Thr Thr Glu Tyr Phe Val Arg Thr Lys
            100                 105                 110

Ala Gly Gly Val Cys Phe Lys Pro Gly Thr Lys Met Leu Glu Arg Pro
        115                 120                 125

Pro Pro Gly Arg Pro Glu Glu Lys Pro Glu Gly Ala Asn Gly Ser Ser
    130                 135                 140

Ala Arg Arg Pro Pro Arg Tyr Leu Leu Ser Ala Arg Glu Arg Thr Gly
145                 150                 155                 160

Gly Arg Gly Ala Arg Arg Lys Trp Val Glu Cys Val Cys Leu Pro Gly
                165                 170                 175

Trp His Gly Pro Ser Cys Gly Val Pro Thr Val Val Gln Tyr Ser Asn
            180                 185                 190

Leu Pro Thr Lys Glu Arg Leu Val Pro Arg Glu Val Pro Arg Arg Val
        195                 200                 205

Ile Asn Ala Ile Asn Val Asn His Glu Phe Asp Leu Leu Asp Val Arg
    210                 215                 220
```

-continued

```
Phe His Glu Leu Gly Asp Val Val Asp Ala Phe Val Val Cys Glu Ser
225                 230                 235                 240

Asn Phe Thr Ala Tyr Gly Glu Pro Arg Pro Leu Lys Phe Arg Glu Met
                245                 250                 255

Leu Thr Asn Gly Thr Phe Glu Tyr Ile Arg His Lys Val Leu Tyr Val
            260                 265                 270

Phe Leu Asp His Phe Pro Pro Gly Gly Arg Gln Asp Gly Trp Ile Ala
            275                 280                 285

Asp Asp Tyr Leu Arg Thr Phe Leu Thr Gln Asp Gly Val Ser Arg Leu
        290                 295                 300

Arg Asn Leu Arg Pro Asp Asp Val Phe Ile Ile Asp Asp Ala Asp Glu
305                 310                 315                 320

Ile Pro Ala Arg Asp Gly Val Leu Phe Leu Lys Leu Tyr Asp Gly Trp
                325                 330                 335

Thr Glu Pro Phe Ala Phe His Met Arg Lys Ser Leu Tyr Gly Phe Phe
                340                 345                 350

Trp Lys Gln Pro Gly Thr Leu Glu Val Val Ser Gly Cys Thr Val Asp
            355                 360                 365

Met Leu Gln Ala Val Tyr Gly Leu Asp Gly Ile Arg Leu Arg Arg Arg
        370                 375                 380

Gln Tyr Tyr Thr Met Pro Asn Phe Arg Gln Tyr Glu Asn Arg Thr Gly
385                 390                 395                 400

His Ile Leu Val Gln Trp Ser Leu Gly Ser Pro Leu His Phe Ala Gly
                405                 410                 415

Trp His Cys Ser Trp Cys Phe Thr Pro Glu Gly Ile Tyr Phe Lys Leu
                420                 425                 430

Val Ser Ala Gln Asn Gly Asp Phe Pro Arg Trp Gly Asp Tyr Glu Asp
            435                 440                 445

Lys Arg Asp Leu Asn Tyr Ile Arg Gly Leu Ile Arg Thr Gly Gly Trp
        450                 455                 460

Phe Asp Gly Thr Gln Gln Glu Tyr Pro Pro Ala Asp Pro Ser Glu His
465                 470                 475                 480

Met Tyr Ala Pro Lys Tyr Leu Leu Lys Asn Tyr Asp Arg Phe His Tyr
                485                 490                 495

Leu Leu Asp Asn Pro Tyr Gln Glu Pro Arg Ser Thr Ala Ala Gly Gly
            500                 505                 510

Trp Arg His Arg Gly Pro Glu Gly Arg Pro Pro Ala Arg Gly Lys Leu
        515                 520                 525

Asp Glu Ala Glu Val Glu Gln Lys Leu Ile Ser Glu Glu Asp Leu Asn
        530                 535                 540
```

GNTIII EXPRESSION IN PLANTS

RELATED APPLICATIONS

This application is a divisional of U.S. application Ser. No. 10/508,166, filed on Sep. 17, 2004, now U.S. Pat. No. 7,897,842, which is a national stage filing under 35 U.S.C. 371 of International Application PCT/IB03/001562, filed Mar. 18, 2003, which claims priority from Application Nos. 60/365,769, filed Mar. 19, 2002 and Application No. 60/368,047, filed Mar. 26, 2002 the entire contents of each of which are incorporated by reference herein.

FIELD OF THE INVENTION

The invention relates to expression of a mammalian N-acetylglucosaminyl-transferase III (GnTIII) enzyme in plants and its use in producing glycoproteins with bisected oligosaccharides and increased amount of terminal GlcNAc residues. The invention further relates to a hybrid protein comprising the catalytic site of GnTIII and transmembrane domain of Golgi apparatus and/or endoplasmic reticulum (ER) protein or modified GNTIII comprising ER retention signals and its use in producing glycoproteins with oligosaccharides that lack immunogenic xylose and fucose residues.

BACKGROUND OF THE INVENTION

N-Acetylglucosaminyltransferases (GlcNAc-transferases) are "branching" enzymes that add an Nacetylglucosamine (GlcNAc) residue to one of the mannoses of the trimannosyl core structure of typical Nlinked glycans. At least six GlcNAc-transferases are known with little or no sequence homology. Besides different protein structures, these GlcNActransferases also have different enzymatic properties and substrate specificity. All are typical type II transmembrane proteins with a cytoplasmic domain, a transmembrane anchor and an extracellular stem region with catalytic domain.

A remarkable GlcNAc-transferase is GlcNAc-transferase III (GnTIII). GnTIII, also known as UDP-Nacetylglucosamine:β-D-mannoside β(1,4)-N-acetylglucosaminyltransferase III (EC 2.4.1.144), inserts bisecting GlcNAc residues in complex-type N-linked glycans of cellular glycoproteins (for a review see Taniguchi, et al., "A glycomic approach to the identification and characterization of glycoprotein function in cells transfected with glycosyltransferase genes" Proteomics 1:239247, 2001). GnTIII adds the GlcNAc through a β(1,4) linkage to the β-linked mannose of the trimannosyl core structure of the N-linked glycan. GnTIII was first identified in hen oviduct (Narasimhan S., "Control of glycoprotein synthesis. UDP-GlcNAc:glycopeptide β 4-Nacetylglucosaminyltransferase III, an enzyme in hen oviduct which adds GlcNAc in β14 linkage to the β-linked mannose of the trimannosyl core of N-glycosyl oligosaccharides" The Journal of Biological Chemistry 257:10235-10242, 1982) but a high level of activity has also been reported in various types of rat hepatomas, human serum, liver and hepatoma tissues of patients with hepatomas and liver cirrhosis (Ishibashi, et al., "N-acetylglucosaminyltransferase III in human serum and liver and hepatoma tissues: increased activity in liver cirrhos and hepatoma patients" Clinical Chimica Acta 185:325, 1989; Narishimhan, et al., "Expression of N-acetylglucosaminyltransferase III in hepatic nodules during rat liver carcinogenesis promoted by orotic acid" Journal of Biological Chemistry 263:1273-1281, 1988; Nishikawa, et al. "Determination of N-acetylglucosaminyltransferases III, IV and V in normal and hepatoma tissues of rats" Biochimica et Biophysica Acta 1035:313-318, 1990; Pascale, et al., "Expression of N-acetylglucosaminyltransferase III in hepatic nodules generated by different models of rat liver carcinogenesis" Carcinogenesis 10:961964, 1989). Bisected oligosaccharides on glycoproteins have been implicated in antibody-dependent cellular cytotoxicity (ADCC). ADCC is a lytic attack on antibody-targeted cells and is triggered upon binding of lymphocyte receptors to the constant region (Fc) of antibodies. Controlled expression of GnTIII in recombinant Chinese Hamster Ovary (CHO) production cell lines that lack GnTIII activity resulted in antibodies with bisected oligosaccharides with optimized ADCC activity (Davies, et al., "Expression of GnTIII in a recombinant anti-CD20 CHO production cell line: expression of antibodies with altered glycoforms leads to an increase in ADCC through higher affinity for FcγRIII" Biotechnology and Bioengineering 74:288-294, 2001; Umana, et al., "Engineered glycoforms of an antineuroblastoma IgG1 with optimized antibody-dependent cellular cytotoxic activity" Nature Biotechnology 17:176-180, 1999). The ADCC activity correlated well with the level of Fc region-associated bisected complex oligosaccharides present on the recombinant antibody (Umana, et al., "Engineered glycoforms of an antineuroblastoma IgG1 with optimized antibody-dependent cellular cytotoxic activity" Nature Biotechnology 17:176-180, 1999). Bisecting GlcNAc residues resulting from GnTIII activity affect the conformation of the sugar chains in such a way that other glycosyltransferases such as GlcNAc-transferase II and α1,6-fucosyltransferase, but not β(1,4)-galactosyltransferase, can no longer act (Tanigichi, et al., 2001). Overexpression of GnTIII in CHO cells is lethal.

In contrast to typical mammalian production cell lines such as CHO cells, transgenic plants are generally recognized as a safe production system for therapeutic proteins. Plant glycoproteins, however, differ in oligosaccharide structure with those from mammals in several aspects. They lack terminal galactose and sialic acid, have an additional core xylose and differently linked core fucose (α-1,3) instead of (α-1,6). Like CHO and other pharmaceutical production cell lines they also completely lack bisected oligosaccharides. Plants have the capacity to generate the common core structure, GN2M3GN2 but predominantly M3 GN2 variants are found, indicating removal of terminal GN by hexosaminidases.

Biogenesis of N-linked glycans begins with the synthesis of a lipid linked oligosaccharide moiety (Glc3Man9GlcNAc2-) which is transferred en bloc to the nascent polypeptide chain in the endoplasmic reticulum (ER). Through a series of trimming reactions by exoglycosidases in the ER and cis-Golgi compartments the so-called "high mannose" (Man9GlcNAc2 to Man5GlcNAc2) glycans are formed. Subsequently, the formation of complex type glycans starts with the transfer of the first GlcNAc onto Man5GlCNAC2 by GnTI and further trimming by mannosidase II (Mann) to form GlcNAcMan3 GlcNAc2. Complex glycan biosynthesis continues while the glycoprotein is progressing through the secretory pathway with the transfer in the Golgi apparatus of the second GlcNAc residue by GnTII as well as other monosaccharide residues onto the GlcNAcMan3GlcNAc2 under the action of several other glycosyl transferases. Plants and mammals differ with respect to the formation of complex glycans. In plants, complex glycans are characterized by the presence of β(1,2)-xylose residues linked to the Man-3 and/or an α(1,3)-fucose residue linked to GlcNAc1, instead of an α(1,6)-fucose residue linked to the GlcNAc-1 (Lerouge, P., et al., "N-glycoprotein biosynthesis in plants: recent developments and future trends" Plant Mol Biol 38:31-48, 1998). Genes encoding the corresponding xylosyl (XylT) and fucosyl (FucT) transferases have been isolated (Strasser R, "Molecular cloning and functional expression of β 1,2-xylosyltransferase cDNA from *Arabidopsis thaliana*" *FEBS Lett.* 472:105-8, 2000; Leiter, H., et al, "Purification, cDNA cloning, and expression of GDP-L-Fuc:Asn-linked GlcNAc α 1,3-fucosyltransferase from mung beans" *J Biol Chem.* 274:21830, 1999). Xylose and fucose epitopes are known to be highly immunogenic and possibly allergenic which may pose a problem when plant are used for the production of therapeutic glycoproteins. Moreover, blood serum of many allergy patients contains IgE directed against these epitopes which make particularly these patients at risk to treatments with xylose and fucose containing recombinant proteins. In addition, this carbohydrate directed IgE in sera might cause false positive reaction in in vitro tests using plant extracts since there is evidence that these carbohydrate specific IgE's are not relevant for the allergenic reaction. Plants do not possess β(1,4)galactosyltransferases nor α(2,6)sialyltransferases and consequently plant glycans lack the β(1,4) galactose and terminal α(2,6)NeuAc residues often found on mammalian glycans (Vitale and Chrispeels, "Transient N-acetylglucosamine in the biosynthesis of phytohemagglutinin: attachment in the Golgi apparatus and removal in protein bodies" *J Cell Biol* 99:133-140, 1984; Lerouge, P., et al., "N-glycoprotein biosynthesis in plants: recent developments and future trends" *Plant Mol Biol* 38:31-48, 1998).

The final glycan structures are not only determined by the mere presence of enzymes involved in their biosynthesis but to a large extend by the specific sequence of the various enzymatic reactions. The latter is controlled by discrete sequestering and relative position of these enzymes throughout the ER and Golgi, which is mediated by the interaction of determinants of the transferase and specific characteristics of the sub-Golgi compartment for which the transferase is destined. A number of studies using hybrid, molecules have identified that the transmembrane domains of several glycosyltransferases play a central role in their sub-Golgi sorting (Grabenhorst E., et. al., *J. Biol. Chem.* 274:36107-36116, 1999; Colley, K., *Glycobiology.* 7:1-13, 1997, Munro, S., *Trends Cell Biol.* 8:11-15, 1998; Gleeson P. A., *Histochem. Cell Biol.* 109:517-532, 1998).

Similar to mammalian production cell lines used in pharmaceutical industry, glycoproteins produced in plants lack GnTIII activity. Plants not only lack GnTIII activity but are completely devoid of GnTIII-like sequences. In addition, plants also lack GnTIV, GnTV ands GnTVI sequences and moreover, sialic acid residues. (For an overview of the major glycosylation attributes of commonly used cell expression systems including plants see, Jenkins, et al., "Getting the glycosylation right: implications for the biotechnology industry" *Nature Biotechnology* 14:975-979, 1996). Nevertheless, plants are a very potent production system. Plants are generally accepted as safe and are free of particles infectious to humans. Plant production is easy scalable and N-linked glycosylation can be controlled (Bakker, et al., "Galactose-extended glycans of antibodies produced by transgenic plants" *Proc. Nat. Acad. Sci. USA* 98:2899-2904, 2001).

Transgenic tobacco plants that produce galactosylated recombinant monoclonal antibodies (Mabs) upon introduction of the human gene for β(1,4)-galactosyltransferase have been reported (hGal T; Bakker, et al., "Galactose-extended glycans of antibodies produced by transgenic plants" *Proc. Nat. Acad. Sci. USA* 98:2899-2904, 2001; WO01/31044 and WO01/31045).

Therapeutic glycoproteins can be improved by altering their glycosylation pattern (Davies, et al., "Expression of GnTIII in a recombinant anti-CD20 CHO production cell line: expression of antibodies with altered glycoforms leads to an increase in ADCC through higher affinity for FcγRIII" *Biotechnology and Bioengineering* 74:288-294, 2001; Umana, et al., "Engineered glycoforms of an antineuroblastoma IgG1 with optimized antibody-dependent cellular cytotoxic activity" *Nature Biotechnology* 17:176-180, 1999; Fukuta, et al., "Remodeling of sugar chain structures of human interferon-γ" *Glycobiology* 10:421-430, 2000; Misaizu, et al., "Role of antennary structure of N-linked sugar chains in renal handling of recombinant human erythropoietin" *Blood* 86:4097-4104, 1995; Sburlati, et al., "Synthesis of bisected glycoforms of recombinant IFN-β by overexpression of β-1,4-N-acetylglucosaminyl-tranferase III in Chinese Hamster Ovary cells" *Biotechnology Prog.* 14:189-192, 1998). Higher oligosaccharide antennarity of EPO, for example, leads to increased in vivo activity due to reduced kidney filtration (Misaizu, et al., "Role of antennary structure of N-linked sugar chains in renal handling of recombinant human erythropoietin" *Blood* 86:4097-4104, 1995). Biosynthesis of such superior glycoforms can be achieved with the "standard" glycosylation machinery of normal production cell lines by two methodologies. The first is by enriching specific glycoforms during purification and the second is by introducing mutations in the polypeptide chain. The latter makes it possible to shift the glycosylation site within the glycoprotein resulting in different glycosylation patterns as the result of differences in accessibility. A complementary route is through genetic engineering of the production cell line itself. New glycosylation patterns can be obtained through expression of glycosyltransferase and glycosidase genes in production cell lines. These genes code for enzymes that either add or remove specific saccharides to and from the glycan of cellular glycoproteins. Several glycosyltransferase genes have been introduced in CHO cells to manipulate glycoform biosynthesis. One of them is GnTIII. Glycosyltransferase GnTIII is involved in branching of the N-linked glycan and results in bisecting GlcNAc residues. CHO cells and other production cell lines typically lack GnTIII activity (Stanley, P. and C. A. Campbell, "A dominant mutation to ricin resistance in chinese hamster ovary cells induces UDP-GlcNAc: glycopeptide β-4-N-acetylglucosaminyl-transferase III activity" *Journal of Biological Chemistry* 261:13370-13378, 1984). Expression of GnTIII in CHO resulted in bisected complex oligosaccharides as expected but overexpression resulted in growth inhibition and was toxic to cells. Similarly, overexpression of GnTV, another glycosyltransferase that introduces triantennary sugar chains, also resulted in growth inhibition suggesting that this may be a general feature of glycosyltransferase overexpression (Umana, et al., "Engineered glycoforms of an antineuroblastoma IgG1 with optimized antibody-dependent cellular cytotoxic activity" *Nature Biotechnology* 17:176-180, 1999).

Therefore, there is a need to provide a means for producing glycoprotein in plants with human compatible non-immunogenic bisecting oligosaccharides.

SUMMARY OF THE INVENTION

The invention relates to expression of a mammalian N-acetylglucosaminyl-transferase III (GnTIII) enzyme in plants and its use in producing glycoproteins with bisected oligosaccharides and increased amount of terminal GlcNAc residues. The invention further relates to a hybrid protein comprising the catalytic site of GnTIII and transmembrane domain of Golgi apparatus and/or endoplasmic reticulum (ER) protein or modified GNTIII comprising ER retention signals and its use in producing glycoproteins with oligosaccharides that lack immunogenic xylose and fucose residues.

In one embodiment, the present invention contemplates a plant host system comprising or expressing a mammalian UDP-Nacetylglucosamine:(β-D-mannoside β(1,4)-Nacetylglucosaminyltransferase (GnTIII) enzyme (nucleotide sequence: SEQ ID NO.: 1, Genbank I.D. number AL022312 (Dunham, I., et al., *Nature* 402:489-495, 1999); protein sequence: SEQ ID NO.: 2, Genbank I.D. number Q09327), wherein said GnTIII inserts bisecting Nacetyl glucosamine (GlcNAc) residues in complex-type N-linked glycans of a glycoprotein present in said plant host system In a specific embodiment of the invention, the plant host system further comprises a heterologous glycoprotein or functional fragment thereof comprising bisected oligosaccharide, particularly galactose residues. The GnTIII inserts bisecting N-GlcNAc residues onto said heterologous glycoprotein.

In one embodiment, the present invention contemplates to a method for obtaining a plant host system expressing a heterologous glycoprotein comprising bisecting oligosaccharides. In one embodiment, the method comprises crossing a plant expressing a heterologous glycoprotein with a plant expressing said GnTIII, harvesting progeny from said crossing and selecting a desired progeny plant expressing said heterologous glycoprotein and expressing mammalian GnTIII. Alternatively, said plant host system may be obtained by introducing into a plant or portion thereof a nucleic acid encoding said mammalian GnTIII and a nucleic acid encoding said heterologous glycoprotein and isolating a plant or portion thereof expressing said heterologous glycoprotein and expressing mammalian GnTIII that is normally not present in plants. Furthermore, the invention is directed to a method for obtaining said heterologous glycoprotein from said plant comprising obtaining a plant host system using either of the procedures described above and further isolating said heterologous glycoprotein.

In another embodiment, it is contemplated that the plant host system of the present invention further comprises a functional mammalian enzyme providing N-glycan biosynthesis that is normally not present in plants thereby, for example, providing the capacity to extend an N-linked glycan by the addition of a galactose as described in WO 01/21045 (herein incorporated by reference). In another embodiment, the present invention further contemplates a plant host system, wherein said plant host system comprises crossing a plant, said plant comprising a functional protein such as a transporter protein or a enzyme (e.g., a mammalian protein) or functional fragment thereof wherein said protein provides N-glycan biosynthesis, with a plant comprising said mammalian GnTIII. In another embodiment, the present invention contemplates harvesting the progeny from said crossing and selecting a desired progeny plant expressing said functional protein such as, for example, a transporter protein or enzyme or functional fragment thereof. In yet another embodiment of the present invention, it is contemplated that the expressed protein provides N-glycan biosynthesis and the mammalian GnTIII. In still yet another embodiment, the present invention contemplates a plant host system, wherein a nucleic acid encoding the GnTIII and a nucleic acid encoding a functional protein (for example, a transporter or an enzyme [e.g., mammalian] or functional fragment thereof) providing N-glycan biosynthesis and isolating said plant or portion thereof expressing the functional protein or functional fragment thereof providing N-glycan biosynthesis and said mammalian GnTIII. Although the present invention is not limited to any particular theory or mechanism, it is believed that such a combination increases galactosylation of a heterologous glycoprotein. Additionally, in one embodiment, it is contemplated that GnTIII and other proteins providing N-glycosylation such as GaIT can also be introduced simultaneously via one transformation vector.

In one embodiment, the present invention contemplates a plant host system comprising expressing said heterologous glycoprotein (wherein, said heterologous glycoprotein has increased galactosylation) and methods for obtaining said plant host cell system and said heterologous glycoprotein. In another embodiment, the plant host cell system may be obtained by either crossing a plant wherein the plant comprises mammalian GnTIII and a functional protein (for example, a transporter or an enzyme [e.g., mammalian] or functional fragment thereof that provides N-glycan biosynthesis not normally found in plants) with a plant comprising a heterologous glycoprotein and, then, selecting said progeny plants. In yet another embodiment, it is contemplated that said heterologous glycoprotein may be obtained by introducing nucleic acid sequences encoding 1) said GnTIII, 2) said functional protein or enzyme providing N-glycan biosynthesis not normally found in plants and 3) said heterologous glycoprotein into said plant or portion thereof and isolating said plant or portion thereof expressing said nucleic acid sequences. In another embodiment of the present invention, it is contemplated that the heterologous glycoproteins will be isolated or purified from the plant host systems.

In one embodiment of the present invention, a hybrid protein is contemplated, wherein the hybrid protein comprises 1) an isolated hybrid protein comprising a catalytic portion of mammalian GnTIII and 2) a transmembrane portion of a protein from, for example, the endoplamsic reticulum or Golgi apparatus of a eukaryotic cell. In another embodiment, the present invention also contemplates a modified mammalian GnTIII comprising a retention signal such as KDEL for retention of said GnTIII in the ER. In yet another embodiment, the present invention contemplates nucleic acid sequences encoding 1) said hybrid proteins and said modified mammalian GnTIII, 2) vectors comprising said nucleic acid sequences and 3) plant host systems comprising said sequences. In one embodiment, these hybrid proteins and modified GnTIIIs may act to relocalize GnTIII activity in the endoplasmic reticulum (ER) and/or Golgi apparatus. In another embodiment, the present invention contemplates methods for obtaining these hybrid proteins and modified GnTIII proteins by, for example, introducing sequences encoding said hybrid proteins or modified GnTIIIs into a plant or portion thereof. Although the present invention is not limited to any particular theory or mechanism, it is believed that as a result of such relocalization, bisecting GlcNAc is be introduced earlier in the N-glycan biosynthesis sequence of reactions thereby preventing subsequent enzymatic reactions and, as a consequence, a heterologous protein expressed in a plant host system (for example, the plant host system of the present invention) will lack xylose and fucose and have increased amount of terminal GlcNAc. Accordingly, one embodiment of the present invention contemplates a method to provide a plant host system expressing a heterologous glycoprotein (said plant host system having the capacity to extend an N-linked glycan with galactose) comprising crossing a plant comprising said 1) hybrid protein or said modified GnTIII with a plant comprising said heterologous protein and 2) selecting said desired progeny. In another embodiment, the present invention contemplates introducing into a plant or portion thereof a nucleic acid sequence encoding 1) said modified GnTIII or said hybrid protein and said heterologous glycoprotein and 2) isolating said plant or portion thereof expressing a heterologous glycoprotein with the capacity to extend and N-linked glycan with galactose. In yet another embodiment, the present invention contemplates a method for obtaining said desired heterologous glycoprotein, said method comprising isolating said glycoprotein from said plant or portion thereof.

In one embodiment, the present invention contemplates that the plant-derived glycoprotein or functional fragment thereof may be used for the production of a pharmaceutical composition (for example, an antibody, a hormone, a vaccine antigen, an enzyme, or the like). In another embodiment, the present invention contemplates a pharmaceutical composition comprising a glycoprotein or functional fragment thereof is now also provided.

In one embodiment, the present invention contemplates variants or mutants of GntIII. The terms "variant" and "mutant" when used in reference to a polypeptide refer to an amino acid sequence that differs by one or more amino acids from another, usually related, polypeptide. In another embodiment, the present invention contemplates variants that have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine (V)-leucine (L)-isoleucine (I), phenylalanine (F)-tyrosine (Y), lysine (K)-arginine (R), alanine (A)-valine (V), and asparagine (N)-glutamine (Q).

In yet another embodiment, the present invention contemplates variants that have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. For both conservative and non-conservative variants, preferred variants have less than 10%, preferably less than 5% and, still more preferably, less than 2% changes (whether substitutions, deletions, and so on).

In one embodiment, the present invention contemplates a plant host (cell) system, comprising a mammalian UDP-N-acetylglucosamine: β-D mannoside β(1,4)-N-acetylglucosaminyltransferase (GnTIII) enzyme (or portion or variant thereof, wherein said GnTIII inserts bisecting N-acetyl glucosamine (GlcNAc) residues in complex-type N-linked glycans of a glycoprotein present in said plant host system). In another embodiment, the present invention contemplates the plant host, wherein said GnTIII is a human GnTIII. In yet another embodiment, the present invention contemplates the plant host system, wherein said system is a portion of a plant. In yet another embodiment, the present invention contemplates the plant host system, wherein said system is a portion of a plant selected from the group consisting of a cell, leaf, embryo, callus, stem, pericarp, protoplast, root, tuber, kernel, endosperm and embryo. In yet another embodiment, the present invention contemplates the plant host system, wherein said system is a whole plant. In yet another embodiment, the present invention contemplates the plant host system, further comprising a heterologous glycoprotein (or functional fragment thereof). In yet another embodiment, the present invention contemplates the plant host system, wherein said heterologous glycoprotein protein comprises an antibody, or fragment (e.g. Fc, Fv, Fab, Fab$_2$) thereof. In yet another embodiment, the present invention contemplates the plant host system, wherein said heterologous glycoprotein or functional fragment thereof comprises bisected oligosaccharides. In yet another embodiment, the present invention contemplates the plant host system, wherein said heterologous glycoprotein (or functional fragment thereof) comprises bisected glycans with galactose residues. In yet another embodiment, the present invention contemplates the plant host system, wherein said plant is a tobacco plant. In yet another embodiment, the present invention contemplates the plant host system, which further comprises a functional protein selected from a group consisting of a transporter or a (mammalian) enzyme (or functional fragment thereof) providing N-glycan biosynthesis. In yet another embodiment, the present invention contemplates the plant host system, wherein said enzyme is a (human) β-1,4 galactosyltransferase. In yet another embodiment, the present invention contemplates the plant host system, which further comprises a heterologous glycoprotein, having an increased number of galactose residues. In yet another embodiment, the present invention contemplates a plant host system comprising a nucleic acid sequence encoding a mammalian GnTIII protein. In yet another embodiment, the present invention contemplates a plant host system comprising a vector comprising a nucleic acid sequence encoding a mammalian GnTIII protein. In yet another embodiment, the present invention contemplates the plant host, which further comprises a nucleic acid sequence encoding a functional protein selected from a group consisting of a transporter or a (mammalian) enzyme (or functional fragment thereof) providing N-glycan biosynthesis.

In one embodiment, the present invention contemplates a method (for obtaining a plant host system expressing a heterologous glycoprotein having bisected oligosaccharides) comprising a) crossing a plant expressing a heterologous glycoprotein with a, b) harvesting progeny from said crossing and c) selecting a desired progeny plant (expressing said heterologous glycoprotein and expressing a mammalian GnTIII that is normally not present in plants). In another embodiment, the present invention contemplates this method, wherein said desired progeny plant expresses said heterologous glycoprotein protein having bisected oligosaccharides. In yet another embodiment, the present invention contemplates this method, wherein said plant host system is a transgenic plant.

In one embodiment, the present invention contemplates a method for obtaining a heterologous glycoprotein having bisected oligosaccharides comprising a) introducing a nucleic acid sequence encoding GnTIII that is normally not present in plant into a plant host system and a nucleic acid sequence encoding a heterologous glycoprotein and b) isolating said heterologous glycoprotein. In another embodiment, the present invention contemplates this method, wherein said nucleic acid sequences are introduced into a plant cell and said plant cell is regenerated into a plant. In yet another embodiment, the present invention contemplates the same method, wherein said nucleic acid sequences are introduced into a plant host system by transforming said plant host system with a vector comprising a acid sequence encoding GnTIII that is normally not present in plant into a plant and a nucleic acid sequence encoding a heterologous glycopraxein. In yet another embodiment, the present invention contemplates the method, wherein said nucleic acid sequences are introduced into a plant host system by transforming said plant host system with a vector comprising a nucleic acid sequence encoding GnTIII that is normally not present in plant into a plant and a nucleic acid sequence encoding a heterologous glycoprotein. In yet another embodiment, the present invention contemplates the method, wherein said nucleic acid sequences are introduced into a plant host system by transforming said plant with a vector comprising a nucleic acid sequence encoding GnTIII that is normally not present in plant into a plant host system and vector comprising a nucleic acid sequence encoding a heterologous glycoprotein. In yet another embodiment, the present invention contemplates a method for obtaining a heterologous glycoprotein having bisected oligosaccharides comprising cultivating the regenerated plant.

In one embodiment, the present invention contemplates a method for obtaining a desired glycoprotein (or functional fragment thereof) comprising a) cultivating the plant host system (until said plant has reached a harvestable stage) and b) harvesting said plant (and fractionating to obtain fractionated plant material and c) at least partly isolating said glycoprotein from said fractionated plant material). In another embodiment, the present invention contemplates a plant obtainable by the contemplated method.

In one embodiment, the present invention contemplates A method for obtaining a plant host system comprising a functional protein selected from a group consisting of a transporter or a (mammalian) enzyme or functional fragment thereof providing N-glycan biosynthesis and a mammalian GnTIII comprising crossing a plant comprising a functional protein such as a transporter or a (mammalian) enzyme or functional fragment thereof providing N-glycan biosynthesis with a plant according to Claim 5, harvesting progeny from said crossing and selecting a desired progeny plant expressing said functional protein such as a transporter or a (mammalian) enzyme or functional fragment thereof providing N-glycan biosynthesis and said mammalian GnTIII. In another embodiment, the present invention contemplates a transgenic plant obtained according to the contemplated.

In one embodiment, the present invention contemplates a method for increasing galactosylation of a heterologous glycoprotein expressed in a plant host system comprising introducing a nucleic acid sequence encoding GnTIII and a sequence selected from a group consisting sequences that encode a transporter or a (mammalian) enzyme or functional fragment not normally present in a plant into said plant host system expressing said heterologous glycoprotein and isolating said glycoprotein.

In one embodiment, the present invention contemplates a plant derived glycoprotein comprising bisected oligosaccharides.

In one embodiment, the present invention contemplates the use of a plant host system contemplated by the present invention to produce a desired glycoprotein or functional fragment thereof. In another embodiment, the present invention contemplates that said glycoprotein or functional fragment thereof comprises bisected oligosaccharides. In yet another embodiment, the present invention contemplates a plant-derived glycoprotein or functional fragment thereof obtained by a method contemplated by the present invention. In yet another embodiment, the present invention contemplates a glycoprotein or functional fragment thereof contemplated by the invention for the production of a pharmaceutical composition. In yet another embodiment, the present invention contemplates a composition comprising a glycoprotein or functional fragment thereof as contemplated by the present invention.

In one embodiment, the present invention contemplates an isolated hybrid protein comprising an active site of GnTIII and a transmembrane region of a protein, said protein residing in endoplasmic reticulum or Golgi apparatus of a eukaryotic cell. In another embodiment, the present invention contemplates the protein of the present invention, wherein said protein residing in endoplasmic reticulum or Golgi apparatus of a eukaryotic cell is an enzyme. In yet another embodiment, the present invention contemplates the protein accordof the present invention, wherein said protein residing in endoplasmic reticulum or Golgi apparatus of a eukaryotic cell is a glycosyltransferase. In yet another embodiment, the present invention contemplates the protein of the present invention, wherein said protein residing in endoplasmic reticulum or Golgi apparatus of a eukaryotic cell is a glycosyltransferase selected from the group consisting of a mannosidaseI, mannosidaseII, GnTI, GnTII, XylT and FucT. In yet another embodiment, the present invention contemplates the protein accorof the present invention, wherein said protein residing in endoplasmic reticulum or Golgi apparatus of a eukaryotic cell is a plant protein. In yet another embodiment, the present invention contemplates an isolated nucleic acid sequence encoding the protein of the present invention. In yet another embodiment, the present invention contemplates a vector comprising the isolated nucleic acid sequence of the present invention. In yet another embodiment, the present invention contemplates a plant comprising the isolated nucleic acid sequence of the present invention. In yet another embodiment, the present invention contemplates the plant(s) of the present invention which further comprises a nucleic acid sequence encoding a heterologous glycoprotein.

In one embodiment, the present invention contemplates a method (for providing a transgenic plant capable of expressing a heterologous glycoprotein with the capacity to extend an N-linked glycan with galactose) comprising a) crossing a transgenic plant with a plant of the present invention, b) harvesting progeny from said crossing and c) selecting a desired progeny plant (expressing said recombinant protein and expressing a functional (mammalian) enzyme involved in (mammalian) N-glycan biosynthesis that is normally not present in plants).

In one embodiment, the present invention contemplates a method for providing a transgenic plant capable of expressing a heterologous glycoprotein with the capacity to extend an N-linked glycan with galactose comprising introducing the nucleic acid sequence of the present invention and a nucleic acid sequence encoding said heterologous glycoprotein.

In one embodiment, the present invention contemplates a method, comprising: a) providing: i) a plant cell, and ii) an expression vector comprising nucleic acid encoding a GNTIII enzyme; and b) introducing said expression vector into said plant cell under conditions such that said enzyme is expressed. In another embodiment, the present invention contemplates the method, wherein said nucleic acid encoding a GNTIII comprises the nucleic acid sequence of SEQ ID NO:1.

In one embodiment, the present invention contemplates a method, comprising: a) providing: i) a plant cell, ii) a first expression vector comprising nucleic acid encoding a GNTIII enzyme, and iii) a second expression vector comprising nucleic acid encoding a heterologous glycoprotein; and b) introducing said first and second expression vectors into said plant cell under conditions such that said hybrid enzyme and said heterologous protein are expressed. In another embodiment, the present invention contemplates the method, wherein said heterologous protein is an antibody or antibody fragment.

In one embodiment, the present invention contemplates A method, comprising: a) providing: i) a first plant comprising a first expression vector, said first vector comprising nucleic acid encoding a GNTIII enzyme, and ii) a second plant comprising a second expression vector, said second vector comprising nucleic acid encoding a heterologous protein; and b) crossing said first plant and said second plant to produce progeny expressing said hybrid enzyme and said heterologous protein.

In one embodiment, the present invention contemplates a plant, comprising first and second expression vectors, said first vector comprising nucleic acid encoding a GNTIII enzyme, said second vector comprising nucleic acid encoding a heterologous protein. In another embodiment, the present invention contemplates the, wherein said heterologous protein is an antibody or antibody fragment.

BRIEF DESCRIPTION OF THE FIGURES

FIGS. 3A and 3B show (A) the T-DNA construct carrying the genes encoding glycan modifying enzymes to produce efficiently galactosylated bisected glycans that are devoid of immunogenic xylose and fucose and (B) the T-DNA construct carrying antibody light chain and heavy chain genes. TmXyl=transmembrane domain of xylosyltransferase, TmGnTI=transmembrane domain of GnT, P=promoter, R=selection marker, L=antibody light chain and H=antibody heavy chain.

FIGS. 4A and 4B show, respectively, a nucleotide sequence (SEQ ID NO: 33) and a protein sequence (SEQ ID NO: 34). The underlined portion of FIG. 4A and the underlined portion of FIG. 4B represent the nucleotide sequence (SEQ ID NO: 1) and protein sequence (SEQ ID NO: 2) of GnTIII, respectively, including a c-myc tag. Residues that can undergo conservative amino acid substitutions are defined in the DEFINITIONS section.

FIGS. 5A and 5B show a (A) map of the plasmid pDAB4005 and (B) the nucleotide sequence of the plasmid pDAB4005 (SEQ ID NO: 8).

FIGS. 6A and 6B show a (A) map of the plasmid pDAB7119 and (B) the nucleotide sequence of the plasmid pDAB7119 (SEQ ID NO: 9) including splice sites.

FIGS. 7A and 7B show a (A) map of the plasmid pDAB8504 and (B) the nucleotide sequence of the plasmid pDAB8504 (SEQ ID NO: 10).

FIGS. 8A and 8B show a (A) map of the plasmid pDAB7113 and (B) the nucleotide sequence of the plasmid pDAB7113 (SEQ ID NO: 11) including splice sites.

FIG. 10 shows the full nucleotide sequence of GntIII without a c-myc tag (SEQ ID NO: 7).

FIGS. 14A and 14B show a MALDI-TOF mass spectra of glycoproteins from (A) control and (B) GnTIII corn plants.

DEFINITIONS

Figure 1A:
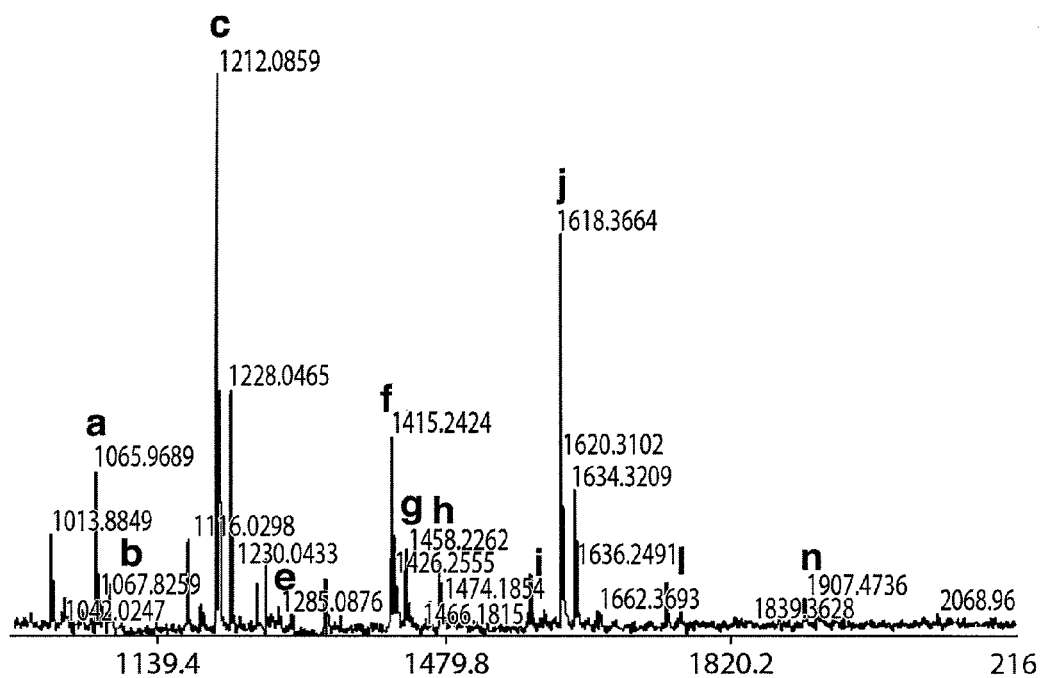
FIGS. 1A and 1B show MALDI-TOF mass spectra of (A) N-linked glycans isolated from leaves of control tobacco plant and (B) N-linked glycans isolated from leaves of selected GnTM-17 tobacco plant transformed with human GnTIII. See, Table 1 for structures.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

The term "glycoprotein" refers to proteins with covalently attached sugar units, either bonded via the OH group of serine or threonine (0 glycosylated) or through the amide NH2 of asparagine (N glycosylated). "Glycoprotein" may include, but is not limited to, for example, most secreted proteins (serum albumin is the major exception) and proteins exposed at the outer surface of the plasma membrane. Sugar residues found include, but are not limited to: mannose, N acetyl glucosamine, N acetyl galactosamine, galactose, fucose and sialic acid.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine (V)-leucine (L)-isoleucine (I), phenylalanine (F)-tyrosine (Y), lysine (K)-arginine (R), alanine (A)-valine (V), and asparagine (N)-glutamine (Q). More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in conceit or which are in close proximity due to folding or other configurations.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides (e.g., ten nucleotides) to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "heterologous" when used in reference to a gene refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise gene sequences that comprise cDNA forms of a gene; the cDNA sequences may be expressed in either a sense (to produce mRNA) or anti-sense orientation (to produce an anti-sense RNA transcript that is complementary to the mRNA transcript). Heterologous genes are distinguished from endogenous genes in that the heterologous gene sequences are typically joined to nucleotide sequences comprising regulatory elements such as promoters that are not found naturally associated with the gene for the protein encoded by the heterologous gene or with gene sequences in the chromosome, or are associated with portions of the chromosome not found in nature (e.g., genes expressed in loci where the gene is not normally expressed).

A "heterologous glycoprotein" is a glycoprotein originating from a species other than the plant host system. The glycoprotein may include but is not limited to antibodies, hormones, growth factors, and growth factor receptors, antigens, cytokines and blood products.

A "plant host system" may include, but is not limited to, a plant or portion thereof which includes, but is not limited to, a plant cell, plant organ and/or plant tissue. The plant may be a monocotyledon (monocot) which is a flowering plant whose embryos have one cotyledon or seed leaf and includes but is not limited to lilies, grasses, corn (*Zea mays*), rice, grains including oats, wheat and barley, orchids, irises, onions and palms. Alternatively, the plant may be a dicotyledenon (dicot) which includes, but is not limited to, tobacco (*Nicotiana*), tomatoes, potatoes, legumes (e.g., alfalfa and soybeans), roses, daises, cacti, violets and duckweed. The plant may also be a moss which includes, but is not limited to, *Physcomitrella patens*. The invention is further directed to a method for obtaining said bisected GlcNAc in a plant host system by introducing a nucleic acid encoding said GnTIII into a plant or portion thereof and expressing said GnTIII and isolating said plant or portion thereof expressing said GnTIII.

The term "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence and other like sequences). The present invention contemplates host cells expressing a heterologous protein encoded by a nucleotide sequence of interest along with one or more hybrid enzymes.

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

As used herein, the terms "complementary" or "complementarity" are used in reference to nucleotide sequences related by the base-pairing rules. For example, the sequence 5'-AGT-3' is complementary to the sequence 5'-ACT-3'. Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands.

A "complement" of a nucleic acid sequence as used herein refers to a nucleotide sequence whose nucleic acids show total complementarity to the nucleic acids of the nucleic acid sequence. For example, the present invention contemplates the complements of SEQ ID NO: 1.

The term "homology" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

When used in reference to a single-stranded nucleic acid sequence, the term "substantially homologous" refers to any probe which can hybridize to the single-stranded nucleic acid sequence under conditions of low stringency as described infra.

The following terms are used to describe the sequence relationships between two or more polynucleotides: "reference sequence," "sequence identity," "percentage of sequence identity" and "substantial identity." A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci. (U.S.A.)* 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+ 0.41$ (% G+C), when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 et NaH$_2$PO$_4$ (H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$ (H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$ (H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0 SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

Additionally, the term "equivalent," when made in reference to a hybridization condition as it relates to a hybridization condition of interest, means that the hybridization condition and the hybridization condition of interest result in hybridization of nucleic acid sequences which have the same range of percent (%) homology results. For example, if a hybridization condition of interest results in hybridization of a first nucleic acid sequence with other nucleic acid sequences that have from 50% to 70% homology to the first nucleic acid sequence, then another hybridization condition is said to be equivalent to the hybridization condition of interest if this other hybridization condition also results in hybridization of the first nucleic acid sequence with the other nucleic acid sequences that have from 50% to 70% homology to the first nucleic acid sequence.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above-listed conditions.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

The term "polymorphic locus" refers to a genetic locus present in a population that shows variation between members of the population (i.e., the most common allele has a frequency of less than 0.95). Thus, "polymorphism" refers to the existence of a character in two or more variant forms in a population. A "single nucleotide polymorphism" (or SNP) refers a genetic locus of a single base which may be occupied by one of at least two different nucleotides. In contrast, a "monomorphic locus" refers to a genetic locus at which little or no variations are seen between members of the population (generally taken to be a locus at which the most common allele exceeds a frequency of 0.95 in the gene pool of the population).

A "frameshift mutation" refers to a mutation in a nucleotide sequence, usually resulting from insertion or deletion of a single nucleotide (or two or four nucleotides) which results in a change in the correct reading frame of a structural DNA sequence encoding a protein. The altered reading frame usually results in the translated amino-acid sequence being changed or truncated.

A "splice mutation" refers to any mutation that affects gene expression by affecting correct RNA splicing. Splicing mutation may be due to mutations at intron-exon boundaries which alter splice sites.

The term "detection assay" refers to an assay for detecting the presence or absence of a sequence or a variant nucleic acid sequence (e.g., mutation or polymorphism in a given allele of a particular gene, as e.g., GnTIII gene, SEQ ID NO: 1, FIG. 4A), or for detecting the presence or absence of a particular protein (e.g., GnTIII, SEQ ID NO: 2, FIG. 4B) or the structure or activity or effect of a particular protein (e.g., GnTIII activity), for detecting glycosylation moieties on a particular protein (e.g., N-linked glycans) or for detecting the presence or absence of a variant of a particular protein.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q3 replicase, MDV-1 RNA is the specific template for the replicase (Kacian et al., Proc. Natl. Acad. Sci. USA, 69:3038, 1972). Other nucleic acid will not be replicated by this amplification enzyme. Similarly, in the case of T7 RNA polymerase, this amplification enzyme has a stringent specificity for its own promoters (Chamberlain et al., Nature, 228:227, 1970). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560, 1989). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press, 1989).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is rRNA. The starting mRNA is enzymatically converted to complementary DNA or "cDNA" using a reverse transcriptase enzyme. The cDNA is then used as a "template" for a "PCR" reaction The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination," "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter" or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. In contrast, a "regulatable" promoter, is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The terms "infecting" and "infection" with a bacterium refer to co-incubation of a target biological sample, (e.g., cell, tissue, etc.) with the bacterium under conditions such that nucleic acid sequences contained within the bacterium are introduced into one or more cells of the target biological sample.

The term "Agrobacterium" refers to a soil-borne, Gram-negative, rod-shaped phytopathogenic bacterium which causes crown gall. The term "Agrobacterium" includes, but is not limited to, the strains Agrobacterium tumefaciens, (which typically causes crown gall in infected plants), and Agrobacterium rhizogens (which causes hairy root disease in infected host plants). Infection of a plant cell with Agrobacterium generally results in the production of opines (e.g., nopaline, agropine, octopine etc.) by the infected cell. Thus, Agrobacterium strains which cause production of nopaline (e.g., strain LBA4301, C58, A208) are referred to as "nopaline-type" Agrobacteria; Agrobacterium strains which cause production of octopine (e.g., strain LBA4404, Ach5, B6) are referred to as "octopine-type" Agrobacteria; and Agrobacterium strains which cause production of agropine (e.g., strain EHA105, EHA101, A281) are referred to as "agropine-type" Agrobacteria.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length.

In contrast, an "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual*, 2nd ed., Cold Spring Harbor Laboratory Press, New York [1989] pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "vector" refers to any genetic element, such as a plasmid, phage, transposon, cosmid, chromosome, retrovirus, virion, or similar genetic element, which is capable of replication when associated with the proper control elements and which can transfer gene sequences into cells and/or between cells. Thus, this term includes cloning and expression vehicles, as well as viral vectors.

The term "expression vector" as used herein refers to a recombinant DNA molecule containing a desired coding sequence (or coding sequences)—such as the coding sequence(s) for the hybrid enzyme(s) described in more detail below—and appropriate nucleic acid sequences necessary for the expression of the operably linked coding sequence in a particular host cell or organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. It is not intended that the present invention be limited to particular expression vectors or expression vectors with particular elements.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, *Virol.*, 52:456, 1973), has been modified by several groups to optimize conditions for particular types of cells. The art is well aware of these numerous modifications.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "plant" as used herein refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including, but not limited to, roots, shoots, leaves, pollen, seeds, tumor tissue and various types of cells in culture (e.g., single cells, protoplasts, embryos, callus, protocorm-like bodies, etc.). Plant tissue may be in planta, in organ culture, tissue culture, or cell culture. Similarly, "plant cell(s)" may be cells in culture or may be part of a plant.

The term "transgenic" when used in reference to a cell refers to a cell which contains a transgene, or whose genome has been altered by the introduction of a transgene. The term "transgenic" when used in reference to a cell, tissue or to a plant refers to a cell, tissue or plant, respectively, which comprises a transgene, where one or more cells of the tissue contain a transgene (such as a gene encoding the hybrid enzyme(s) of the present invention), or a plant whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods described herein.

The term "transgene" as used herein refers to any nucleic acid sequence which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, or other like modifications) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), or other similar elements.

The term "foreign gene" refers to any nucleic acid (e.g., gene sequence) which is introduced into the genome of a cell by experimental manipulations and may include gene sequences found in that cell so long as the introduced gene contains some modification (e.g., a point mutation, the presence of a selectable marker gene, or other like modifications) relative to the naturally-occurring gene.

The term "transformation" as used herein refers to the introduction of a transgene into a cell. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (e.g., β-glucuronidase) encoded by the transgene (e.g., the uidA gene) as demonstrated herein (e.g., histochemical assay of GUS enzyme activity by staining with X-gluc which gives a blue precipitate in the presence of the GUS enzyme; and a chemiluminescent assay of GUS enzyme activity using the GUS-Light kit (Tropix)). The term "transient transformant" refers to a cell which has transiently incorporated one or more transgenes. In contrast, the term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Alternatively, stable transformation of a cell may also be detected by the polymerase chain reaction of genomic DNA of the cell to amplify transgene sequences. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene.

The term "host cell" refers to any cell capable of replicating and/or transcribing and/or translating a heterologous gene. Thus, a "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., *Mol. Cell. Biol.* 7:725, 1987 and U.S. Pat. Nos. 6,074,859; 5,976, 796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31-9.58, 1939).

The term "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52, 1989).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "antigenic determinant" refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "isolated" when used in relation to a nucleic acid, as in "an isolated nucleic acid sequence" refers to a nucleic acid sequence that is identified and separated from one or more other components (e.g., separated from a cell containing the nucleic acid, or separated from at least one contaminant nucleic acid, or separated from one or more proteins, one or more lipids) with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, an isolated nucleic acid sequence comprising, for example, SEQ ID NO:1 includes, by way of example, such nucleic acid sequences in cells which ordinarily contain, for example, SEQ ID NO:1 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

The term "purified" refers to molecules, either nucleic or amino acid sequences, that are removed from their natural environment (or components of their natural environment), isolated or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample. The present invention contemplates both purified (including substantially purified) and unpurified hybrid enzyme(s).

The term "composition comprising" a given polynucleotide sequence or polypeptide refers broadly to any composition containing the given polynucleotide sequence or polypeptide. The composition may comprise an aqueous solution. Compositions comprising polynucleotide sequences encoding GnTIII or fragments thereof may be employed as hybridization probes. In this case, the GnTIII encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "response," when used in reference to an assay, refers to the generation of a detectable signal (e.g., accumulation of reporter protein, increase in ion concentration, accumulation of a detectable chemical product).

The term "sample" is used in its broadest sense. In one sense it can refer to a animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

The term "fusion protein" refers to a protein wherein at least one part or portion is from a first protein and another part or portion is from a second protein. The term "hybrid enzyme" refers to a fusion protein which is a functional enzyme, wherein at least one part or portion is from a first species and another part or portion is from a second species. Preferred hybrid enzymes of the present invention are functional glycosyltransferases (or portions thereof) wherein at least one part or portion is from a plant and another part or portion is from a mammal (such as human).

The term "introduction into a cell" in the context of nucleic acid (e.g., vectors) is intended to include what the art calls "transformation" or "transfection" or "transduction." Transformation of a cell may be stable or transient—and the present invention contemplates introduction of vectors under conditions where, on the one hand, there is stable expression, and on the other hand, where there is only transient expression. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (e.g., antigen binding of an antibody) encoded by the transgene (e.g., the antibody gene). The term "transient transformant" refers to a cell which has transiently incorporated one or more transgenes. In contrast, the term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Alternatively, stable transformation of a cell may also be detected by the polymerase chain reaction (PCR) of genomic DNA of the cell to amplify transgene sequences. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene.

"Bisected oligosaccharide" shall be defined as an oligosaccharide comprising, e.g., two mannose groups and another saccharide moitey attached to a mannose residue of the oligosaccharide. Examples of bisected oligonucleotides are given in Table 1.

DETAILED DESCRIPTION OF THE INVENTION

The GnTIII (for example, SEQ ID NO: 1, FIG. 4A) expressed in the plant host cell of the present invention is a mammalian GnTIII. In a specific embodiment, the GnTIII is a human GnTIII (for example, SEQ ID NO: 2, FIG. 4B). The GnTIII may also in a specific embodiment have 80% identity with the amino acid sequence of a mammalian GnTIII, more preferably at least about 90%, even more preferably at least about 95%, and most preferably at least about 97% (hereinafter "homologous polypeptides"), which qualitative retain the activity of said mammalian GnTIII. A polypeptide that has an amino acid sequence at least, for example, 95% "identical" to a query amino acid sequence is identical to the query sequence except that the subject polypeptide sequence may include on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag, et al. (Com. App. Biosci. 6:237-245, 1990). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest. N- and C-terminal residues of the subject sequence.

The GnTIII expressed in the plant host system of the present invention is encoded by a nucleic acid sequence that has at least 80% identity with the nucleic acid sequence encoding an amino acid sequence of a mammalian GnTIII, more preferably at least about 90%, even more preferably at least about 95%, and most preferably at least about 97% (hereinafter "homologous polypeptides"), which qualitative retain the activity of said mammalian GnTIII. The nucleic acid sequence may be an RNA or DNA sequence.

A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag, et al., (*Comp. App. Biosci.,* 6:237-245, 1990). In a sequence alignment the query and subject sequences are both DNA sequences. An RNA sequence can be compared by converting U's (uridine) to T's (thymines). The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

The invention also encompasses polynucleotides that hybridize to the nucleic acid sequence encoding said mammalian GnTIII. A polynucleotide "hybridizes" to another polynucleotide, when a single-stranded form of the polynucleotide can anneal to the other polynucleotide under the appropriate conditions of temperature and solution ionic strength (see, Sambrook, et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). Moderate stringency hybridization conditions correspond to a higher temperature of 55° C., e.g., 40% formamide, with 5× or 6×SCC. High stringency hybridization conditions correspond to the highest temperature of 65° C., e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ (melting temperature) for hybrids of nucleic acids having those sequences. The relative stability (corresponding to higher $T_m$) of nucleic acid hybridizations decreases in the following order: RNA:RNA, DNA:RNA, DNA:DNA.

Expression of GnTIII and Other Heterologous Proteins in Plant Host Systems

In one embodiment, the nucleic acid encoding the mammalian GnTIII or other heterologous proteins, such as a heterologous glycoprotein or mammalian glycosyltransferase may be inserted into an appropriate expression vector, i.e., a vector which contains the necessary elements for the transcription and translation of the inserted coding sequence, or in the case of an RNA viral vector, the necessary elements for replication and translation, as well as selectable markers. These include but are not limited to a promoter region, a signal sequence, 5' untranslated sequences, initiation codon depending upon whether or not the structural gene comes equipped with one, and transcription and translation termination sequences. Methods for obtaining such vectors are known in the art (see WO 01/29242 for review).

Promoter sequences suitable for expression in plants are described in the art, e.g., WO 91/198696. These include non-constitutive promoters or constitutive promoters, such as, the nopaline synthetase and octopine synthetase promoters, cauliflower mosaic virus (CaMV) 19S and 35S promoters and the figwort mosaic virus (FMV) 35 promoter (U.S. Pat. No. 6,051,753). Promoters used may also be tissue specific promoters targeted for example to the endosperm, aleurone layer, embryo, pericarp, stem, leaves, kernels, tubers, roots, etc.

A signal sequence allows processing and translocation of a protein where appropriate. The signal can be derived from plants or could be non-plant signal sequences. The signal peptides direct the nascent polypeptide to the endoplasmic reticulum, where the polypeptide subsequently undergoes post-translational modification. Signal peptides can routinely be identified by those of skill in the art. They typically have a tripartitite structure, with positively charged amino acids at the N-terminal end, followed by a hydrophobic region and then the cleavage site within a region of reduced hydrophobicity.

The transcription termination is routinely at the opposite end from the transcription initiation regulatory region. It may be associated with the transcriptional initiation region or from a different gene and may be selected to enhance expression. An example is the NOS terminator from *Agrobacterium* Ti plasmid and the rice α-amylase terminator. Polyadenylation tails may also be added. Examples include but are not limited to *Agrobacterium* octopine synthetase signal, (Gielen, et al., *EMBO J.* 3:335-846, 1984) or nopaline synthase of the same species (Depicker, et al., *Mol. Appl. Genet.* 1:561-573, 1982).

Enhancers may be included to increase and/or maximize transcription of the heterologous protein. These include, but are not limited to peptide export signal sequence, codon usage, introns, polyadenylation, and transcription termination sites (see, WO 01/29242).

Markers include herbicide tolerance and prokaryote selectable markers. Such markers include resistance toward antibiotics such as ampicillin, tetracycline, kanamycin, and spectinomycin. Specific examples include but are not limited to streptomycin phosphotransferase (spt) gene coding for streptomycin resistance, neomycin phosphotransferase (nptII) gene encoding kanamycin or geneticin resistance, hygromycin phosphotransferase (hpt) gene encoding resistance to hygromycin.

The vectors constructed may be introduced into the plant host system using procedures known in the art (reviewed in WO 01/29242 and WO 01/31045). The vectors may be modified to intermediate plant transformation plasmids that contain a region of homology to an *Agrobacterium tumefaciens* vector, a T-DNA border region from *A. tumefaciens*. Alternatively, the vectors used in the methods of the present invention may be *Agrobacterium* vectors. Methods for introducing the vectors include but are not limited to microinjection, velocity ballistic penetration by small particles with the nucleic acid either within the matrix of small beads or particles, or on the surface and electroporation. The vector may be introduced into a plant cell, tissue or organ. In a specific embodiment, once the presence of a heterologous gene is ascertained, a plant may be regenerated using procedures known in the art.

Uses of Mammalian GnTIII

The expression of mammalian GnTIII leads to bisected N-glycans on glycoproteins. Bisected N-glycans are important for biological activity of some mammalian glycoproteins. In particular, bisected monoclonal antibodies have enhanced ADCC (antibody-dependent cellular cytotoxicity). Introduction of bisected structures leads to new or optimized functionalities and increased bioavailability of glycoprotein, e.g., increasing the antennary type increases half-life because of reduced clearance by the kidney. Accordingly, the invention is directed to a plant host system comprising said heterologous glycoprotein having bisecting oligosaccharides, particularly bisecting GlcNAc residues and methods for producing said glycoprotein.

Furthermore, expression of GnTIII in plants leads to drastic increase of terminal GlcNAc's compared to wildtype plants (plant N-glycans contain far less GlcNAc residues compared to mammalian N-glycans). More GlcNAc residues on N-glycans of plant glycoproteins or recombinant glycoprotein produced in plants resembles mammalian N-glycans of glycoproteins. The introduction of bisected GlcNAc in plant N-glycans (and in plant-produced recombinant glycoproteins such as Mabs) due to GnTIII expression in plants seems to prevent the N-glycan from degradation by β-N-acetylhexosaminidases. More GlcNAc residues means more acceptor substrate for β(1,4)-galactosyltransferase (GalT) adding terminal galactose. Co-expression of GnTIII and a functional protein such as a transporter or a (mammalian) enzyme or functional fragment thereof providing N-glycan biosynthesis, such as a galactosyltransferase, such as GAlT, or crossing GnTIII plants with GalT plants and vice versa, leads to increased galactosylation of glycoproteins s produced in these plants. Accordingly, the invention is directed to a plant host system comprising said mammalian GnTIII and said functional protein; the plant host system may further comprise a heterologous glycoprotein with increased galactosylation relative to a heterologous glycoprotein produced in a plant host system not comprising said mammalian GnTIII and said functional protein, methods for providing said plant host systems and methods for producing said glycoprotein.

Generating stably transformed plants which produce tailored glycoproteins with commercial interest can be established by inoculating plant cells or tissues with *Agrobacterium* strains containing a vector which comprises both nucleotide sequences encoding GnTIII, optionally N-glycosylation modifying enzymes and nucleotide sequences encoding commercially interesting heterologous glycoproteins or by the procedures described above such as electroporation, microinjection, velocity ballistic penetration by small particles with the nucleic acid either within the matrix of small beads or particles, or on the surface and electroporation. Alternatively, stably transformed plants which produce tailored glycoproteins with commercial interest can be generated by simultaneous inoculation (cotransformation) of two or more *Agrobacterium* strains each carrying a vector comprising either nucleotide sequences encoding GNTIII, optionally, other N-glycosylation modifying enzymes or nucleotide sequences encoding glycoproteins of commercial interest or direct cotransformation of plant cells or tissues with said vectors. Alternatively, stably transformed plants which produce tailored glycoproteins with commercial interest can be generated by (multiple) crossing(s) of plants with modified N-glycosylation with plants which express nucleotide sequences encoding proteins of commercial interest. In all of these procedures, the vector may also comprise a nucleotide sequence which confers resistance against a selection agent.

In order to obtain satisfactory expression of the proteins involved in N-glycosylation, GnTIII and of the glycoproteins or polypeptides of commercial interest, the nucleotide sequences may be adapted to the specific transcription and translation machinery of the host plant as known to people skilled in the art. For example, silent mutations in the coding regions may be introduced to improve codon usage and specific promoters may be used to drive expression of the said genes in the relevant plant tissues. Promoters which are developmentally regulated or which can be induced at will, may be used to ensure expression at the appropriate time, for example, only after plant tissues have been harvested from the field and brought into controlled conditions. In all these cases, choice of expression cassettes of the glycosylation modifying proteins and of the glycoproteins of commercial interest should be such that they express in the same cells to allow desired post translational modifications to the said glycoprotein.

As described above, in a specific embodiment, a plant that can be used in the method of the present invention is a tobacco plant, or at least a plant related to the genus *Nicotiana*, however, use for the invention of other relatively easy transformable plants, such as *Arabidopsis thaliana* or *Zea mays*, or plants related thereto, is also particularly provided. For the production of recombinant glycoproteins, the use of duckweed offers specific advantages. The plants are in general small and reproduce asexually through vegetative budding. Nevertheless, most duckweed species have all the tissues and organs of much larger plants including roots, stems, flowers, seeds and fronds. Duckweed can be grown cheaply and very fast as a free floating plant on the surface of simple liquid solutions from which they can easily be harvested. They can also be grown on nutrient-rich waste water, producing valuable products while simultaneously cleaning wastewater for reuse. Particularly relevant for pharmaceutical applications, duckweed can be grown indoors under contained and controlled conditions. Stably transformed Duckweed can for example be regenerated from tissues or cells after (co)-inoculating with *Agrobacterium* strains containing each a (binary) vector which comprises one or more nucleotide sequences of interest encoding N-glycosylation modifying enzymes and/or genes encoding commercially interesting heterologous glycoproteins. The duckweed plant may, for example, comprise the genus *Spirodella*, genus *Wolffia*, genus *Woffiella*, or the genus *Lemna*, *Lemna minor*, *Lemna miniscula* and *Lemna gibba*. Also mosses such as *Physcomitrella patens* offer advantages in that it can be grown cheaply under contained conditions. In addition the haploid genome of *Physcomitrella patens* is relatively easy to manipulate.

Expression in tomato fruits also offers specific advantages. Tomatoes can be easily grown in greenhouses under contained and controlled conditions and tomato fruit biomass can be harvested continuously throughout the year in enormous quantities. The watery fraction containing the glycoproteins of interest can be readily separated from the rest of the tomato fruit which allows easier purification of the glycoprotein. Expression in storage organs of other crops including but not limited to the kernels of corn, the tubers of potato and the seeds of rape seed or sunflower are also attractive alternatives which provide huge biomass in organs for which harvesting and processing technology is in place. Expression in nectar offers specific advantages with respect to purity and homogeneity of the glycoprotein secreted in the nectar.

Alternatively, a plant comprising a heterologous glycoprotein is crossed with a plant according to the invention comprising GnTIII and optionally at least one functional mammalian protein, e.g., a transporter or an enzyme providing N-glycan biosynthesis that is normally not present in plants, harvesting progeny from said crossing and selecting a desired progeny plant expressing said heterologous glycoprotein and expressing GnTIII and optionally a functional (mammalian) enzyme involved in mammalian-like N-glycan biosynthesis that is normally not present in plants. This process is known as crosspollination. In a preferred embodiment, the invention provides a method according to the invention further comprising selecting a desired progeny plant expressing said recombinant protein comprising bisecting oligosaccharide, particularly galactose residues and/or increased galactosylation. Now that such a plant is provided, the invention also provides use of a transgenic plant to produce a desired glycoprotein or functional fragment thereof, in particular wherein said glycoprotein or functional fragment thereof comprises bisecting oligosaccharide and/or increased galactosylation.

The invention additionally provides a method for obtaining a desired glycoprotein or functional fragment thereof comprising cultivating a plant according to the invention until said plant has reached a harvestable stage, for example when sufficient biomass has grown to allow profitable harvesting, followed by harvesting said plant with established techniques known in the art and fractionating said plant with established techniques known in the art to obtain fractionated plant material and at least partly isolating said glycoprotein from said fractionated plant material. The presence of desired proteins may be screened using methods known in the art, preferably using screening assays where the biologically active site is detected in such a way as to produce a detectable signal. This signal may be produced directly or indirectly. Examples of such assays include ELISA or a radioimmunoassay.

The introduction of bisected GlcNAc residues due to expression of GnTIII can also be used for the prevention of removal (degradation) of saccharides from N-glycan by "blocking" activity glycosidases, e.g., β-N-acetylhexosaminidases and preventing the addition of other saccharides (driven by "other" subsequent glycosyltransferase genes) to N-linked glycan, e.g., fucosylation, xylosylation. By controlling localization (e.g., by providing other subcellular targetting signals) and/or controlling expression levels (e.g., varying levels in independent transgenic plants or using different promoter) glycoform composition could be modulated. Hence introduction of bisecting GlcNAc residues in glycoproteins in plants including recombinant glycoproteins, inhibits incorporation α-1,3-fucose by blocking activity α1,3fucosyltransferase, α-1,4-fucose by blocking α-1,4-fucosyltransferase, β-1,2-xylose by blocking β-1,2-xylosyltransferase, β-1,3-galactose by blocking β-1,3-galactosyltransferase and removal/degradation of saccharides added to the N-glycan especially terminal GlcNAc residues by blocking activity of β-N-acetylhexosaminidases and terminal β-1,4-galactose (added by expression of β-1,4-galactosyltransferase as provided by patent application WO 01/31045) by blocking β-1,4-galactosidase. Thus in this way, controlled expression of GnTIII and controlled introduction of bisecting GlcNAc residues can be used to steer glycoform composition and/or limit glycoform heterogeneity.

Modified GnTIII and GnTIII Hybrid Proteins

The invention is further directed to an isolated hybrid protein comprising a catalytic portion of mammalian GnTIII and a transmembrane portion of a protein, said protein residing in endoplasmic reticulum or Golgi apparatus of a eukaryotic cell. The invention is also directed to a modified mammalian GnTIII, wherein the transmembrane domain is removed but comprising a retention signal such as KDEL (SEQ. ID. NO.: 28) for retention of said GnTIII in the ER.

A nucleic acid sequence encoding a hybrid enzyme comprising a transmembrane portion of a first enzyme and a catalytic portion of a second enzyme may be obtained as follows. The sequence encoding the transmembrane portion is removed from the second enzyme, leaving a nucleic acid sequence comprising a nucleic acid sequence encoding the C-terminal portion of the second enzyme, which encompasses the catalytic site. The sequence encoding the transmembrane portion of the first enzyme is isolated or obtained via PCR and ligated to the sequence encoding a sequence comprising the C-terminal portion of the second enzyme.

Nucleic acid sequence encoding a protein, particularly enzymes such as galactosyltransferases, mannosidases and n-acetylglucosamine transferases that are retained in the ER may be obtained by removing the sequence encoding the transmembrane fragment and substituting it for a methionine (initiation of translation) codon and by inserting between the last codon and the stop codon of galactosyltransferase the nucleic acid sequence encoding an ER retention signal such as the sequence encoding KDEL (SEQ. ID. NO.: 28) (amino acid residue sequence: lysine-aspartic acid-leucine) (rothman, 1987).

Besides controlling expression, relocalization of GnTIII activity may also be controlled by making a fusion of the gene sequence coding for the enzymatic part of GnTIII with a transmembrane domain of other glycosyltransferases or enzymes/proteins residing in the endoplasmic reticulum (ER) or Golgi apparatus membrane, or by adding so-called retention signal such as but not limited to KDEL for retention in the ER. Such relocalization modulates the addition of specific saccharides to the N-linked glycan of glycoproteins including recombinant glycoprotein and the prevention of removal of these.

Figure 2:
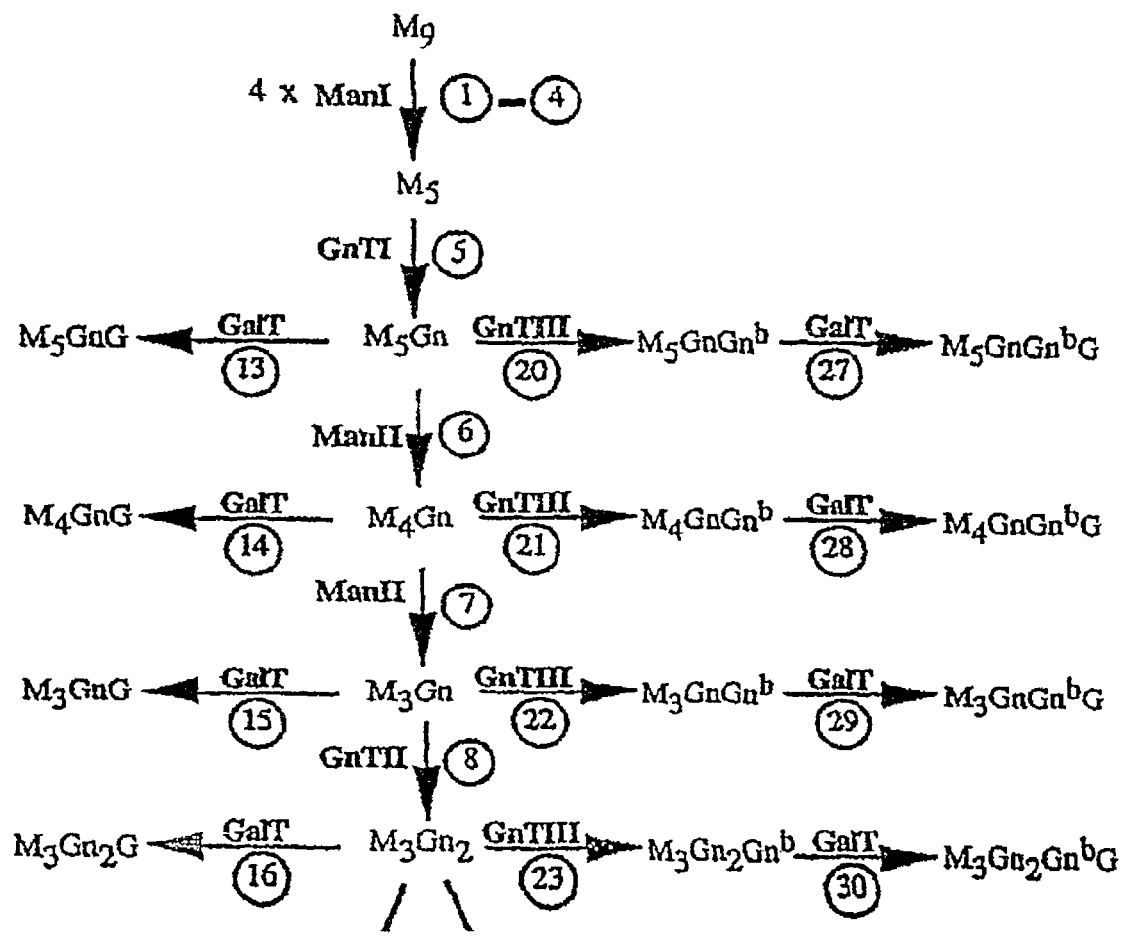
FIG. 2 shows processing of high mannose type glycan (M9) to complex type glycans under the subsequent action of ManI, GnTI, ManII, and GnTII. It is also indicated what glycan structures the action of GalT and/or GnTIII at different points in chain of reactions would lead. The reactions catalyzed by fucosyltransferases and xylosyltransferases are not indicated. Core GlcNAc (Gn) is not indicated. Gn=GlcNAc, $Gn^b$=bisecting GlcNAc, G=galactose and M=mannose.

The exchange of transmembrane domain of GnTIII with that of, for example, GnTI (TmGnTI), mannosidase II (TmManII) xylosyltransferase (TmXyl) or α-1,3 fucosyltransferase (TmFuc) but not limited to these, enables earlier expression of GnTIII and introduction of bisecting GlcNAc at positions 20 to 22 in FIG. 2. This prevents the action of subsequent glycosyltransferases such as xylosyltransferase and fucosyltransferase to act on the substrate leading to glycoforms lacking Xyl and Fuc. Importantly, the additional of terminal galactose by the action of β-1,4)-galactosyltransferase (GalT) is not inhibited by the bisecting GlcNAc-Co-expression of GalT (Bakker, et al., "Galactose-extended glycans of antibodies produced by transgenic plants" *Proc. Nat, Acad. Sci. USA* 98:2899-2904, 2001) results in structures similar as indicated to the right of the arrows annotated with 20, 21 and 22 in FIG. 2. Although devoid of immunogenic xylose and fucose residues, these structures have only one arm processed to complex type glycans. To allow conversion of also the other arm, in addition to relocating GnTIII, also Mannosidase II (ManII) and GnTII are relocated in the Golgi to act earlier in the glycan processing sequence. This can be established in several ways. For example, by exchanging their respective transmembrane domains by that of GnTI (TmGnTI), which results in relocation to position indicated 5 in FIG. 2. Alternatively, both MarnII and GnTII can be relocalised to the ER by removing the transmembrane Golgi targeting domain and supplying the remaining enzyme fragments with a C-terminal ER retention signal (e.g., the amino acid residues KDEL). A plant expressing GalT (Bakker, et al., "Galactose-extended glycans of antibodies produced by transgenic plants" *Proc. Nat. Acad. Sci. USA* 98:2899-2904, 2001) as well as the relocated versions of GnTIII (e.g., TmXyl-GnTIII), ManII (e.g., TmGnTI-ManII) and GnTII (e.g., TmGnTI-GnTII) can than be crossed with plants expressing the recombinant glycoprotein of interest (FIG. 3) or can be retransformed with the gene encoding the glycoprotein of interest such as the genes encoding an antibody. This allows the production of recombinant glycoproteins having bisected glycans with terminal galactose residues which are devoid of xylose and fucose. Transformation procedures and crossing (co-pollination) procedures are described above.

In another embodiment, GnTIII with transmembrane domain of Mannosidase II (TmManII-GnTIII) or xylosyltransferase (Tmxyl-GnTIII) combined with TmXyl-GalT, TmGnTI-GnTII, TmGnTI-ManII. This combination could either be obtained by coexpression or by combining through cross-pollination of the genes involved and leads to glycoproteins including recombinant glycoproteins, lacking xylose and fucose on the core sequence but having bisected GlcNAc residues on the trimannosyl core and terminal galactose.

EXAMPLES

The effect of the introduction of GnTIII in plants on the occurrence of bisected oligosaccharides on the glycans of plant glycoproteins has been evaluated. The human gene for GnTIII has been cloned, and a C-terminal c-myc tag for analysis of expression of the tagged fusion protein has been provided and the whole has been placed under control of plant regulatory elements for introduction in tobacco. It is shown that GnTIII is expressed in plants and that expression results in bisected oligosaccharide structures on endogenous plant glycoproteins. The amount of N-glycans containing at least two GlcNAc residues more than doubled compared to those found in normal tobacco plants. Remarkably, the expression of GnTIII also resulted in a significant reduction of complex type N-glycan degradation products as apparent from matrix-assisted laser desorption ionization time-of-flight (MALDI-TOF) analyses of the isolated glycans of endogenous plant glycoproteins. These data suggest that expression of GnTIII in tobacco resulting in the introduction of bisected structures on N-glycans protects the glycans from degradation by β-N-acetylhexosaminidases. β-N-acetylhexosaminidases have broad specificity for non-reducing terminal GlcNAc and β-N-acetylglucosamine (GalNAC) cleaving amongst others GlcNAc-β1-2 linkages typically present on the trimannosyl core (Man-α-1-3 and Man-α-1-6).

Example 1

Plasmids and Plant Transformation

PAC clone RP5-1104E15 GnTIII (SEQ ID NO: 1, FIG. 4A) was obtained from Pieter J. de Jong, Children's Hospital Oakland Research Institute (CHORI) and is available on request through Sanger Center being part of clone set HBRC-1. sc. The clone clone originates from Homo sapiens, male, blood and can be requested via the Sanger Center's website (from Human chromosome 22q12. 3-13.1; The Wellcome Trust Sanger Institute, Wellcome Trust Genome Campus, Hinxton, Cambridge, CB 10 1 SA, UK; www.sanger.ac.uk).

The human gene for GnTIII was cloned from said PAC clone by PCR using AccuTaq LA DNA polymerase (SigmaAldrich) and primers GNT3F (5' atactcgagttaacaatgaagat-gagacgct-3; SEQ ID NO: 3) and GNT3Rmyc (5'-tatggatc-ctaattcagatcctcttctgagatgag-3; SEQ ID NO: 4). Oligos were from Eurogentec (Belgium). PCR was performed on a PerkinElmerCetus 480 thermal cycler (ABI/PE) using optimal conditions for the AccuTaq polymerase according to the manufacturer. The resulting fragment was cloned in EcoRV site of pBluescribe SK+ (Stratagene, Inc., La Jolla, Calif. USA) and sequence verified. Sequencing was performed using fluorescently labelled dideoxynucleotides essentially as described (Sanger, et al., "DNA sequencing with the dideoxy chain-terminating inhibitors" *Proc. Nat. Acad. Sci. USA* 74:5463-5467, 1977) and reaction mixtures were run on an Applied Biosystems 370A or 380 automated DNA sequencer. Data were analysed using different software modules freely available on the web and compared with the DNA sequence of human GnTIII present in the database.

A 1.6 kb HpaI/BamHI fragment containing the GnTIII gene with C-terminal c-myc tag was subsequently cloned into the Sma/BglII site of pUCAP35S (Van Engelen, et al., "Coordinate expression of antibody subunit genes yields high levels of functional antibodies in roots of transgenic tobacco" *Plant Molecular Biology* 26:1701-1710, 1994) and named pAMV-GnTIII. The cauliflower mosaic virus 35S (CaMV35S) 20 promoter expression cassette with modified GnTIII gene was subsequently cloned as a AscI/PacI fragment in the binary vector pBINPLUS (Van Engelen, et al., "Coordinate expression of antibody subunit genes yields high levels of functional antibodies in roots of transgenic tobacco" *Plant Molecular Biology* 26:1701-1710, 1994) resulting in pBINPLUSGnTIII and introduced in *Agrobacterium tumefaciens* strain Ag10 by electroporation. Transformation of *Nicotiana tabacum* variety Samsun NN was as described before (Horsch, et al., "A simple and general method for transferring genes into plants" *Science* 227:1229-1231, 1985). Sixteen independent transgenic plants were selected and grown to maturity in the greenhouse as described. Leaf material was analysed for expression of GnTIII (SEQ ID NO: 2, FIG. 4B) and glycan composition of endogenous cellular glycoproteins.

Example 2

Analysis of Expression

Total protein extracts of tobacco leaves were prepared as described before (Bakker, et al., "Galactose-extended glycans of antibodies produced by transgenic plants" *Proc. Nat. Acad. Sci. USA* 98:2899-2904, 2001). The amount of protein present in samples was estimated by the Bradford method (Bradford, M. M., "A rapid and sensitive method for the quantitation of microgram quantities of protein utilizing the principle of protein-dye binding" *Anal Biochem* 72:248-254, 1976) using bovine serum albumin as standard. Fixed amounts of protein samples were run on precast 10 or 12% SDS-PAGE gels (Bio-Rad) under reduced conditions. Rainbow coloured molecular weight protein markers were from Amersham. Western blot analysis was performed essentially as described (Bakker, et al., "Galactose-extended glycans of antibodies produced by transgenic plants" *Proc. Nat. Acad. Sci. USA* 98:2899-2904, 2001). Separated proteins were transferred to nitrocellulose (13A85, Schleicher and Schuell or Trans-Blot Transfer Medium, Bio-Rad) using a Bio-Rad Mini Trans-blot Electrophoretic Transfer Cell in 3[cyclohexylamino]-1-propanesulfonic acid (CAPS) buffer for 60 min. Expression of the GnTIII-c-myc fusion protein was analysed by affinoblotting using a peroxidase labelled c-myc antibody. Introduction of bisecting oligosaccharides in endogenous tobacco glycoproteins was visualized by incubation with biotinylated erythroagglutinating phytohemagglutinin (E-PHA; Vector Laboratories). Detection was performed by enhanced chemiluminescence using Lumi-Light Western Blotting Substrate from Roche (Roche Diagnostics GmbH, Mannheim, Germany) on a Lumi-Imager F 1 apparatus (Boehringer Mannheim GmbH, Mannheim, Germany) using LumiAnalyst software (version 3.0).

Example 3

Matrix-Assisted Laser Desorption Ionization Time-of-Flight (MALDI-TOF) Mass Spectrometry For the analysis of glycan structure cellular proteins were isolated from tobacco leaves of a selected plant transformed with human GnTIII (GnTIII-17). Protein isolation and N-glycan preparation were performed as described (Elbers, et. al., 2001). The N-glycans were desalted on a nonporous, graphitized carbon-black column (Carbograph Ultra Clean Tubes, Alltech Associates) before mass spectrometry analysis as described. MALDI-TOF spectra were measured on a MICROMASS (Manchester, U. K.) Tofspec E MALDI-TOF mass spectrometer. Mass spectra were performed in positive mode by using 2,5-dihydroxybenzoic acid as the matrix essentially as described (Elbers, et al., 2001).

Expression of human GnTIII introduces bisecting N-glycans on endogenous glycoproteins in *N. tabacum*. Human GnTIII was introduced in tobacco plants by *Agrobacterium*-mediated transformation of binary vector pBINPLUSGnTIII containing a cDNA harbouring the complete coding sequence fused to a C-terminal c-myc tag under control of the constitutive CaMV35S promoter. Sixty independent transgenic shoots selected for kanamycin resistance were obtained which were analysed for expression of the GnTIII-c-myc fusion protein using the c-myc antibody. Analysis revealed that all expressed the gene at various levels. Fourteen were selected, rooted and transferred to the greenhouse. One plant (GnTIII-17) selected for high expression of the GnTIII-c-myc fusion protein using the c-myc antibody was analysed for the occurrence of bisected GlcNAc residues on N-glycans of endogenous tobacco glycoproteins using a specific binding assay with the biotinylated lectin E-PHA. SDS-PAGE of protein extracts followed by transfer to nitrocellulose and analysis using the specific binding assay with the biotinylated E-PHA lectin revealed that endogenous tobacco glycoproteins of GnTIII-17 contained bisected oligosaccharides whereas those of control tobacco did not. GnTIII-17 was multiplied in the greenhouse for further detailed analysis of glycan structure by MALDI-TOF.

Example 4

Figure 1B:
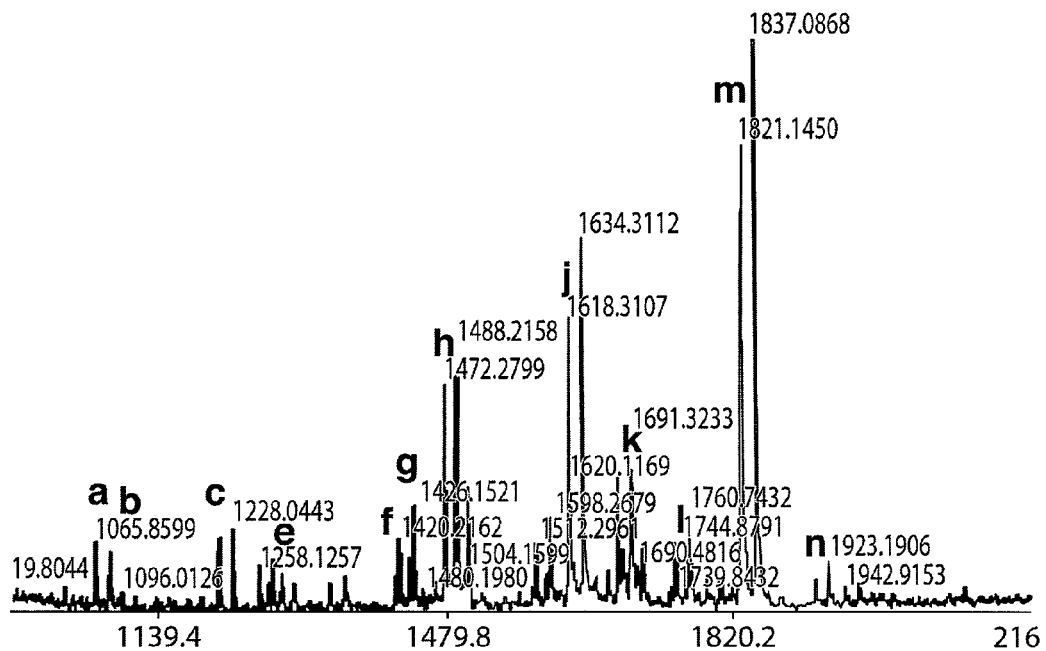

Oligosaccharide Distributions and Level of Bisected Complex Oligosaccharides in Wildtype and Selected Transgenic GnTIII-17 Tobacco Plant Endogenous glycoproteins were isolated from young leaves of control tobacco plant and the selected GnTIII-17 plant to investigate in detail the effect of expression of human GnTIII on the structure of glycans N-linked to glycoproteins. A comparison of the structures of the N-glycans isolated from glycoproteins present in leaves of control wild-type tobacco plants with those from plant GnTIII-17 using MALDI-TOF is represented in FIG. 1. MALDI-TOF allows for the detection of different molecular species in the pool of the N-glycans (glycoforms) and shows a mixture of ions that were assigned to (M+Na)+ adducts of high-mannose (Man)-type N-glycans ranging from d, Man5 to n, Man9 and of mature N-glycans from the truncated structure a, XM3GN2 to m, GN3FXM3GN2 (for structure see Table 1; for a summary of the data see, Table 2). In addition to the N-glycans characterized in the control plants (FIG. 1A), the MALDI-TOF MS of the glycan mixture from plant GnTIII-17 (FIG. 1B) showed at least two ions assigned to N-linked glycans that result from the action of the human GnTIII enzyme (for a comparison see Table 1 and Table 2). These oligosaccharides, GN3XM3GN2 (i) and GN3FXM3GN2 (k) representing 8% and 31% respectively of the population, contain three GlcNAc residues each linked to one of the three mannoses of the trimannosyl core structure of the N-linked glycan.

Analysis of glycan structure through MALDI-TOF as performed here cannot distinguish between GlcNAc residues β(1,2)- or β(1,4)-linked to mannose. Hence, it was not clear if or to what extent the structures GN2XM3GN2 and GN2FXM3GN2 have bisecting oligosaccharides. Additional experiments are required to reveal that these structures are a mix of normal and bisected oligosaccharides or a single compound.

In the light of the observed lethality of CHO cell that overexpress GnTIII (Umana, et al., "Engineered glycoforms of an antineuroblastoma IgG1 with optimized antibody-dependent cellular cytotoxic activity" *Nature Biotechnology* 17:176-180, 1999), remarkably transgenic plants having significant amounts of bisected glycans look phenotypically normal and are completely fertile (can be cross-pollinated and self-pollinated).

Example 5

Expression of Human GnTIII in Tobacco Seems to Protect N-Glycans from Degradation by D-Nacetylhexosaminidases and More than Doubles Terminal N-Glucosaminylation MALDI-TOF analysis of extracts clearly showed that at least 40% of the population of glycoforms now has a bisecting GlcNAc in complex-type N-linked glycans of cellular tobacco proteins through the action of the GnTIII enzyme. Moreover 70% of the population of complex-type N-linked glycans of endogenous glycoproteins of GnTIII-17 has two or three terminal GlcNAc residues compared to about 30% for wildtype tobacco (Table 1). The observed de novo synthesis of at least 40% bisected complex-type N-linked glycans upon expression of GnTIII in tobacco (FIG. 1B, Table 1 and Table 2) coincides with the disappearance of mainly FXM3GN2 (b, from 30% to 4%) and GNFXM3GN2 (f, from 10 to 2%) and to a minor degree GN2FXM3GN2 (j, from 29% to 19%). In addition it also coincides with a significant increase in GN2XM3GN2 (h) from 4% in wildtype tobacco to 14% in GnTIII-17. Whether the latter GN2XM3GN2 (h) in GnTIII plants has the second GlcNAc linked to the (β-linked mannose of the trimannosyl core of the N-linked glycan and hence is the result of GnTIII activity, or to the second α-linked mannose of the trimannosyl core remains to be investigated (see above).

Saccharides a, b and c accounting for 40% of the N-linked glycans in wildtype tobacco plants, are degradation products expected to have arisen from mature glycans of endogenous tobacco glycoproteins after GnTI activity since an *Arabidopsis thaliana* mutant lacking GnTI activity did not contain xylose and fucose residues in the N-glycans of endogenous glycoproteins (Von Schaewen, et al., "Isolation of a mutant *Arabidopsis* plant that lacks N-Acetylglucosaminyl transferase I and is unable to synthesize golgi-modified complex N-linked glycans" *Plant Physiology* 102:1109-1118, 1993). The 7-fold decrease (40%>6%) in these structures in GnTIII-17 together with the threefold reduction of GNXM3GN2 and XM3GN2 (12%>4%) suggests that the introduction of a bisected GlcNAc protects the mature N-linked glycan from degradation by endogenous glycosidases especially β-Nacetylhexosaminidases that removes terminal GlcNAc. The total amount of N-linked glycans expected to have arisen from degradation of mature, full-length N-linked glycans has hence decreased fivefold (from 52% to 10%).

Example 6

Vector Construction and DNA Preparation for Maize Transformation

The human GNTIII gene along with its 3' c-myc immuno-detection tag was obtained by PCR from plasmid pAMV-GNTIII by the following method. Primers MS20 and MS19 homologous to the 5' and 3' ends of the hGNTIII gene respectively, were designed and synthesized to add a Pme1 site and a stop codon to the 3' end of the gene.

```
MS20 (5' Nco1 site):
                                          (SEQ ID NO: 5)
5'-CCATGGTGATGAGACGCTAC-3'

MS19 (adds stop and Pme1 site 3'):
                                          (SEQ ID NO: 6)
5'-GTTTAAACCTAGGATCCTAATTCAGATCCTCT-3'
```

Figure 5A:
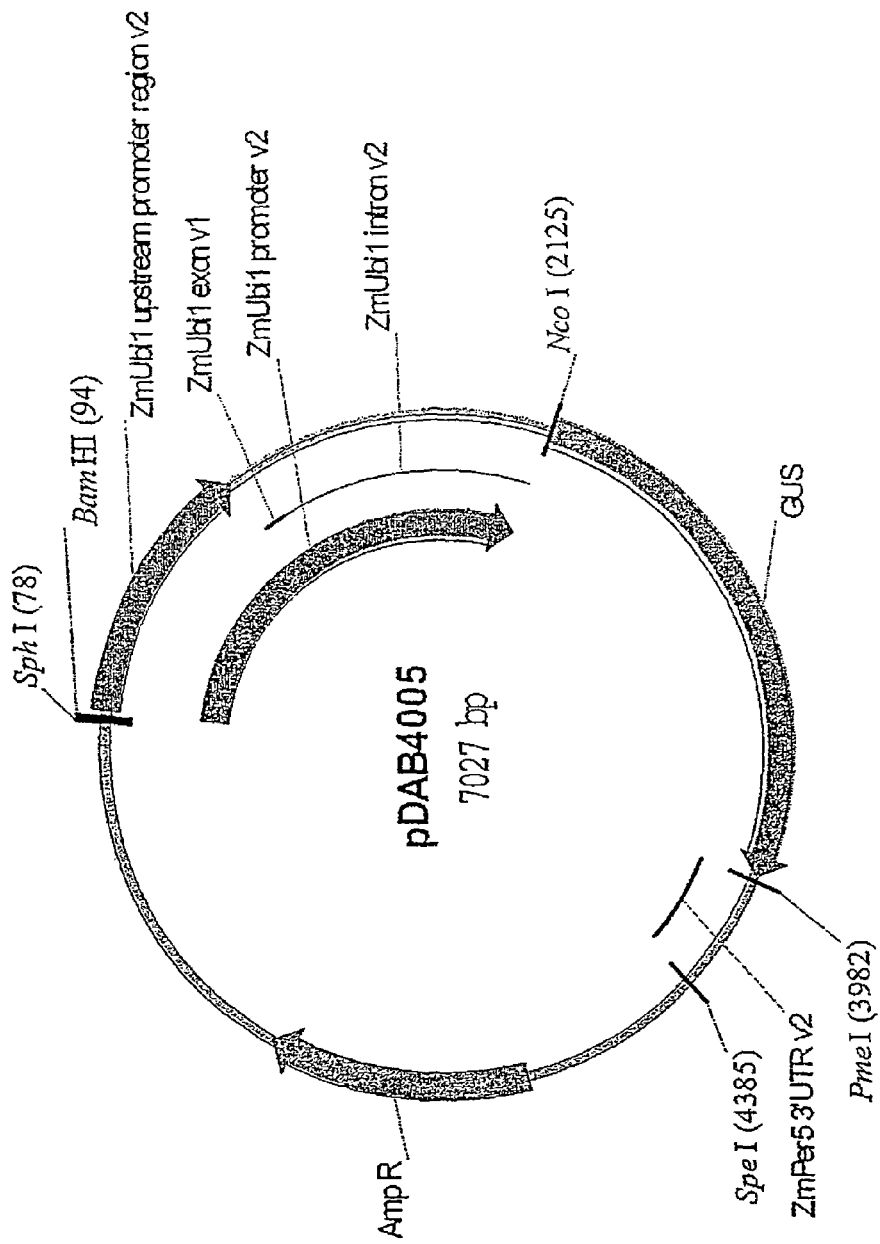

Following gel electrophoresis to identify the correct sized PCR product, the 1.6 kbp PCR product was recovered from the gel with a QIAQUICK Gel Extraction Kit (Qiagen, Valencia, Calif.). Plasmid 4005 (see, SEQ ID NO: 8) (FIGS. 5A and 5B), which contains a Zmubi/GUS/per5 cassette (Christensen, et al., Plant Molec. Biol. 18: 675-689, 1992), was digested with Nco 1 and Pmel to release the GUS gene and the vector fragment was recovered from a gel with a QIAQUICK Gel Extraction Kit (Qiagen, Valencia, Calif.).

Figure 6A:
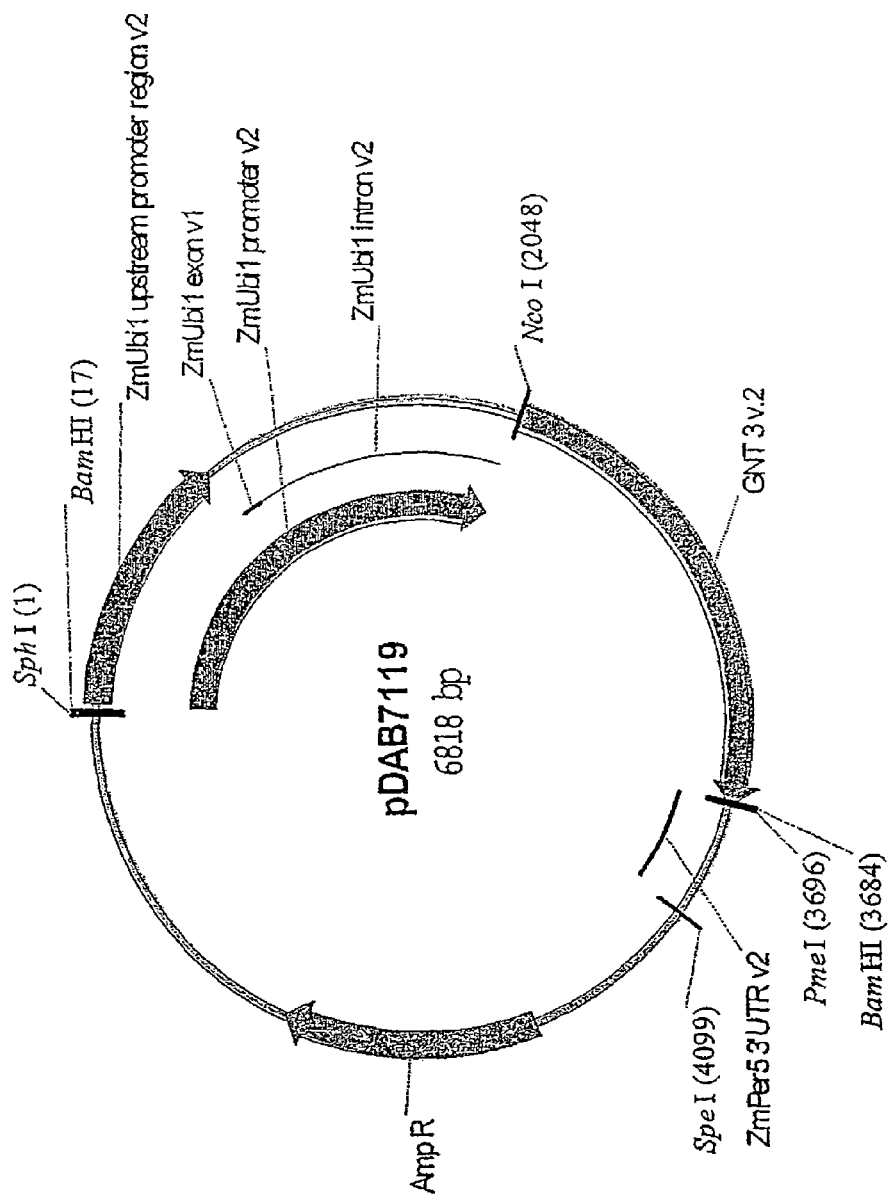

Following digestion with Nco1 and Pme1, the PCR-derived hGNTIII fragment was ligated to the vector fragment left after digestion of pDAB4005 with Nco1 and Pme1, to create the intermediate plasmid pDAB7119 (see, SEQ ID NO: 9) (FIGS. 6A and 6B). Intermediate plasmid pDAB7119 was cut with Spe1 and Sph1 to release the hGNTIII plant expression cassette, which was treated with T4 DNA polymerase to create blunt ends.

Figure 7A:
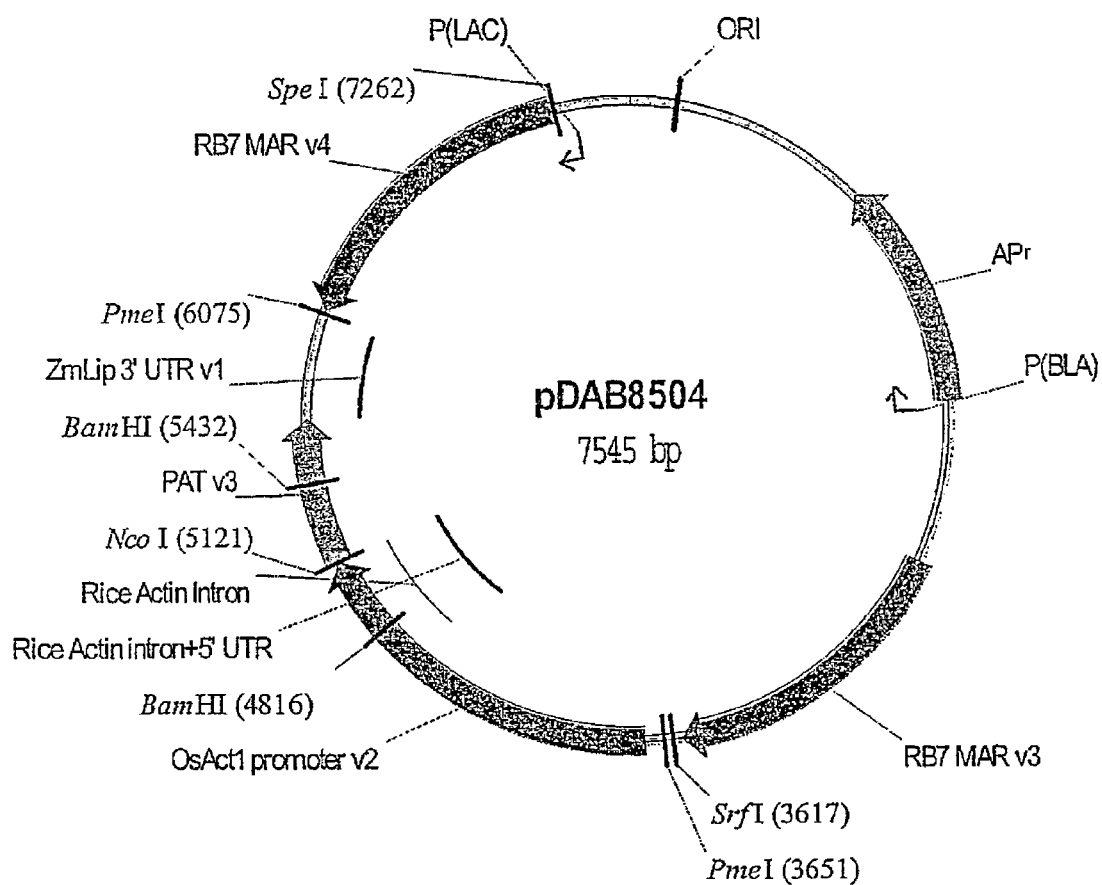
Figure 8A:
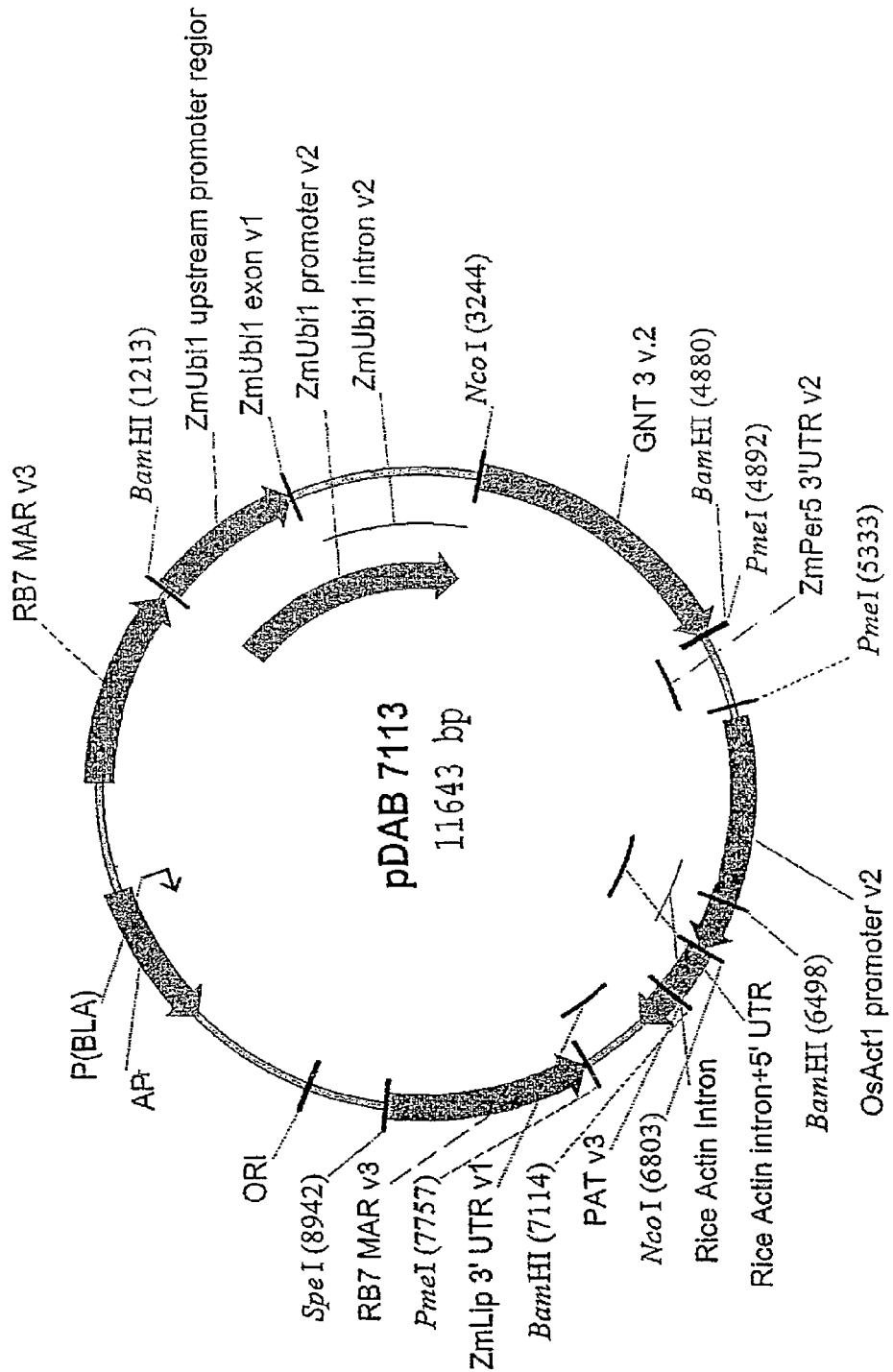

Plasmid pDAB8504 (SEQ ID NO: 10) (see, FIGS. 7A and 7B), which contains the RB7 MAR sequences, was digested with Srf1 and blunt ended with T4 DNA polymerase. Following treatment with calf intestinal phosphatase, the treated 8504 fragment and the hGNTIII plant expression cassette were ligated to create plasmid pDAB 7113 (SEQ ID NO: 10) (see, FIGS. 8A and 8B), which contains RB7 MAR sequences flanking the gene of interest and the selectable marker cassette as follows: RB7 MAR//Zmubi promoter/hGNTIII/per5 3'UTR//Rice actin promoter (D. McElroy, et al., "Isolation of an efficient actin promoter for use in rice transformation" *The Plant Cell* 2:163-171, 1990)/PAT/Zm lipase 3'UTR//RB7 MAR.

The integrity of the GNTIII sequence was checked by sequencing (Big Dye Terminator Cycle Sequencing Ready Reaction, Applied Biosystems, Foster City, Calif.) and was confirmed to encode the human GNTIII enzyme. One base change, G384→384, was found but this substitution does not affect the encoded amino acid, proline 128.

Plasmid pDAB7113 was grown up in 2 L of medium (LB+ amp) and purified with Qiagen plasmid Giga kit to produce 5 milligrams of purified plasmid for plant cell transformation.

Example 7

Transformation of Maize Cells

Plasmid pDAB7113 was introduced into maize cells with WHISKERS-mediated DNA transfer essentially as described in these citations, and as follows (Frame, B., et al., "Production of fertile transgenic maize plants by silicon carbide whisker-mediated transformation" *Plant J.* 6:941-948, 1994; Thompson, J., et al., "Maize transformation utilizing silicon carbide whiskers: a review" *Euphytica* 85:75-80, 1995; P. Song, C. Q. Cai, M. Skokut, B. Kosegi, and J. Petolino, "Quantitative real-time PCR as a screening tool for estimating transgene copy number in Whiskers-derived transgenic maize" *Plant Cell Rep.* 20:948-954, 2002; both of which are incorporated herein by reference).

Embryogenic maize suspension cell cultures were subcultured on medium G-N6 (N6 medium containing 30 gm/L sucrose, 100 mg/L inositol, and 2 mg/L 2,4-D) the day before whisker mediated transformation. On the day of the experiment, cells were pretreated with osmoticum by shaking with medium G-N6 containing 0.2 Molar each mannitol and sorbitol for 30 minutes. Thirty six mls of cells were transferred to a 250 ml centrifuge bottle in 50 ml of medium G-N6, to which was added 8.1 ml of a 5% (w/v) silicon carbide whiskers suspension (Silar SC-9, Advanced Composite Materials, Greer, S.C.) in medium, plus 170 ul of 1 mg/ml plasmid solution (in TE buffer). The centrifuge bottle containing cells, whiskers and DNA was agitated vigorously on a modified Red Devil brand paint mixer for 10 seconds. Whiskered cells were then shaken for two hours in medium with half the level of added osmoticum. Whiskered cells were recovered by filtration on a sterile Buchner funnel and the filter papers were placed on semisolid G-N6 medium for 1 week. After 1 week the filters were moved to semisolid G-N6 medium containing 1 mg/L Herbiace (a commercial formulation of 20% bialaphos, Meiji Seika, Tokyo, Japan). Two weeks later, the cells were removed from the filter paper, mixed with melted G-N6+1 mg/L Herbiace (G-N6+1H) medium also containing 7 gm/L SEAPLAQUE agarose (BioWhittaker, Rockland, Me.), and spread on top of G-N6+1H solid medium. Plates were cultured in the dark at 30° C. Colonies resistant to the selective agent were recovered 5-7 weeks post embedding, and individually moved to fresh G-N6+1H medium for further increase of tissue mass.

Example 8

Molecular Analysis for Copy Number of Inserted DNA

Tissue from each transgenic isolate was individually freeze-dried in a lyophilizer and DNA was extracted by a standard method (DNEASY 96 Plant Kit, Qiagen). The copy number of inserted transgenic DNA was estimated by the Invader Operating System, available from Third Wave Technologies (Third Wave Technologies, Madison, Wis., twt-.com). Primers were designed by the Third Wave Technologies company specifically for the PAT selectable marker and its copy number was estimated relative to genomic DNA copy number for the endogenous maize alpha-tubulin gene.

Example 9

Test Transgenic Maize Callus for Altered Lectin Binding Due to Expression of the GntIII Gene Callus samples from 100 individually isolated unique transgenic events were extracted as follows. Samples from each event were fresh frozen in 96-well cluster tube boxes (Costar Costar 1.2 ml polypropylene, with lid) along with a steel and a tungsten bead in each well. 450 ul of extraction buffer (25 mM sodium phosphate pH6.6, 100 mM NaCl, 30 mM sodium bisulfate, 1% v/v Triton X-100) was added per well and the box of samples was pulverized for 3 minutes full speed on a Kleco Bead Mill. The plate was centrifuged (4° C.) at 2500 rpm for 10 minutes. Extracts were removed to a 96-well deep well plate and frozen for storage. All screening assays were performed on these extracts of individual events.

Protein analyses (microtiter plate protocol, BioRad 500-0006) were made to determine the total protein for each extract. 25 ug protein per sample were loaded in 20 ul loading buffer (Laemmli, U.K. Nature 277:680 (1970)). Gels (4-20%

Criterion PAGE gels, 12+2 wells, BioRad 345-0032) were electrophoresed at 65 mA in Tris/glycine/SDS running buffer (BioRad 161-077). After soaking in transfer buffer (running buffer plus 20% v/v methanol) for 10 minutes, the gels were transferred to nitrocellulose membranes using a semi-dry blotter (150 mA/1.5 hrs). The membranes were incubated for 30 minutes in blocking buffer (20 mM Tris, 144 mM NaCl, 0.5% v/v Tween 20, 10% w/v nonfat powdered milk) at room temperature, then the blocking buffer was removed and replaced with the primary detection lectin (Phaseolus hemagglutinin E, biotinylated, Vector Laboratories B-1125) 2.5 ug/ml in blocking buffer. The primary detection lectin was incubated on the membrane for 1 hour at room temperature. The primary detection solution was removed, the membrane was rinsed once with blocking buffer and the secondary detection solution was added (avidin-HRP, BioRad 170-6528, at 1:5000, plus molecular weight marker detection agent, StrepTactin-HRP, BioRad 161-0380 at 1:10,000 in blocking buffer. The secondary detection reagent was incubated on the membrane for 1 hour at room temperature. During the blocking, primary, and secondary reagent steps the solutions were mixed on the blots. The secondary detection reagent was then removed and the membrane was rinsed with Tris buffered saline (20 mM Tris, 144 mM NaCl) containing 0.5% Tween 20 three times at 10 minutes each and once more for 5 minutes. After dripping off the excess rinse solution, the blot was soaked in substrate ECL (Pierce 34080) for 1 minute, excess ECL solution was drained off, and the membrane was exposed to film. Negative controls were included in each gel to discriminate new glycoprotein bands now visible with this bisecting glycan-detecting lectin reagent on the transgenic callus extracts.

Figure 12:
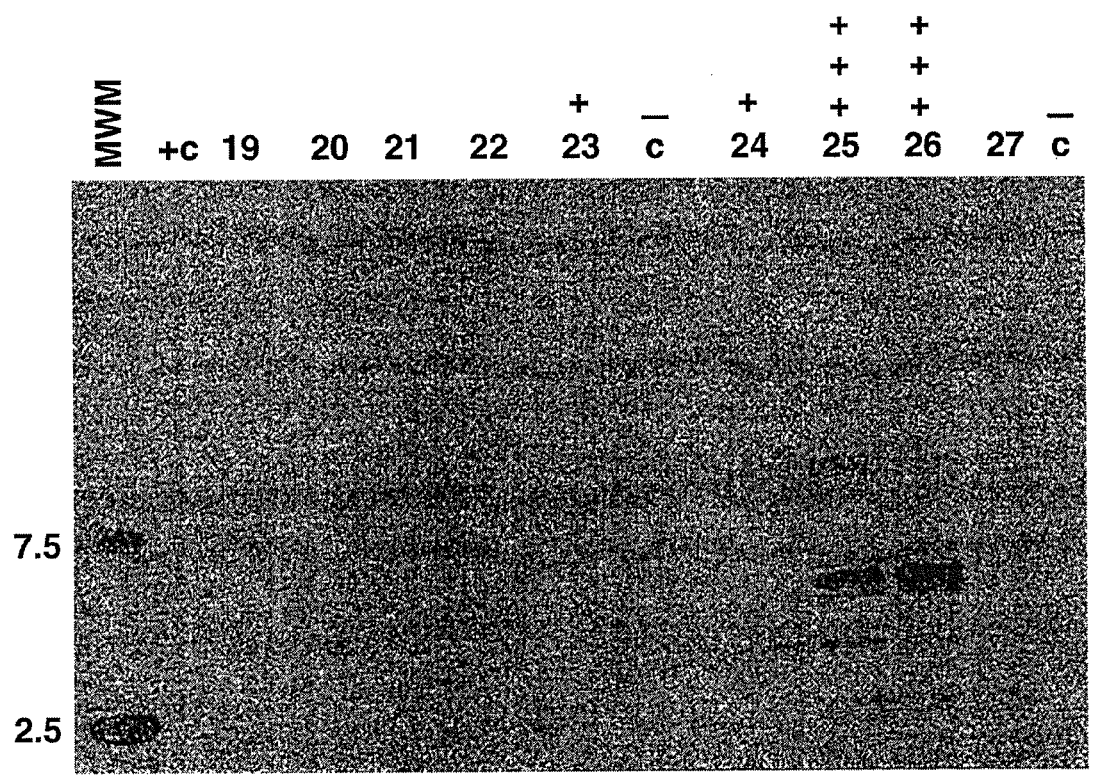
FIG. 12 shows a representative blot of samples of transgenic maize callus for altered lectin binding due to expression of the GntIII gene.

Positive test results (Table 5) for the E-PHA binding were rated as 0 (negative), 1 (one plus, weak) 2 (two pluses, moderately strong) or 3 (three pluses, strongest rating). Callus of events rated 2 or 3 were selected to produce sample for mass analysis. Samples 25, 26, 33, 48, 55, 56 and 59 were pooled to produce the protein extract for MALDI-TOF analysis of glycan substructures. A gel blot example (FIG. 12) shows samples 19 through 27.

Example 10

Test Transgenic Maize Callus for c-myc Epitope Expression

Callus samples from 100 individually isolated unique transgenic events were extracted as follows. Samples from each event were fresh frozen in 96-well cluster tube boxes (Costar Costar 1.2 ml polypropylene, with lid) along with a steel and a tungsten bead in each well. 450 ul of extraction buffer (25 mM sodium phosphate pH6.6, 100 mM NaCl, 30 mM sodium bisulfate, 1% v/v Triton X-100) was added per well and the box of samples was pulverized for 3 minutes full speed on a Kleco Bead Mill. The plate was centrifuged (4° C.) at 2500 rpm for 10 minutes. Extracts were removed to a 96-well deep well plate and frozen for storage. All screening assays were performed on these extracts of individual events.

Protein analyses (microtiter plate protocol, BioRad 500-0006) were made to determine the total protein for each extract. 25 ug protein per sample were loaded in 20 ul loading buffer (Laemmli, U.K. Nature 277:680, 1970)). Gels (4-20% Criterion PAGE gels, 12+2 wells per gel, BioRad 45-0032) were electrophoresed at 65 mA in Tris/glycine/SDS running buffer (BioRad 161-0772). After soaking in transfer buffer (running buffer plus 20% methanol) for 10 minutes, the gels were transferred to nitrocellulose membranes using a semi-dry blotter (150 mA/1.5 hrs). The membranes were incubated for 30 minutes in blocking buffer (20 mM Tris, 144 mM NaCl 0.5% v/v Tween 20, 10% w/v dry milk) at room temperature, then the blocking buffer was removed and replaced with the primary detection reagent, Mouse anti-c-myc clone 9E10 (sigma M5546) at 1 ug/ml in blocking buffer. After 1 hour of incubation at room temperature, the primary detection reagent was removed and the membrane was rinsed with blocking buffer. The secondary detection reagent, anti-mouse-HRP (BioRad 170-6516) at 1:10,000 plus a molecular weight marker detection reagent (StrepTactin-HRP, BioRad 161-0380) at 1:10,000 in blocking buffer, was then added and incubated on the membrane for 1 hour at room temperature. During the blocking, primary, and secondary reagent steps the solutions were mixed on the blots. The secondary detection agent was removed, and the membrane was rinsed three times with Tris buffered saline (20 mM Tris, 144 mM NaCl) containing 0.5% Tween 20 for 10 minutes each, plus another 5 minute rinse. After draining off the excess rinse solution the membrane was soaked in ECL reagent (Pierce 34080) for 1 minute, drained, and then exposed to film.

Figure 13:
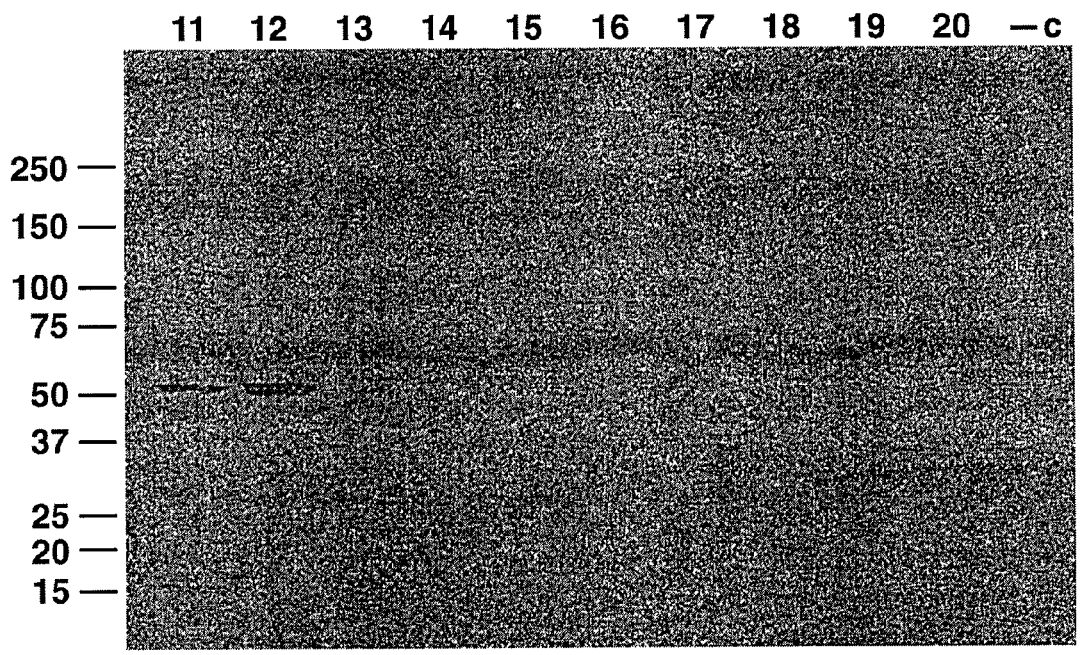
FIG. 13 shows a representative blot of samples of transgenic maize callus for c-myc epitope expression.

As detailed above, callus samples from independent events 1-100 were screened for expression of the c-myc epitope. Then, samples 3, 11, 12, 26, 31, 55 and 64 were analysed and showed the presence of a band in the predicted molecular weight range of 50-55 kilodaltons. These callus samples were pooled to produce a protein sample for glycan analysis by MALDI-TOF. A representative blot is shown in FIG. 13.

Example 11

Preparation of Extract for Mass Spec Analysis of Glycans

The samples were prepared from combined calluses of several maize callus events which tested positive for GnTIII transgene expression based on lectin blotting using E-PHA. Callus tissue was collected fresh and stored frozen at −80° C., then ground to a fine powder in liquid nitrogen. Weighed sample was added to extraction buffer (5 mM EDTA, 0.5 mM PMSF, 20 mM sodium bisulfite, 150 mM sodium phosphate buffer pH 7.4, and 0.4 mM PVPP soluble MW 40,000) and stirred for 30 minutes at 4° C. After centrifugation at 5000×G at 4° C., the supernatant was collected. Ammonium sulfate and wash buffer (5 mM EDTA, 150 mM sodium phosphate buffer, pH 7.4) were added to the supernatant to achieve a final concentration of 20% (w/v) ammonium sulfate. After centrifugation 5 minutes at 5000×G at 4° C., the supernatant was transferred to a fresh tube and additional ammonium sulfate plus wash buffer were added to achieve 60% (w/v) ammonium sulfate. This preparation was stirred overnight at 4° C., then centrifuged 20 minutes at 10,000×G. The pellet was recovered in 5 ml of wash buffer and frozen at −80° C., then lyophilized at 4° C. until dry. Samples were sent to the lab for glycan analysis.

Example 12

Maize Plant Regeneration from Transgenic Callus Tissue

For plant regeneration from transformed callus, tissue was placed onto regeneration media containing MS basal salts and vitamins (Murashige T. and F. Skoog, Physiol Plant 15: 473-497, 1962), 30 g/l sucrose, 5 mg/l 6-benzylaminopurine (BA), 0.025 mg/l 2,4-dichlorophenoxyacetic acid (2,4-D), 1 mg/l Herbiace (a commercial formulation of 20% bialaphos, Meiji Seika, Tokyo, Japan), and 2.5 g/l Gelrite Gelrite, pH 5.7. Cultures were grown in the light. When shoots reached 1-3 cm in length, they were transferred into vessels containing SH basal salts and vitamins (Schenk R. and A. C. Hildebrandt, Can JBot 50: 199-204, 1972), 10 g/l sucrose, 1 g/l myo-inositol, and 2.5 g/l Gelrite Gelrite, pH 5.8.

Plants were screened for expression of GNTIII by altered binding of the lectin E-PHA to endogenous proteins. Samples were then screened for E-PHA binding as described in Example 9, supra. The protein extract and 20%/60% ammonium sulfate precipitate was prepared exactly as for the callus samples as described in Example 13, infra. One plant each from plants regenerated from 23 independent events were screened by lectin blotting for the results of expression of the GNTIII gene. Four of these events gave positive signals for E-PHA binding. These four events had also tested positive at the callus stage. Plants regenerated from those four events were pooled to produce a protein extract for glycan analysis by MALDI-TOF.

Example 13

Figure 9:
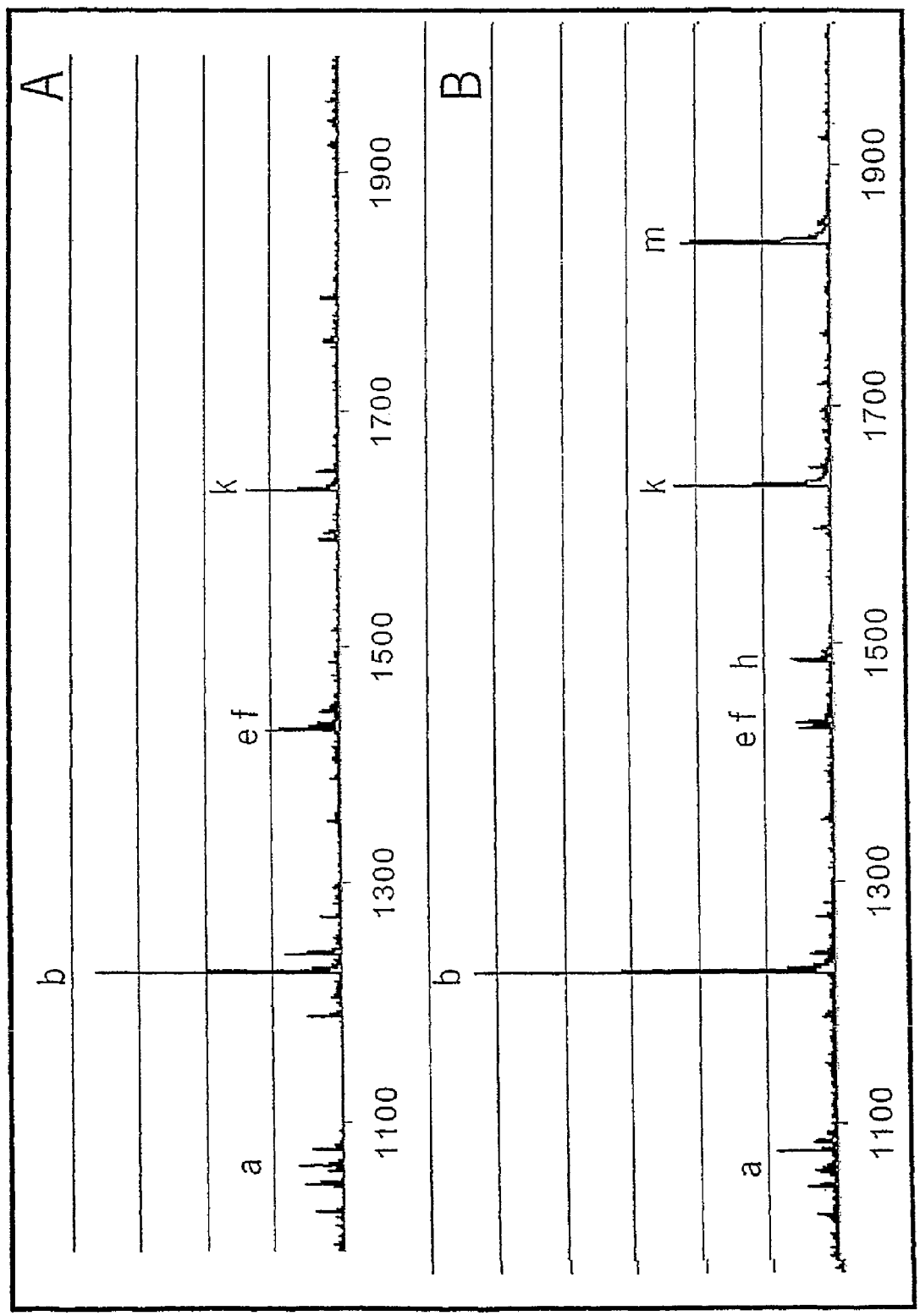
FIGS. 9A and 9B show MALDI-TOF mass spectra of glycoproteins from control and GnTIII corn. Comparison of mass spectra of N-glycans of glycoproteins isolated from calli of (A) control corn and of (B) selected GnTIII-corn. GnTIII corn was obtained through transformation with human GnTIII gene sequence and selection was performed by lectin blotting using E-PHA. See Table 3 for an annotation of the data contained in FIGS. 9A and 9B.

Oligosaccharide Distributions and Level of Bisected Complex Oligosaccharides in Wildtype and Selected Transgenic Corn Calli Endogenous glycoproteins were isolated from control corn calli and selected corn calli expressing GnTIII based on lectin blotting using E-PHA. In addition, the present invention also contemplates the extraction of c-myc tagged samples. E-PHA and c-myc tagged samples may be callus, plant cells, plant tissues or entire plants as defined in the definitions section supra. A comparison of the structures of the N-glycans isolated from glycoproteins present in calli is presented in FIGS. 9A and 9B. MALDI-TOF allowed for the detection of different molecular species in the pool of the N-glycans (glycoforms) and showed a mixture of ions that were assigned to (M+Na)+ adducts of high-mannose (Man)-type N-glycans ranging from d, Man5 to 1, Man8 and of mature N-glycans from the truncated structure a, XM3GN2 to m, bGN3FXM3GN2 (see, Table 3). In addition to the N-glycans characterized in the control callus (FIG. 9A), the MALDI-TOF MS of the glycan mixture from selected corn calli expressing GnTIII (FIG. 9B) showed at least one ion assigned to N-linked glycans that result from the action of the human GnTIII enzyme (for a comparison see, Table 3). This oligosaccharide, GN3XM3GN2 (m) represents 20% of the population and contains three GlcNAc residues each linked to one of the three mannoses of the trimannosyl core structure of the N-linked glycan. Analysis of glycan structure through MALDI-TOF as performed here cannot distinguish between GlcNAc residues $\beta(1,2)$- or $\beta(1,4)$-linked to mannose. Hence it is not clear if or to what extent the structures GN2XM3GN2 (h) and GN2FXM3GN2 (k) have bisecting oligosaccharides. Both had increased numbers in GnTIII corn cells compared to untransformed control corn cells. Additional experiments are required to reveal that these structures are a mix of normal and bisected oligosaccharides or a single compound.

Besides the new appearance of saccharide structure m (bGN3FXM3GN2) in GnTIII corn, it is apparent from the comparison of the glycoforms of control and GnTIII corn, as shown in Table 3, that the amount of structures harbouring high-mannose type N-glycans (M4 and higher) is reduced more than twofold (from 19% to 7%) which can be attributed mostly to the reduction of M4-containing N-glycans (from 10% to 1% of total) in GnTIII corn versus control corn. In addition the amount of glycoforms having two or more GlcNAc residues has increased from 16% to 42% (control versus GnTIII).

In a follow-up experiment, endogenous glycoproteins were isolated from control corn calli and selected corn calli expressing GnTIII based on analysis for the presence of c-myc tag sequence by Western blotting. A comparison of the structures of the N-glycans isolated from glycoproteins present in calli is presented in Table 4. MALDI-TOF allows for the detection of different molecular species in the pool of the N-glycans (glycoforms) and shows a mixture of ions that were assigned to (M+Na)+ adducts of high-mannose (Man)-type N-glycans ranging from d, Man5 to 1, Man8 and of mature N-glycans from the truncated structure a, XM3GN2 to k, GN2FXM3GN2 in control corn.

Remarkably, in transgenic corn expressing GnTIII (Table 4, GnTIII-2), only three isoforms could be detected: FXM3GN2 (b; accounting for 9% of total), GN2FXM3GN2/bGN2FXM3GN2 (k; 38%) and bGN3FXM3GN2 (m; 54%). It is not clear if or to what extent the structure depicted as k (GN2FXM3GN2/bGN2FXM3GN2) has bisecting oligosaccharides. Its presence is significantly increased in GnTIII corn compared to control corn. Additional experiments are required to reveal that these structures are a mix of normal and bisected oligosaccharides or a single compound.

Besides the new appearance of saccharide structure m (bGN3FXM3GN2) in GnTIII corn (54%), it is apparent from the comparison of the glycoforms of control and GnTIII corn, as summarized in Table 4, that the amount of structures harbouring high-mannose type N-glycans (M4 and higher) is reduced to nil in GnTIII corn versus control corn. Furthermore, tha total amount of N-glycans bearing 2 or more (3) GlcNAc residues has increased from 16 to 92% (control versus GnTIII) suggesting that the introduction of bisected GlcNAc residue protects the glycan from degradation by endogenous hexosaminidases as observed before for transgenic GnTIII tobacco.

Figure 11:
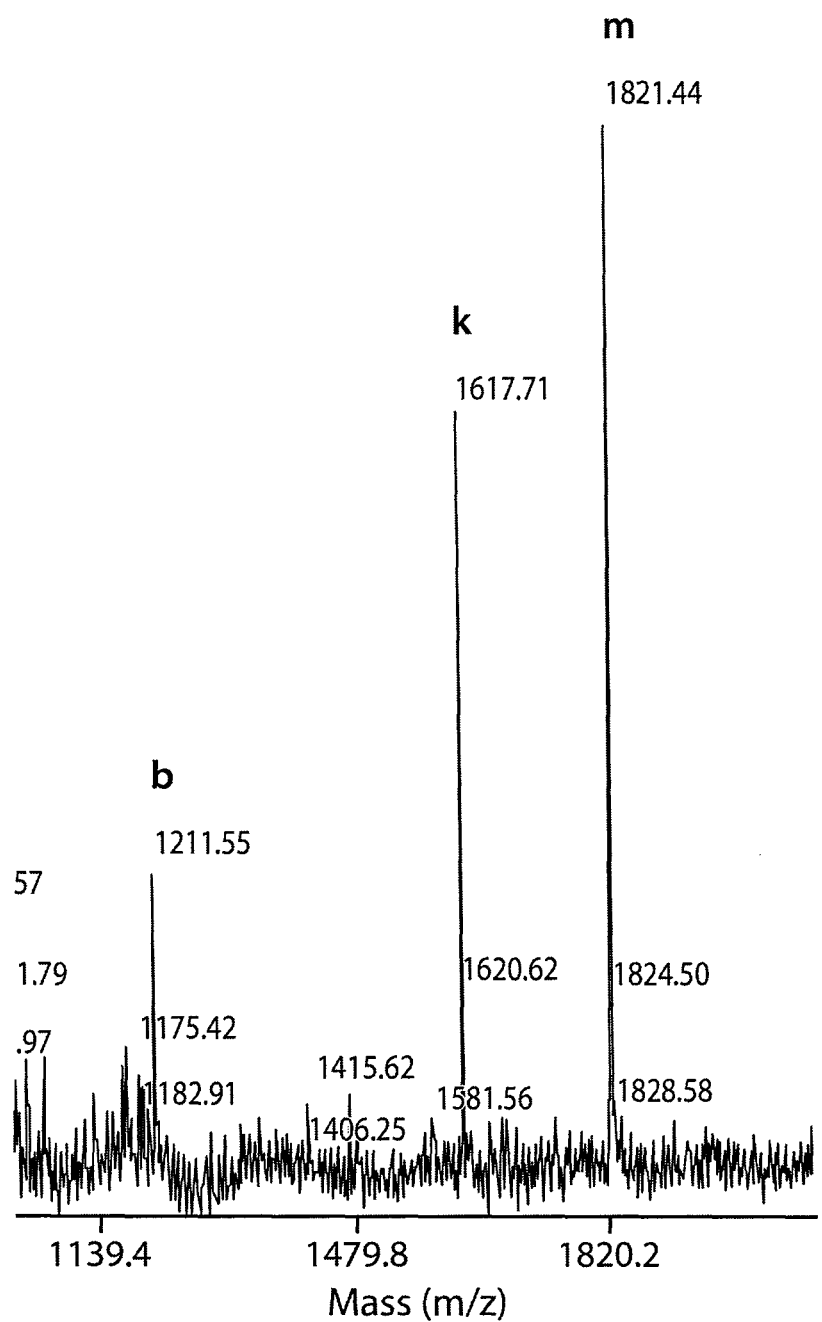
FIG. 11 shows a MALDI-TOF mass spectra of glycoproteins from control and GnTIII corn-2. See, Table 4 for structures and abbreviations.

Additionally, MALDI-TOF mass spectroscopy data (FIG. 11) demonstrate the bisected GlcNAc structure.

Example 14

Oligosaccharide Distributions and Level of Bisected Complex Oligosaccharides in Wildtype and Selected Transgenic Corn Plants Endogenous glycoproteins were isolated from control corn plant leaves and selected corn plant leaves expressing GnTIII based on analysis for the presence of c-myc tag sequence by Western blotting or lectin blotting using E-PHA. A comparison of the structures of the N-glycans isolated from glycoproteins present in leaves is presented in Table 6. MALDI-TOF allows for the detection of different molecular species in the pool of the N-glycans (glycoforms) and shows a mixture of ions that were assigned to (M+Na)+ or (M+K)+ adducts of high-mannose (Man)-type N-glycans ranging from f, Man6 to h, Man8 and of mature N-glycans from the truncated structure a, XM3GN2 to g, GN2FXM3GN2 in control corn plant and to i, bGN3FXM3GN2 in transgenic GnTIII corn plant.

In addition to the N-glycans characterized in the control plants (Figure A), the MALDI-TOF MS of the glycan mixture from selected corn plant expressing GnTIII (Figure B) showed at least one ion assigned to N-linked glycans that result from the action of the human GnTIII enzyme (for a comparison see Table 6). This oligosaccharide, GN3XM3GN2 (i) represents 15% of the population and contains three GlcNAc residues each linked to one of the three mannoses of the trimannosyl core structure of the N-linked glycan. Analysis of glycan structure through MALDI-TOF as performed here cannot distinguish between GlcNAc residues β(1,2)- or β(1,4)-linked to mannose. Hence it is not clear if or to what extent the structure GN2FXM3GN2 (g) has bisecting oligosaccharides. It has increased in GnTIII corn compared to control corn plant (23% versus 5% in control). Additional experiments are required to reveal that these structures are a mix of normal and bisected oligosaccharides or a single compound. Besides this it is apparent from the comparison of the glycoforms of control and GnTIII corn plants, as depicted in Table 6, that the amount of structures harbouring FXM3GN2 is reduced twofold (from 59 to 30) and the amount of glycoforms having two or more GlcNAc residues has increased from 5 to 38% (control versus GnTIII).

Additionally, FIG. 14 shows a comparison of MALDI-TOF mass spectra of N-glycans of glycoproteins isolated from leaves of control corn (A) and of selected GnTIII-corn plants. GnTIII corn plant was obtained through transformation with human GnTIII gene sequence and selection was performed by Western blotting using either c-myc tag or E-PHA lectin. See Table 6 for structures and abbreviations.

It is understood that the present invention is not limited to the particular methodology, protocols, cell lines, vectors, and reagent, etc., described herein, as these may vary. It is also to be understood that the terminology used herein is used for the purpose of describing particular embodiments only, and is not intend to limit the scope of the present invention. It must be noted that as used herein and in the appended claims, the singular forms "a," "an" and "the" include plural reference unless the context clearly dictates otherwise.

Unless defined otherwise, all technical and scientific terms used herein have the same meanings as commonly understood by one of ordinary skill in the art to which this invention belongs.

The invention described and claimed herein is not to be limited in scope by the specific embodiments herein disclosed, since these embodiments are intended as illustrations of severe; aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

TABLE 1

Structure, molecular weight and percentage of total pool of N-glycans isolated from control and selected GnTIII-17 plants.

| Structure | Abbreviation | Name | Mol. Wt. | % Wildtype | % GnTIII-17 |
|---|---|---|---|---|---|
| 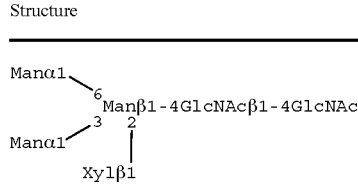 | XM3GN2 | A | 1065 | 8 | 4 |
| 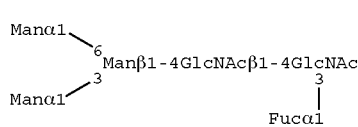 | FM3GN2 | B | 1079 | 3 | 0 |
| 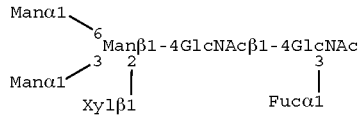 | FXM3GN2 | C | 1211 | 30 | 4 |
|  | Man5 | D | 1257 | 2 | 3 |
| 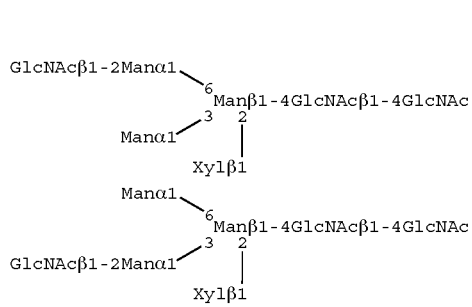 | GNXM3GN2 | E | 1268 | 4 | 0 |

TABLE 1-continued

Structure, molecular weight and percentage of total pool of N-glycans isolated from control and selected GnTIII-17 plants.

| Structure | Abbreviation | Name | Mol. Wt. | % Wildtype | % GnTIII-17 |
|---|---|---|---|---|---|
| GlcNAcβ1-2Manα1⟶6<br>　　　　　　　Manβ1-4GlcNAcβ1-4GlcNAc<br>Manα1⟶3　　　｜　　　　　　　｜<br>　　　　　　Xylβ1　　　　　　Fucα1 | GNFXM3GN2 | F | 1414 | 10 | 2 |
| Manα1⟶6<br>　　　Manβ1-4GlcNAcβ1-4GlcNAc<br>GlcNAcβ1-2Manα1⟶3　｜　　　　　　｜<br>　　　　　　Xylβ1　　　　Fucα1 | | | | | |
| | | Man6 | G | 1419 | 3 | 5 |
| GlcNAcβ1-2Manα1⟶6<br>　　GlcNAcβ1-4 Manβ1-4GlcNAcβ1-4GlcNAc<br>Manα1⟶3　　｜<br>　　　　Xylβ1 | GN2XM3GN2 | H | 1471 | — | ⎫ |
| GlcNAcβ1-2Manα1⟶6<br>　　　　　　Manβ1-4GlcNAcβ1-4GlcNAc<br>GlcNAcβ1-2Manα1⟶3　｜<br>　　　　　Xylβ1 | | | | 4 | ⎬ 14 |
| Manα1⟶6<br>　GlcNAcβ1-4 Manβ1-4GlcNAcβ1-4GlcNAc<br>GlcNAcβ1-2Manα1⟶3　｜<br>　　　Xylβ1 | | | | — | ⎭ |
| | | Man7 | I | 1581 | 3 | 4 |
| GlcNAcβ1-2Manα1⟶6<br>　GlcNAcβ1-4 Manβ1-4GlcNAcβ1-4GlcNAc<br>Manα1⟶3　｜　　　　　　｜<br>　　　Xylβ1　　　　Fucα1 | GN2FXM3GN2 | J | 1617 | — | ⎫ |
| GlcNAcβ1-2Manα1⟶6<br>　　　　　Manβ1-4GlcNAcβ1-4GlcNAc<br>GlcNAcβ1-2Manα1⟶3　｜　　　　｜<br>　　　Xylβ1　　　Fucα1 | | | | 29 | ⎬ 19 |
| Manα1⟶6<br>　GlcNAcβ1-4 Manβ1-4GlcNAcβ1-4GlcNAc<br>GlcNAcβ1-2Manα1⟶3　｜　　　｜<br>　　　Xylβ1　　Fucα1 | | | | — | ⎭ |
| GlcNAcβ1-2Manα1⟶6<br>　GlcNAcβ1-4 Manβ1-4GlcNAcβ1-4GlcNAc<br>GlcNAcβ1-2Manα1⟶3　｜<br>　　　Xylβ1 | GN3XM3GN2 | K | 1674 | — | 8 |
| | | Man8 | L | 1743 | 2 | 4 |
| GlcNAcβ1-2Manα1⟶6<br>　GlcNAcβ1-4 Manβ1-4GlcNAcβ1-4GlcNAc<br>GlcNAcβ1-2Manα1⟶3　｜　　　　｜<br>　　　Xylβ1　　　Fucα1 | GN3FXM3GN2 | M | 1820 | — | 31 |
| | | Man9 | N | 1905 | 1 | 2 |

TABLE 2

Comparison of the results of mass spec (MALDI-TOF) analysis of N-glycans of endogenous glycoproteins isolated from control tobacco and selected GnTIII-17 plant. See also Table 1.

| m/z | Type | Wildtype endo | GnTIII-17 endo |
|---|---|---|---|
| 1065 | XM3 | 8 | 4 |
| 1079 | FM3 | 3 | 0 |
| 1211 | FXM3 | 30 | 4 |
| 1257 | M5 | 2 | 3 |
| 1268 | GNXM3 | 4 | 0 |
| 1414 | GNFXM3 | 10 | 2 |
| 1419 | M6 | 3 | 5 |
| 1471 | GNbGNXM3 |  | 14 |
| 1471 | GN2XM3 | 4 |  |
| 1581 | M7 | 3 | 4 |
| 1617 | GN2FXM3 | 29 | 19 |
| 1617 | GNbGNXM3 |  |  |
| 1674 | GN2bGNXM3 | 0 | 8 |
| 1743 | M8 | 2 | 4 |
| 1820 | GN2bGNFXM3 | 0 | 31 |
| 1905 | M9 | 1 | 2 |
| | TOTAL | 99 | 100 |

TABLE 3

Overview N-glycans observed in control and transgenic GnTIII corn. Comparison of N-glycan structures (% of total) found on endogenous glycoproteins of control, untransformed corn and transgenic corn callus expressing GnTIII that could be annotated. Corresponding mass spectra obtained through MALDI-TOF analyses are given below and saccharides are indicated under column "name." Bisecting GlcNAc residues are depicted as bGN.

| Structure abbreviation | m/z | name | Corn callus control | Corn callus GnTIII |
|---|---|---|---|---|
| XM3GN2 | 1065 | a | 1 | 5 |
| FXM3GN2 | 1211 | b | 37 | 36 |
| XM4GN2 | 1227 | c | 6 | 1 |
| M5GN2 | 1257 | d | 1 | 1 |
| GNFXM3GN2 | 1414 | e | 12 | 3 |
| M6GN2 | 1419 | f | 5 | 4 |
| GNXM4GN2 | 1430 | g | 3 |  |
| GN2XM3GN2 bGN2XM3GN2 | 1471 | h |  | 3 |
| GNFXM4GN2 | 1576 | i | 1 |  |
| M7GN2 | 1581 | j | 1 | 1 |
| GN2FXM3GN2 bGN2FXM3GN2 | 1617 | k | 16 | 19 |
| M8GN2 | 1743 | l | 1 |  |
| bGN3FXM3GN2 | 1820 | m |  | 20 |
| | | Total | 84 | 93 |

TABLE 4

Schematical overview N-glycans observed in control and transgenic GnIII corn-2. Comparison of N-glycan structures (% of total) found on endogenous glycoproteins of control, untransformed corn and transgenic corn callus expressing GnTIII that could be annotated. Transgenic corn was selected using c-myc tag. Corresponding mass spectra obtained through MALDI-TOF analyses are given below and saccharides are indicated under column "name". Bisecting GlcNAc residues are depicted as bGN.

| Structure abbreviation | m/z | name | Corn callus control | Corn callus GnTIII-2 |
|---|---|---|---|---|
| XM3GN2 | 1065 | a | 1 |  |
| FXM3GN2 | 1211 | b | 37 | 9 |
| XM4GN2 | 1227 | c | 6 |  |
| M5GN2 | 1257 | d | 1 |  |
| GNFXM3GN2 | 1414 | e | 12 |  |
| M6GN2 | 1419 | f | 5 |  |
| GNXM4GN2 | 1430 | g | 3 |  |
| GN2XM3GN2 bGN2XM3GN2 | 1471 | h |  |  |
| GNFXM4GN2 | 1576 | i | 1 |  |
| M7GN2 | 1581 | j | 1 |  |
| GN2FXM3GN2 bGN2FXM3GN2 | 1617 | k | 16 | 38 |
| M8GN2 | 1743 | l | 1 |  |
| bGN3FXM3GN2 | 1820 | m |  | 54 |
| | | Total | 84 | 101 |

TABLE 5

Positive test results for E-PHA binding.

| Sample ID number | Rating for E-PHA Binding | Included in Pooled positive sample |
|---|---|---|
| 1. | Unclear |  |
| 2. | Unclear |  |
| 3. | 1 |  |
| 4. | 0 |  |
| 5. | 0 |  |
| 6. | 0 |  |
| 7. | 0 |  |
| 8. | 0 |  |
| 9. | 0 |  |
| 10. | Unclear |  |
| 11. | Unclear |  |
| 12. | 1 |  |
| 13. | 1 |  |
| 14. | 0 |  |
| 15. | 0 |  |
| 16. | 0 |  |
| 17. | 0 |  |
| 18. | 0 |  |
| 19. | 0 |  |
| 20. | 0 |  |
| 21. | 0 |  |
| 22. | 0 |  |
| 23. | 1 |  |
| 24. | 1 |  |
| 25. | 3 | Yes |
| 26. | 3 | Yes |
| 27. | 0 |  |
| 28. | 0 |  |
| 29. | 0 |  |
| 30. | 0 |  |
| 31. | 0 |  |
| 32. | 0 |  |
| 33. | 2 | Yes |
| 34. | 1 |  |
| 35. | 0 |  |
| 36. | 0 |  |
| 37. | Unclear |  |
| 38. | 1 |  |
| 39. | 0 |  |
| 40. | 1 |  |
| 41. | 1 |  |

TABLE 5-continued

Positive test results for E-PHA binding.

| Sample ID number | Rating for E-PHA Binding | Included in Pooled positive sample |
|---|---|---|
| 42. | 0 | |
| 43. | 0 | |
| 44. | Unclear | |
| 45. | 0 | |
| 46. | 0 | |
| 47. | 0 | |
| 48. | 2 | Yes |
| 49. | 0 | |
| 50. | 0 | |
| 51. | 0 | |
| 52. | 0 | |
| 53. | 0 | |
| 54. | 1 | |
| 55. | 2 | Yes |
| 56. | 2 | Yes |
| 57. | 2 | Yes |
| 58. | 1 | |
| 59. | 2 | Yes |
| 60. | 0 | |
| 61. | 0 | |
| 62. | 0 | |
| 63. | 0 | |
| 64. | 0 | |
| 65. | 0 | |
| 66. | 0 | |
| 67. | 0 | |
| 68. | 0 | |
| 69. | Negative control | |

TABLE 6

Schematical overview N-glycans observed in control and transgenic GnTIII corn plants.

| Structure abbreviation | m/z | name | Corn plant control | Corn plant GnTIII |
|---|---|---|---|---|
| XM3GN2 | 1065 | a | 4 | 14 |
| FM3GN2 | 1079 | b | 2 | |
| FXM3GN2 | 1211 | c | 59 | 30 |
| XM4GN2 | 1227 | d | 3 | 12 |
| GNFXM3GN2 | 1414 | e | 10 | 6 |
| M6GN2 | 1419 | f | 2 | |
| GN2FXM3GN2 | 1617 | g | 5 | 23 |
| bGN2FXM3GN2 | | | | |
| M8GN2 | 1743 | h | 1 | |
| bGN3FXM3GN2 | 1820 | i | | 15 |
| Total | | | 86 | 100 |

What is claimed is:

1. An isolated glycoprotein comprising a protein modified by at least one N-glycan, wherein the N-glycan comprises a motif selected from the group consisting of GN2XM3GN2, GN2FXM3GN2, GN3XM3GN2, and GN3FXM3GN2, in which GN is N-acetylglucosamine, X is β1,2-xylose, F is α1,3-fucose and M is mannose, wherein the glycoprotein is produced in a plant host system that expresses a recombinant UDP-N-acetylglucosamine:β-D mannoside β(1,4)-N-acetyl-glucosaminyltransferase (GnTIII), and wherein the at least one N-glycan is synthesized by at least the GnTIII.

2. The glycoprotein of claim 1, wherein the glycoprotein is an antibody, a hormone, a growth factor, a growth factor receptor, an antigen, a cytokine, or a blood protein.

3. The glycoprotein of claim 1, wherein the N-glycan further comprises at least a terminal galactose residue.

4. A composition, comprising the glycoprotein of claim 1 and a carrier.

5. A pharmaceutical composition, comprising the glycoprotein of claim 1 and a pharmaceutically acceptable carrier.

6. A method comprising culturing a plant host system that expresses a heterologous glycoprotein and a glycosyltransferase comprising the active region of a mammalian GnTIII.

7. The method of claim 6, further comprising isolating the glycoprotein.

8. The method of claim 6, wherein the heterologous glycoprotein is an antibody, a hormone, a growth factor, a growth factor receptor, an antigen, a cytokine, or a blood protein.

9. The method of claim 6, wherein the glycosyltransferase GnTIII is a mammalian GnTIII.

10. The method of claim 9, wherein the mammalian GnTIII is a human GnTIII.

11. The method of claim 10, wherein the human GnTIII comprises the amino acid sequence of SEQ ID NO:2.

12. The method of claim 6, wherein the glycosyltransferase GnTIII is a hybrid enzyme comprising the active region of a mammalian GnTIII and the transmembrane region (Tm) of a protein that resides in the endoplasmic reticulum or Golgi apparatus of a eukaryotic cell.

13. The method of claim 12, further comprising isolating the glycoprotein.

14. The method of claim 12, wherein the heterologous glycoprotein is an antibody, a hormone, a growth factor, a growth factor receptor, an antigen, a cytokine, or a blood protein.

15. The method of claim 12, wherein the protein residing in endoplasmic reticulum or Golgi apparatus of a eukaryotic cell is a plant glycosyltransferase.

16. The method of claim 15, wherein the plant glycosyltransferase is selected from the group consisting of mannosidase I, mannosidase II, GnTI, GnTII, XylT and FucT.

17. The method of claim 15, wherein the hybrid enzyme is TmGnTI-GnTIII, TmManII-GnTIII, or TmXyl-GnTIII.

18. The method of claim 16, further comprising isolating the glycoprotein.

19. The method of claim 18, wherein the heterologous glycoprotein is an antibody, a hormone, a growth factor, a growth factor receptor, an antigen, a cytokine, or a blood protein.

20. The method of claim 6, wherein the plant host system is a whole plant or a portion thereof.

21. The method of claim 20, wherein the plant host system is a tobacco plant or a portion thereof.

22. The method of claim 20, wherein the plant host system is a portion of a whole plant selected from the group consisting of leaf, callus, stem, pericarp, protoplast, root, tuber, kernel, endosperm, and embryo.

23. The method of claim 6, wherein the plant host system is a plant cell.

24. The method of claim 6, wherein the plant host system further comprises at least one additional non-plant glycosyltransferase that is involved in N-glycan synthesis.

25. The method of claim 24, wherein the at least one additional non-plant glycosyltransferase is a mammalian β-1,4 galactosyltransferase.

26. A glycoprotein produced by a method comprising culturing a plant host system that expresses a heterologous glycoprotein and a glycosyltransferase comprising of a mammalian GnTIII.

27. The glycoprotein of claim 26, wherein the plant host system further comprises at least one additional non-plant glycosyltransferase that is involved in N-glycan synthesis.

* * * * *

UNITED STATES PATENT AND TRADEMARK OFFICE
CERTIFICATE OF CORRECTION

PATENT NO. : 8,492,613 B2
APPLICATION NO. : 12/980651
DATED : July 23, 2013
INVENTOR(S) : Hendrikus Antonius Cornelis Bakker et al.

It is certified that error appears in the above-identified patent and that said Letters Patent is hereby corrected as shown below:

In the Claims:

At column 104, lines 15-21, claim 26 should read:

"A glycoprotein produced by a method comprising culturing a plant host system that expresses a heterologous glycoprotein and a glycosyltransferase comprising the active region of a mammalian GnTIII."

Signed and Sealed this
Fifteenth Day of October, 2013

Teresa Stanek Rea
*Deputy Director of the United States Patent and Trademark Office*